United States Patent
Cole et al.

(10) Patent No.: US 7,951,803 B2
(45) Date of Patent: May 31, 2011

(54) 8-HETEROARYLPURINE MNK2 INHIBITORS FOR TREATING METABOLIC DISORDERS

(75) Inventors: Andrew G. Cole, Robbinsville, NJ (US); Marc-Raleigh Brescia, Dayton, NJ (US); Joan J. Zhang, Plainsboro, NJ (US); Zahid Hussain, Monmouth Junction, NJ (US); David J. Diller, East Windsor, NJ (US); Axel Metzger, East Windsor, NJ (US); Gulzar Ahmed, Voorhees, NJ (US); Ian Henderson, Hopewell, NJ (US)

(73) Assignee: Pharmacopeia, LLC, San Diego, CA (US)

( * ) Notice: Subject to any disclaimer, the term of this patent is extended or adjusted under 35 U.S.C. 154(b) by 921 days.

(21) Appl. No.: 11/684,262

(22) Filed: Mar. 9, 2007

(65) Prior Publication Data
US 2008/0032971 A1    Feb. 7, 2008

Related U.S. Application Data

(60) Provisional application No. 60/780,800, filed on Mar. 9, 2006.

(51) Int. Cl.
C07D 473/32 (2006.01)
A61K 31/52 (2006.01)
A61P 3/10 (2006.01)
A61P 3/04 (2006.01)
A61P 19/02 (2006.01)
C07D 409/12 (2006.01)
C07D 239/26 (2006.01)
C07D 239/28 (2006.01)

(52) U.S. Cl. ........ 514/234.2; 514/252.16; 514/263.21; 514/263.22; 514/263.23; 514/263.4; 544/118; 544/277; 544/162; 544/324; 544/326; 544/332; 546/232

(58) Field of Classification Search ........... 514/234.2, 514/263.23, 263.21, 263.22, 252.16, 263.4; 544/118, 277
See application file for complete search history.

(56) References Cited

U.S. PATENT DOCUMENTS

| | | | |
|---|---|---|---|
| 6,372,740 B1 * | 4/2002 | Murata et al. | 514/234.2 |
| 7,105,526 B2 * | 9/2006 | Otake et al. | 514/263.22 |
| 2007/0021443 A1 * | 1/2007 | Ohlmeyer et al. | 514/263.22 |
| 2007/0225304 A1 * | 9/2007 | Cole et al. | 514/263.22 |
| 2008/0085907 A1 * | 4/2008 | Guillemont et al. | 514/261.1 |
| 2008/0085909 A1 * | 4/2008 | Roughton et al. | 514/263.22 |
| 2008/0119496 A1 * | 5/2008 | Ohlmeyer et al. | 514/263.21 |
| 2008/0214580 A1 * | 9/2008 | Neagu et al. | 514/263.2 |
| 2008/0220256 A1 * | 9/2008 | Bhattacharya et al. | 428/408 |
| 2008/0287468 A1 * | 11/2008 | Ohlmeyer et al. | 514/263.2 |
| 2009/0023723 A1 * | 1/2009 | Cole et al. | 514/234.2 |
| 2009/0069289 A1 * | 3/2009 | Neagu et al. | 514/210.21 |

FOREIGN PATENT DOCUMENTS

| | | |
|---|---|---|
| EP | 0 819 129 B1 | 2/2000 |
| WO | WO 02/103361 A1 | 12/2002 |
| WO | WO 03/006465 | 1/2003 |
| WO | WO 03/037362 A2 | 5/2003 |
| WO | WO 2007/030438 | 3/2007 |
| WO | WO 2008051826 A2 * | 5/2008 |

OTHER PUBLICATIONS

International Search Report for PCT/US2007/063699.
Knauf, Ursula et al., "Negative Regulation of Protein Translation by Mitogen-Activated Protein Kinase-Interacting Kinases 1 and 2," Molecular and Cellular Biology, Aug. 2001, vol. 21, No. 16, pp. 5500-5511.

* cited by examiner

*Primary Examiner* — Mark L Berch
(74) *Attorney, Agent, or Firm* — Knobbe Martens Olson & Bear LLP

(57) ABSTRACT

Compounds of the formula

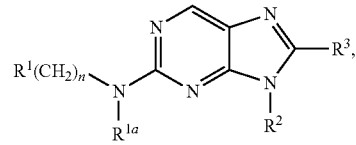

wherein $R^1$ represents optionally substituted $C_1$-$C_{10}$ alkyl, aryl or heteroaryl, and $R^3$ represents alkoxy-substituted aryl or optionally substituted heteroaryl, are disclosed as Mnk2 inhibitors which are useful for the treatment and prevention of metabolic disorders such as obesity and diabetes.

20 Claims, No Drawings

8-HETEROARYLPURINE MNK2 INHIBITORS FOR TREATING METABOLIC DISORDERS

CROSS REFERENCE TO RELATED APPLICATIONS

This application claims benefit from U.S. Provisional Application 60/780,800, filed Mar. 9, 2006, the entire contents of which is incorporated herein by reference.

FIELD OF THE INVENTION

The present invention relates to 8-heteroarylpurine inhibitors of Mnk2, which are useful for the treatment and prevention of metabolic diseases.

BACKGROUND OF THE INVENTION

One of the major hormones that influences metabolism is insulin, which is synthesized in the beta cells of the islets of Langerhans of the pancreas. Insulin primarily regulates the direction of metabolism, shifting many processes toward the storage of substrates and away from their degradation (for reviews, see e.g. Shepherd, P. R. et al. (1998) Biochem. J. 333: 471-490; Alessi, D. R. & Downes, C. P. (1998) Biochim. Biophys. Acta 1436: 151-164). Insulin is believed to be involved in the transport of glucose and amino acids as well as key minerals such as potassium, magnesium, and phosphate from the blood into cells. Insulin is also believed to regulate a variety of enzymatic reactions within the cells, which involve the synthesis of large molecules from smaller building block units. A deficiency in the action of insulin (diabetes mellitus) can cause severe impairment in (i) the storage of glucose in the form of glycogen and the oxidation of glucose for energy; (ii) the synthesis and storage of fat from fatty acids and their precursors and the completion of fatty-acid oxidation; and (iii) the synthesis of proteins from amino acids.

There are two varieties of diabetes. Type I is insulin-dependent diabetes mellitus (IDDM; formerly referred to as juvenile onset diabetes), for which administration of insulin is required. In this type, insulin is not secreted by the pancreas and hence must be administered. Type II diabetes, i.e. non-insulin-dependent diabetes mellitus (NIDDM), is characterized clinically by hyperglycemia and insulin resistance and is commonly associated with obesity. Type II diabetes is a heterogeneous group of disorders in which hyperglycemia typically results from both an impaired insulin secretory response to glucose and decreased insulin effectiveness in stimulating glucose uptake by skeletal muscle and in restraining hepatic glucose production (insulin resistance). Before diabetes develops, patients generally lose the early insulin secretory response to glucose and may secrete relatively large amounts of proinsulin. In established diabetes, although fasting plasma insulin levels may be normal or even increased in type II diabetes patients, glucose-stimulated insulin secretion is clearly decreased. The decreased insulin levels typically reduce insulin-mediated glucose uptake and fail to restrain hepatic glucose production.

Glucose homeostasis depends upon a balance between glucose production by the liver and glucose utilization by insulin-dependent tissues, such as fat and muscle, and insulin-independent tissues, such as brain and kidney. In type II diabetes, the entry of glucose into fat and muscle is reduced and glucose production in the liver is increased, due to insulin resistance in the tissues.

The receptor tyrosine kinases (RTKs) are a class of cell-surface receptors. The ligands for RTKs include peptide/protein hormones including nerve growth factor (NGF), platelet-derived growth factor (PDGF), epidermal growth factor (EGF), and insulin. Binding of a ligand to an RTK is believed to stimulate the receptor's intrinsic protein-tyrosine kinase activity, which subsequently can stimulate a signal-transduction cascade leading to changes in cellular physiology and patterns of gene expression. RTK signaling pathways have a wide spectrum of functions including regulation of cell proliferation and differentiation, promotion of cell survival, and modulation of cellular metabolism.

The platelet-derived growth factor receptor (PDGFR) and the Fms-like tyrosine kinase 3 (FLT-3) have been implicated in a number of pathologies, especially in various cancers, and are therefore considered as drug targets. Both are members of the class III receptor tyrosine kinase (RTK) family, which also includes the receptors for the stem cell factor (c-KIT), and for the colony stimulating factor 1 (CSF1R). The PDGF receptor is involved in wound healing and regulation of homeostasis of the connective tissue compartment. It is expressed on early stem cells, mast cells, myeloid cells, mesenchymal cells, and smooth muscle cells. Overactivity/-expression of PDGFR has been implicated in malignancies as well as in different diseases involving excessive cell growth such as atherosclerosis and fibrosis. The FLT-3 receptor is crucial for the maintenance, proliferation, and differentiation processes in haematopoiesis. FLT-3 is expressed by normal myeloid and lymphoid early progenitors as well as by leukemic cells. Inhibition of the tyrosine kinase activity of the receptor is a therapeutic concept of current interest in anti-leukemia drug research. This new approach to the treatment of acute myeloid leukemia (AML) has emerged following evidence that constitutive activation of the FLT-3 receptor plays an important role in the development of this aggressive haematological malignancy for which no effective cure exists at the moment (see e.g. Markovic, A. et al. (2005) Int. J. Biochem Cell Biol. 37(6): 1168-1172).

Ras is a GTP-binding switch protein that acts in a manner similar to a key signaling molecule in pathways triggered by activation of RTKs. In general, Ras-linked RTKs in mammalian cells appear to utilize a highly conserved signal-transduction pathway in which activated Ras induces a kinase cascade that culminates in the activation of MAP kinase (mitogen-activated protein kinase). This serine/threonine kinase, which can translocate into the nucleus, phosphorylates many different proteins including transcription factors that regulate expression of what are considered to be important cell-cycle and differentiation-specific proteins.

The murine MNK1 and MNK2 gene products ("MAP kinase interacting kinase" or "MAP kinase signal-integrating kinase" 1 and 2) are single-domain serine/threonine kinases that share 72% sequence identity (Waskiewicz A. J. et al. (1997) EMBO J. 16: 1909-1920; GenBank Accession Nos. Y11091 and Y11092). Human MNK1 has also been described (Fukunaga, R. et al. (1999) EMBO J. 16: 1921-1933; GenBank Accession No. AB000409). All these three proteins were identified, in part, by their ability to bind tightly to MAP kinases. Both MNK1 and 2 bind the extracellular signal-regulated kinases ERK1 and ERK2, and MNK1 also binds the stress-activated kinase, p38. The eukaryotic initiation factor 4E (eIF4E) has been identified as one of the physiological substrates of MNK1 and MNK2 (Scheper, G. C. et al. (2001) Mol. Cell. Biol. 21: 743-754).

According to the findings of Harris et al. (*Blood* (2004), vol. 104:5, pp 1314-1323), some eIFs, such as eIF4E, selectively enhance expression of growth-promoting (e.g. cyclin D) and metastasis-related mRNAs (e.g. vascular endothelial growth factor), thus suggesting that translation control through regulation of eiFs may play a role in tumor growth control.

The human mnk2 gene has been identified and characterized through a yeast two-hybrid screen in which the MNK2 protein interacted with the ligand-binding domain of the estrogen receptor (ERβ) (Slentz-Kesler, K. et al. (2000) Genomics 69: 63-71). It was shown that the human mnk2 gene has two C-terminal splice variants, designated mnk2a (GenBank Accession No. AF237775) and mnk2b (GenBank Accession No. AF237776). The two isoforms have been shown to be identical over the first 385 amino acids of the coding sequence and differ only in the final exon, which encodes an additional 80 residues for mnk2a and 29 residues for mnk2b. It was further shown that the MNK2 interaction was selective for estrogen receptor (ER) as opposed to ERI and that the interaction was specific to MNK2b as opposed to MNK2a or MNK1.

WO 02/103361 discloses that MNK2 is involved in the insulin-signaling pathway and features a method for identifying a modulator of glucose uptake. WO 03/037362 suggests that MNK kinases, particularly MNK2 (MNK2a and MNK2b), are involved in the regulation of body-weight and thermogenesis, and thus may be associated with metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defense, such as diabetes mellitus, neurodegenerative disorders, and cancer, e.g. cancers of the reproductive organs. According to WO 2005/003785, the MNK kinases are believed to be promising targets for anti-inflammatory therapy.

Obesity is one of the most prevalent bodyweight disorders in the world. Obesity is defined as a body weight more than 20% in excess of the ideal bodyweight. It is associated with an increased risk for cardiovascular disease, hypertension, diabetes, hyperlipidemia and an increased mortality rate. Obesity is considered a condition with potential multiple causes and is characterized by elevated fasting plasma insulin and an exaggerated insulin response to oral glucose intake.

The MNK1 protein has been shown by Worch et al. (*Oncogene* (2004); 23:9162-9172) to be induced by acute myeloid leukaemia (AML) translocation products, PML-RARα, PLZF-RARα and AML1-ETO, in cell lines, by stabilization of the MNK1 protein. Inhibition of MNK1 enhanced hematopoietic cell differentiation. In AML patients 25 of 99 samples of bone marrow showed MNK1 expression with cytoplasmic localization and in these patients MNK1 expression was associated with the oncogene, c-Myc, protein expression.

Compounds that inhibit Mnk2 are important for the prevention and treatment of diseases and disorders related to bodyweight regulation and thermogenesis. In particular, PCT application WO 03/037362 and references cited therein disclose small molecule inhibitors of Mnk2 such as CGP57380 that are said to be useful for the prevention and treatment of metabolic diseases such as obesity and diabetes.

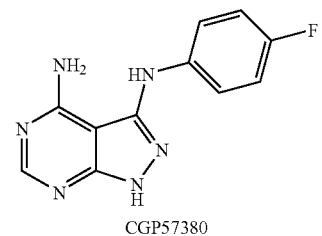

CGP57380

A clear correlation exists between obesity and type 2 diabetes. Type 2 diabetes, otherwise known as diabetes mellitus, develops most often in obese individuals. It is characterized by hyperglycemia resulting from impaired insulin sensitivity coupled with the body's inability to compensate for increased insulin production, rather than an actual deficiency of insulin secretion as with type 1 diabetes. Type 2 diabetes and obesity are characterized by an overexpression of Mnk2. Therefore inhibition of Mnk2 aids in the treatment and prevention of these two widespread diseases.

Several findings suggest that Mnk2 modulates the RAS/MAP kinase pathway and thereby modulates response to insulin and glucose homeostasis. In mammalian systems, overexpression of Mnk2b results in defects in MAP kinase signaling and glucose uptake (WO 02/103361). Mnk2b overexpression decreases glucose uptake in mouse adipocytes and human neuronal cells in vitro. Glucose uptake in the neuronal cell line can be increased by the knockdown of endogenous Mnk2 using RNAi (RNA interference). As a result of these findings, persons of skill expect that an inhibitor of Mnk2 will be beneficial in limiting blood glucose levels.

SUMMARY OF THE INVENTION

The present invention relates to 8-heteroarylpurine compounds used to inhibit Mnk-2 for the treatment and prevention of metabolic disorders.

In one aspect, the invention relates to compounds of formula I, which inhibit Mnk2.

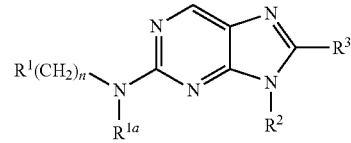

I

In these compounds $R^1$ is chosen from aryl, heteroaryl, and $C_1$-$C_{10}$ alkyl, substituted aryl, substituted heteroaryl, and substituted $C_1$-$C_{10}$ alkyl. $R^{1a}$ is hydrogen or methyl and $R^2$ is chosen from hydrogen, $C_1$-$C_6$ alkyl, and $C_1$-$C_6$ alkyl substituted with CN, lower alkoxy, and fluorine. $R^3$ is chosen from aryl substituted with one or two alkoxy, and heteroaryl optionally substituted with one to three substituents chosen from the group consisting of lower alkyl, hydroxyl, hydroxyloweralkyl, lower alkoxy, amino, alkylamino, dialkylamino, and acylamino alkoxycarbonyl, and halogen. In another aspect, the invention relates to pharmaceutical formulations comprising a pharmaceutically acceptable carrier and a compound of formula I. In another aspect the invention related to methods for treating and preventing metabolic disorders (such as obesity), type 2 diabetes comprising administering compounds of the invention to a patient in need of such prevention or treatment. A further aspect of the invention relates to a method of prevention or treatment of eating disorders, cachexia, mellitus, osteoarthritis, gallstones, sleep apnea, neurodegenerative disorders, and cancer, comprising administering a pharmaceutical formulation according to any of claims 1-18 to a patient in need of such prevention or treatment. The invention also relates to a method of inhibiting Mnk2 activity comprising exposing an Mnk2-active cell to any of the compounds disclosed herein, as well as method of inhibiting Mnk1 activity comprising exposing an Mnk1-active cell to any of the compounds disclosed herein. Further, the invention related to a method of inhibiting Flt-3 activity comprising exposing an Flt-3 active cell to any of the compounds disclosed herein.

DETAILED DESCRIPTION OF THE INVENTION

Throughout this application, references are cited. The disclosure of these publications in their entireties are hereby incorporated by reference as if written herein.
Definitions In this specification the terms and substituents are defined when introduced and retain their definitions throughout.

Alkyl is intended to include saturated linear, branched, or cyclic hydrocarbon structures and combinations thereof. When not otherwise restricted, the term refers to alkyl of 10 or fewer carbons. Lower alkyl refers to alkyl groups of 1, 2, 3, 4, 5 and 6 carbon atoms. Examples of lower alkyl groups include methyl, ethyl, propyl, isopropyl, butyl, s-and t-butyl and the like. Preferred alkyl and alkylene groups are those of $C_{10}$ or below (e.g. $C_1$, $C_2$, $C_3$, $C_4$, $C_5$, $C_6$, $C_7$, $C_8$, $C_9$, $C_{10}$); most preferred are lower alkyl. Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$) includes alkyl, cycloalkyl, alkenyl, alkynyl, aryl and combinations thereof. Examples include benzyl, phenethyl, cyclohexylmethyl and naphthylethyl.

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. Methoxy is preferred. For the purpose of this application, alkoxy and lower alkoxy include methylenedioxy and ethylenedioxy.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Bicyclic and tricyclic aryl residues that are at least partially aromatic, but not all rings need to be aromatic. Aromatic 6, 7, 8, 9, 10, 11, 12, 13 and 14-membered carbocyclic rings include, e.g. benzene, naphthalene, indane, tetralin, and fluorene and the 5, 6, 7, 8, 9 and 10-membered aromatic heterocyclic rings include, e.g. imidazole, pyridine, indole, thiophene, benzopyranone, thiazole, furan, benzimidazole, quinoline, isoquinoline, quinoxaline, pyrimidine, pyrazine, tetrazole and pyrazole. Arylalkyl means an alkyl residue attached to an aryl ring. Examples are benzyl, phenethyl and the like.

The term "heterocycle" means a monocyclic, bicyclic or tricyclic residue with 1 to 13 carbon atoms and 1 to 4 heteroatoms chosen from the group consisting of nitrogen, oxygen and sulfur. The heterocycle may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolidinyl, 1,3-dioxolanyl, imidazolinyl, imidazolidinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dithianyl, thiomorpholinyl, pyrazinyl, piperazinyl, 1,3,5-triazinyl, 1,2,5-trithianyl, benzo(b)thiophenyl, benzimidazolyl, quinolinyl, and the like. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine. Nitrogen heteroaryl is a subset of nitrogen heterocycle; examples include pyridine, pyrrole and thiazole.

Substituted alkyl, aryl, cycloalkyl, heterocyclyl etc. refer to alkyl, aryl, cycloalkyl, or heterocyclyl wherein up to three H atoms in each residue are replaced with halogen, alkyl, haloalkyl, haloalkoxy, hydroxy, loweralkoxy, which for the purpose of the present disclosure includes methylene dioxy and ethylene dioxy, oxaalkyl, carboxy, carbalkoxy (also referred to as alkoxycarbonyl), carboxamido (also referred to as alkylaminocarbonyl), cyano, carbonyl, nitro, amino, hydroxyalkyl, alkylamino, dialkylamino, aminoalkyl, (alkyl) (aryl)aminoalkyl, alkylaminoalkyl (including cycloalkylaminoalkyl), dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, phenyl, benzyl, heteroaryl, heterocyclylalkyl, phenoxy, benzyloxy, or heteroaryloxy. Haloalkyl refers to an alkyl group in which one or more hydrogens are replaced by halogen. For example, trifluoromethyl, trifluoromethoxy, trichloroethyl, and difluoromethyl.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds).

The term "halogen" or "halo" refers to fluorine, chlorine, bromine or iodine.

The term "prodrug" refers to a compound that is made more active in vivo. Commonly the conversion of prodrug to drug occurs by enzymatic processes in the liver or blood of the mammal.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, sulfur, and fluorine include $^3$H, $^{14}$C, $^{32}$P, $^{35}$S, and $^{18}$F, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Radiolabeled compounds of Formulas I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with lipid disorders. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. The term "mammal" includes, for example, mice, hamsters, rats, cows, sheep, pigs, goats, horses, monkeys, dogs (e.g., *Canis familiaris*), cats, rabbits, guinea pigs, and primates, including humans.

The compounds may be use to treat or prevent type 2 diabetes and related metabolic disorders, such as obesity. The relation of Mnk2 and such disorders is described in PCT applications WO 02/103361 and WO 03/037362 and are incorporated herein by reference.

When $R^1$ and $R^2$ contain asymmetric centers, compounds may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

The terminology related to "protecting", "deprotecting" and "protected" functionalities is well understood by persons of skill in the art and can be used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified a person of ordinary skill can readily envision those groups that would be suitable as "protecting groups".

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

While it may be possible for the compounds of formula I to be administered as the raw chemical, it is preferable to present them as a pharmaceutical composition. According to a further aspect, the present invention provides a pharmaceutical composition comprising a compound of formula I with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I and a pharmaceutically acceptable carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation.

The dose range for adult humans is generally from 0.005 mg to 10 g/day orally. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

As used herein, and as would be understood by the person of skill in the art, the recitation of "a compound" is intended to include salts, solvates and inclusion complexes of that compound.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in *Remington: The Science and Practice of Pharmacy* 19$^{th}$ Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from, chloroprocaine, choline, diethanolamine, ethylenediamine, meglumine (N-methylglucamine) and procaine.

Compounds of the genus represented by formula I above are inhibitors of Mnk2. As such, they have utility in treating and preventing type 2 diabetes and metabolic related disorders, such as obesity, as well as related disorders such as eating disorders, cachexia, hypertension, coronary heart disease, hypercholesterolemia, dyslipidemia, osteoarthritis, gallstones, sleep apnea, neurodegenerative disorders, cancer, and other diseases and disorders.

According to the present invention, certain 8-heteroarylpurine derivatives inhibit MAP kinase interacting kinases MNK2a and MNK2b.

Additionally, the compounds of the invention have surprisingly been found by the present inventors also to have MNK1 activity. Based on the compounds tested, the MNK1 and MNK2 (tested as MNK2a) activities of the compounds of the invention are believed to be of a similar magnitude, such as generally within an activity ratio of MNK1:MNK2 of 1:20 to 20:1.

According to WO2005/003785, the MNKs (encompassing MNK1 and MNK2) are believed to be promising targets for anti-inflammatory therapy. Since the present compounds have been found to be highly active in inhibiting MNK2, and also MNK1, as described above, the present compounds are thus likely to be useful in anti-inflammatory therapy.

MNK1 as an interesting target for anti-inflammatory therapy is also strengthened by the findings of Buxadé et al. (Immunity (2005); vol. 23:177-189) according to which heterogeneous nuclear ribonucleoprotein A1, hnRNP A1, is shown to be another substrate for MNK1. hnRNP A1 is involved in the synthesis of TNFα.

The compounds described herein can be used in the treatment or prophylaxis of any disorder or condition associated with the activity of MNK1, MNK2a, MNK2b and/or FLT-3, such as metabolic diseases, e.g. obesity, as well as related disorders such as eating disorder, cachexia, diabetes mellitus, hypertension, coronary heart disease, hypercholesterolemia, dyslipidemia, hyperlipidemia, hyperglycemia, osteoarthritis, gallstones, and sleep apnea, and disorders related to ROS defense, such as diabetes mellitus, neurodegenerative disorders, and cancer, e.g. cancers of the reproductive organs, leukaemia, e.g. acute myeloid leukaemia (AML), and inflammatory conditions. It may also be used in the treatment or prophylaxis of disorders relating to the insulin-signaling pathway. Examples of such disorders are type 2 diabetes.

In one aspect of the invention, R$^3$ is chosen from heteroaryl optionally substituted with one to three substituents chosen from the group consisting of lower alkyl, hydroxy, lower alkoxy, amino, alkylamino, dialkylamino, and acylamino. In another aspect of the invention, R$^1$ is chosen from aryl, heteroaryl, and C$_1$-C$_{10}$ alkyl, each optionally substituted with one to three substituent(s) chosen from lower alkyl, halo, lower alkoxy, haloalkyl, hydroxy, cyano, nitro, amino, alkylamino, dialkylamino, aminoalkyl, alkylaminoalkyl, dialkylaminoalkyl, mercapto, alkylthio, alkylsulfinyl, alkylsulfonyl, sulfone, acylamino, oxaalkyl, heterocyclylalkyl, dialkylaminoalkoxy, (alkyl)(acyl)aminoalkyl, trifluoromethoxy, acylaminoalkoxy, heterocyclylalkoxy, and acylaminoalkyl. In a further aspect of the invention, R$^1$ is phenyl substituted with one substitutent chosen from methylenedioxy, halogen, alkyl, aminomethyl, alkylaminomethyl, dialkylaminomethyl, oxaalkyl, dialkylaminoalkoxy, (alkyl)(acyl)aminoalkyl, trifluoromethoxy, acylaminoalkoxy, heterocyclylalkoxy, and

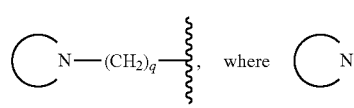

is a nitrogen heterocycle; and
q is 1-3.

R¹ may also be phenyl or phenyl substituted with methylenedioxy, lower alkyl, halogen, alkyl, aminomethyl, alkylaminomethyl, dialkylaminomethyl, acylamino, and acylaminoalkyl, or when R¹ is thienyl n is 2. In a further embodiment, R¹ is lower alkyl and n is 0. Also, R¹ᵃ may be H. In one aspect of the invention, R² is $C_1$-$C_3$ alkyl, fluorinated $C_1$-$C_3$ alkyl, and cyano $C_1$-$C_3$ alkyl. In a further aspect of the invention, R² is chosen from cyclopropyl, isopropyl, 2-cyanoethyl, ethyl, trifluoroethyl, hydrogen, and methyl and R³ is chosen from nitrogen heteroaryl and substituted nitrogen heteroaryl.

In a further aspect of the invention, R³ is formula II

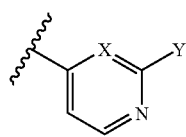

II and X is chosen from CH, C-halogen, and nitrogen, Y is chosen from H, halogen, $NH_2$, NHME, NHEt, $NMe_2$, NHAc, OH, OMe, OEt, Me, and Et. In a further aspect, R³ is substituted phenyl or R³ is chosen from 4-pyridinyl, 2-aminopyrimidin-4-yl and 2-(methylamino)pyrimidin-4-yl or R³ is chosen from 4-pyridyl, 4-pyrimidinyl, 4-(2-aminopyrimidyl), and 4-(2-aminopyridinyl). In a further embodiment, R¹ is phenyl and phenyl substituted with alkoxy, lower alkyl, halogen, aminoalkyl, or acylaminoalkyl, n is chosen from 0, 1, and 2, R¹ᵃ is hydrogen, R² is cyclopropyl, isopropyl, ethyl, 2-cyano-ethyl, trifluoroethyl, hydrogen, and methyl. In a further aspect, R³ is chosen from 4-pyridyl, 4-pyrimidinyl, 4-(2-aminopyrimidyl), and 4-(2-aminopyridinyl).

The present invention is also directed to methods of preventing or treating type 2 diabetes and metabolic disorders, such as obesity by exposing Mnk2 active cells to compounds of the general formula I above.

Further, a compound according to formula 1 may be chosen from:
9-Cyclopropyl-8-(2-(methylamino)pyrimidin-4-yl)-N-m-tolyl-9H-purin-2-amine;
N-(4-(9-Methyl-8-(pyridin-4-yl)-9H-purin-2-ylamino)benzyl)-N-methylacetamide;
8-(2-Aminopyridin-4-yl)-9-cyclopropyl-N-(3-methoxyphenyl)-9H-purin-2-amine;
8-(2-Aminopyrimidin-4-yl)-9-ethyl-N-(4-fluoro-3-methylphenyl)-9H-purin-2-amine;
tert-Butyl 4-(9-cyclopropyl-8-(pyridin-4-yl)-9H-purin-2-ylamino)phenethylcarbamate;
9-Ethyl-N-(4-fluoro-3-methoxyphenyl)-8-(2-(methylamino)pyrimidin-4-yl)-9H-purin-2-amine;
9-Cyclopropyl-N-(3-fluorophenyl)-8-(2-(methylamino)pyrimidin-4-yl)-9H-purin-2-amine;
N-(4-(9-Ethyl-8-(pyridin-4-yl)-9H-purin-2-ylamino)benzyl)-N-methylacetamide;
8-(2-Aminopyrimidin-4-yl)-9-ethyl-N-(4-ethylphenyl)-9H-purin-2-amine;
9-Methyl-N-(3-((4-methylpiperazin-1-yl)methyl)phenyl)-8-(pyridin-4-yl)-9H-purin-2-amine;
9-Cyclopropyl-8-(pyridin-4-yl)-N-(3-(trifluoromethoxy)phenyl)-9H-purin-2-amine;
9-Ethyl-N-(3-(2-morpholinoethoxy)phenyl)-8-(pyridin-4-yl)-9H-purin-2-amine;
9-Methyl-N-(4-(piperazin-1-ylmethyl)phenyl)-8-(pyridin-4-yl)-9H-purin-2-amine;
N-(3-(2-(Cyclopentylamino)ethyl)phenyl)-9-ethyl-8-(pyridin-4-yl)-9H-purin-2-amine;
N-(3-(Aminomethyl)phenyl)-9-cyclopropyl-8-(pyridin-4-yl)-9H-purin-2-amine;
9-Isopropyl-N-(3-methoxyphenyl)-8-(2-(methylamino)pyrimidin-4-yl)-9H-purin-2-amine;
N-(8-(2-Aminopyrimidin-4-yl)-9-cyclopropyl-9H-purin-2-yl)quinolin-6-amine;
N-(3-Chlorophenyl)-9-cyclopropyl-8-(2-(methylamino)pyrimidin-4-yl)-9H-purin-2-amine;
9-Cyclopropyl-N-(4-((methylamino)methyl)phenyl)-8-(pyridin-4-yl)-9H-purin-2-amine;
9-Cyclopropyl-N-phenethyl-8-(pyridin-4-yl)-9H-purin-2-amine;
8-(2-Aminopyrimidin-4-yl)-9-ethyl-N-(3-fluorophenyl)-9H-purin-2-amine;
8-(2-Aminopyrimidin-4-yl)-9-isopropyl-N-(3-methoxyphenyl)-9H-purin-2-amine;
9-Cyclopropyl-N-(3-methoxyphenyl)-8-(2-(methylamino)pyrimidin-4-yl)-9H-purin-2-amine;
9-Ethyl-N-(3-(2-methoxyethoxy)phenyl)-8-(pyridin-4-yl)-9H-purin-2-amine;
N-(3,4-Difluorophenyl)-9-ethyl-8-(pyridin-4-yl)-9H-purin-2-amine;
8-(2-Aminopyrimidin-4-yl)-N-(2,4-dimethylphenyl)-9-ethyl-9H-purin-2-amine;
9-Ethyl-N-(3-(2-(ethylamino)ethyl)phenyl)-8-(pyridin-4-yl)-9H-purin-2-amine;
9-Methyl-N-(3-(morpholinomethyl)phenyl)-8-(pyridin-4-yl)-9H-purin-2-amine;
9-Methyl-N-(4-(2-(piperidin-1-yl)ethyl)phenyl)-8-(pyridin-4-yl)-9H-purin-2-amine;
N-(4-(Aminomethyl)phenyl)-9-cyclopropyl-8-(pyridin-4-yl)-9H-purin-2-amine;
8-(2-Aminopyrimidin-4-yl)-9-cyclopropyl-N-(4-fluorophenyl)-9H-purin-2-amine;
8-(2-Aminopyrimidin-4-yl)-9-ethyl-N-o-tolyl-9H-purin-2-amine;
8-(2-Aminopyrimidin-4-yl)-9-ethyl-N-(3-ethylphenyl)-9H-purin-2-amine;
N-(8-(2-Aminopyrimidin-4-yl)-9-cyclopropyl-9H-purin-2-yl)quinolin-8-amine;
8-(2-Aminopyrimidin-4-yl)-N-(4-fluorophenyl)-9-(2,2,2-trifluoroethyl)-9H-purin-2-amine;
N-(4-(2-Aminoethyl)phenyl)-9-methyl-8-(pyridin-4-yl)-9H-purin-2-amine;
9-Ethyl-N-(3-ethylphenyl)-8-(pyridin-4-yl)-9H-purin-2-amine;
9-Isopropyl-N-(3-methoxyphenyl)-8-(pyrimidin-4-yl)-9H-purin-2-amine;
N-(4-(2-(Cyclopropylamino)ethyl)phenyl)-9-ethyl-8-(pyridin-4-yl)-9H-purin-2-amine;
N-(8-(2-Aminopyrimidin-4-yl)-9-cyclopropyl-9H-purin-2-yl)isoquinolin-5-amine;
N-(3-(2-(Dimethylamino)ethyl)phenyl)-9-ethyl-8-(pyridin-4-yl)-9H-purin-2-amine;
8-(2-Aminopyrimidin-4-yl)-9-cyclopropyl-N-(3-methoxyphenyl)-9H-purin-2-amine;
9-Ethyl-N-(3-(2-(piperidin-1-yl)ethoxy)phenyl)-8-(pyridin-4-yl)-9H-purin-2-amine;
9-Methyl-N-(4-((methylamino)methyl)phenyl)-8-(pyridin-4-yl)-9H-purin-2-amine;
8-(2-Aminopyridin-4-yl)-9-ethyl-N-(3-ethylphenyl)-9H-purin-2-amine;
8-(2-Aminopyrimidin-4-yl)-9-ethyl-N-p-tolyl-9H-purin-2-amine;

9-Cyclopropyl-N-(3,4-dimethoxyphenyl)-8-(pyridin-4-yl)-9H-purin-2-amine;
9-Methyl-8-(pyridin-4-yl)-N-(4-(2-(pyrrolidin-1-yl)ethyl)phenyl)-9H-purin-2-amine;
9-Ethyl-N-(4-fluorophenyl)-8-(pyridin-4-yl)-9H-purin-2-amine;
8-(2-Aminopyrimidin-4-yl)-9-ethyl-N-(3-fluoro-2-methylphenyl)-9H-purin-2-amine;
9-Methyl-8-(pyridin-4-yl)-N-(3-(2-(pyrrolidin-1-yl)ethyl)phenyl)-9H-purin-2-amine;
N-(3-(Aminomethyl)phenyl)-9-methyl-8-(pyridin-4-yl)-9H-purin-2-amine;
9-Cyclopropyl-N-(4-fluorophenyl)-8-(pyridin-4-yl)-9H-purin-2-amine;
N-(4-Methylbenzyl)-9-cyclopropyl-8-(pyridin-4-yl)-9H-purin-2-amine;
N-(4-(9-Ethyl-8-(pyridin-4-yl)-9H-purin-2-ylamino)benzyl)acetamide;
N-(3-(9-Methyl-8-(pyridin-4-yl)-9H-purin-2-ylamino)benzyl)acetamide;
N-(4-(Aminomethyl)phenyl)-9-methyl-8-(pyridin-4-yl)-9H-purin-2-amine;
8-(2-Aminopyrimidin-4-yl)-9-cyclopropyl-N-(2-(thiophen-2-yl)ethyl)-9H-purin-2-amine;
8-(2-Aminopyridin-4-yl)-9-ethyl-N-(4-fluorophenyl)-9H-purin-2-amine;
N-(3-(2-(Dimethylamino)ethoxy)phenyl)-9-ethyl-8-(pyridin-4-yl)-9H-purin-2-amine;
9-Methyl-N-(4-(piperidin-1-ylmethyl)phenyl)-8-(pyridin-4-yl)-9H-purin-2-amine;
8-(2-Aminopyrimidin-4-yl)-N-(3,5-difluorophenyl)-9-ethyl-9H-purin-2-amine;
N-(4-(2-(Dimethylamino)ethyl)phenyl)-9-ethyl-8-(pyridin-4-yl)-9H-purin-2-amine;
9-Cyclopropyl-8-(2-(methylamino)pyrimidin-4-yl)-N-phenyl-9H-purin-2-amine;
8-(2-Aminopyrimidin-4-yl)-N-(2,5-difluorophenyl)-9-ethyl-9H-purin-2-amine;
9-Cyclopropyl-N-(3-(2-morpholinoethoxy)phenyl)-8-(pyridin-4-yl)-9H-purin-2-amine;
8-(2-Aminopyrimidin-4-yl)-N-(3,4-difluorophenyl)-9-ethyl-9H-purin-2-amine;
8-(2-Aminopyrimidin-4-yl)-N-(2,3-difluorophenyl)-9-ethyl-9H-purin-2-amine;
8-(2-Aminopyrimidin-4-yl)-N-(4-fluorophenyl)-9-methyl-9H-purin-2-amine;
tert-Butyl 4-(9-cyclopropyl-8-(pyridin-4-yl)-9H-purin-2-ylamino)benzylcarbamate;
9-Cyclopropyl-N-(2,4-dimethoxyphenyl)-8-(pyridin-4-yl)-9H-purin-2-amine;
9-Methyl-N-(3-(2-(piperidin-1-yl)ethyl)phenyl)-8-(pyridin-4-yl)-9H-purin-2-amine;
N-(4-(2-Aminoethyl)phenyl)-9-ethyl-8-(pyridin-4-yl)-9H-purin-2-amine;
9-Ethyl-N-(3-((ethylamino)methyl)phenyl)-8-(pyridin-4-yl)-9H-purin-2-amine;
8-(2-Aminopyrimidin-4-yl)-9-cyclopropyl-N-m-tolyl-9H-purin-2-amine;
N-(4-(9-Methyl-8-(pyridin-4-yl)-9H-purin-2-ylamino)phenethyl)acetamide;
8-(2-Aminopyrimidin-4-yl)-N-(3,4-dimethylphenyl)-9-ethyl-9H-purin-2-amine;
N-(4-Fluorophenyl)-8-(2-(methylamino)pyrimidin-4-yl)-9-(2,2,2-trifluoroethyl)-9H-purin-2-amine;
N-(3-(9-Cyclopropyl-8-(pyridin-4-yl)-9H-purin-2-ylamino)benzyl)acetamide;
(4-(2-(4-Fluorophenylamino)-9-methyl-9H-purin-8-yl)pyridin-2-yl)methanol;
N-(4-((Cyclopentylamino)methyl)phenyl)-9-ethyl-8-(pyridin-4-yl)-9H-purin-2-amine;
8-(2-Aminopyrimidin-4-yl)-N-(2-chloro-5-fluorophenyl)-9-cyclopropyl-9H-purin-2-amine;
N-(4-Fluorophenyl)-9-methyl-8-(2-(methylamino)pyrimidin-4-yl)-9H-purin-2-amine;
9-Cyclopropyl-N-(3-methoxyphenyl)-8-(pyrimidin-4-yl)-9H-purin-2-amine;
$N^1$-(8-(2-Aminopyrimidin-4-yl)-9-cyclopropyl-9H-purin-2-yl)-$N^4$,$N^4$-dimethylbenzene-1,4-diamine;
9-Methyl-8-(pyridin-4-yl)-N-(2-(thiophen-2-yl)ethyl)-9H-purin-2-amine;
8-(2-Aminopyrimidin-4-yl)-N-(2,3-dimethylphenyl)-9-ethyl-9H-purin-2-amine;
N-(2,3-Dihydrobenzo[b][1,4]dioxin-6-yl)-9-ethyl-8-(pyridin-4-yl)-9H-purin-2-amine;
3-(2-(3-Methoxyphenylamino)-8-(pyrimidin-4-yl)-9H-purin-9-yl)propanenitrile;
9-Ethyl-N-(3-ethylphenyl)-8-(2-(methylamino)pyrimidin-4-yl)-9H-purin-2-amine;
9-Ethyl-N-(4-((ethylamino)methyl)phenyl)-8-(pyridin-4-yl)-9H-purin-2-amine;
9-Methyl-N-(4-(2-morpholinoethyl)phenyl)-8-(pyridin-4-yl)-9H-purin-2-amine;
8-(2-Chloropyridin-4-yl)-9-cyclopropyl-N-phenyl-9H-purin-2-amine;
9-Cyclopropyl-8-(1-methyl-1H-pyrrol-2-yl)-N-(2-(thiophen-2-yl)ethyl)-9H-purin-2-amine;
8-(2-Aminopyrimidin-4-yl)-9-ethyl-N-(3-fluoro-4-methylphenyl)-9H-purin-2-amine;
9-Methyl-N-(4-((4-methylpiperazin-1-yl)methyl)phenyl)-8-(pyridin-4-yl)-9H-purin-2-amine;
8-(2-Aminopyrimidin-4-yl)-N-(3,5-dimethylphenyl)-9-ethyl-9H-purin-2-amine;
9-Methyl-N-(4-(morpholinomethyl)phenyl)-8-(pyridin-4-yl)-9H-purin-2-amine;
N-(3-((Dimethylamino)methyl)phenyl)-9-ethyl-8-(pyridin-4-yl)-9H-purin-2-amine;
8-(2-Aminopyridin-4-yl)-9-ethyl-N-(4-fluoro-3-methoxyphenyl)-9H-purin-2-amine;
8-(2-Aminopyrimidin-4-yl)-N-(3-chlorophenyl)-9-ethyl-9H-purin-2-amine;
N-(4-(9-Methyl-8-(pyridin-4-yl)-9H-purin-2-ylamino)phenethyl)-N-methylacetamide;
8-(2-Aminopyrimidin-4-yl)-N-(4-chloro-2-fluorophenyl)-9-cyclopropyl-9H-purin-2-amine;
9-Cyclopropyl-N-(4-(2-(methylamino)ethyl)phenyl)-8-(pyridin-4-yl)-9H-purin-2-amine;
9-Cyclopropyl-N-(2-fluorophenyl)-8-(pyridin-4-yl)-9H-purin-2-amine;
9-Ethyl-N-(4-(2-(ethylamino)ethyl)phenyl)-8-(pyridin-4-yl)-9H-purin-2-amine;
9-Ethyl-N-(4-((isopropylamino)methyl)phenyl)-8-(pyridin-4-yl)-9H-purin-2-amine;
9-Methyl-N-(4-(2-(4-methylpiperazin-1-yl)ethyl)phenyl)-8-(pyridin-4-yl)-9H-purin-2-amine;
9-Ethyl-N-(3-fluorophenyl)-8-(2-(methylamino)pyrimidin-4-yl)-9H-purin-2-amine;
N-(4-Fluorophenyl)-9-methyl-8-(pyridin-4-yl)-9H-purin-2-amine;
9-Cyclopropyl-N-phenyl-8-(pyridin-4-yl)-9H-purin-2-amine;
8-(2-Aminopyrimidin-4-yl)-N-(2,3-dihydro-1H-inden-5-yl)-9-ethyl-9H-purin-2-amine;

9-Ethyl-N-(4-(2-methoxyethoxy)phenyl)-8-(pyridin-4-yl)-9H-purin-2-amine;
N-(3-(Aminomethyl)phenyl)-9-ethyl-8-(pyridin-4-yl)-9H-purin-2-amine;
N-(3-((Cyclopentylamino)methyl)phenyl)-9-ethyl-8-(pyridin-4-yl)-9H-purin-2-amine;
9-Methyl-N-(4-(2-(methylamino)ethyl)phenyl)-8-(pyridin-4-yl)-9H-purin-2-amine;
3-Ethyl-N-(4-((methylamino)methyl)phenyl)-2-(pyridin-4-yl)-3H-imidazo[4,5-b]pyridin-5-amine;
N-(4-(2-(Cyclopentylamino)ethyl)phenyl)-9-ethyl-8-(pyridin-4-yl)-9H-purin-2-amine;
9-Methyl-N-(3-(2-(piperazin-1-yl)ethyl)phenyl)-8-(pyridin-4-yl)-9H-purin-2-amine;
N-(2-Fluorophenethyl)-9-cyclopropyl-8-(pyridin-4-yl)-9H-purin-2-amine;
9-Cyclopropyl-N-(4-fluorophenyl)-8-(2-(methylamino)pyrimidin-4-yl)-9H-purin-2-amine;
9-Cyclopropyl-8-(pyridin-4-yl)-N-(3,4,5-trimethoxyphenyl)-9H-purin-2-amine;
9-Methyl-8-(pyridin-4-yl)-N-(4-(pyrrolidin-1-ylmethyl)phenyl)-9H-purin-2-amine;
9-Cyclopropyl-N-(3-ethylphenyl)-8-(2-(methylamino)pyrimidin-4-yl)-9H-purin-2-amine;
8-(6-Aminopyridin-3-yl)-9-ethyl-N-(4-fluorophenyl)-9H-purin-2-amine;
$N^1$-(8-(2-Aminopyrimidin-4-yl)-9-cyclopropyl-9H-purin-2-yl)-$N^3$,$N^3$-dimethylbenzene-1,3-diamine;
N-(3-((Cyclopropylamino)methyl)phenyl)-9-ethyl-8-(pyridin-4-yl)-9H-purin-2-amine;
8-(2-Aminopyrimidin-4-yl)-N-(2,4-difluorophenyl)-9-ethyl-9H-purin-2-amine;
9-Cyclopropyl-N-(3,5-dimethoxyphenyl)-8-(pyridin-4-yl)-9H-purin-2-amine;
N-(4-(9-Cyclopropyl-8-(pyridin-4-yl)-9H-purin-2-ylamino)phenethyl)acetamide;
N-(4-(9-Ethyl-8-(pyridin-4-yl)-9H-purin-2-ylamino)phenethyl)-N-methylacetamide;
N-(4-(9-Methyl-8-(pyridin-4-yl)-9H-purin-2-ylamino)benzyl)acetamide;
9-Ethyl-N-(4-(2-(piperidin-1-yl)ethoxy)phenyl)-8-(pyridin-4-yl)-9H-purin-2-amine;
N-(4-(2-Methoxyethoxy)phenyl)-9-methyl-8-(pyridin-4-yl)-9H-purin-2-amine;
8-(2-Chloropyridin-4-yl)-9-isopropyl-N-(3-methoxyphenyl)-9H-purin-2-amine;
8-(2-Aminopyridin-4-yl)-9-isopropyl-N-(3-methoxyphenyl)-9H-purin-2-amine;
9-Ethyl-N-(4-(2-(methylamino)ethyl)phenyl)-8-(pyridin-4-yl)-9H-purin-2-amine;
9-Ethyl-N-(4-(2-morpholinoethoxy)phenyl)-8-(pyridin-4-yl)-9H-purin-2-amine;
8-(2-Aminopyridin-4-yl)-N-(3,4-difluorophenyl)-9-ethyl-9H-purin-2-amine;
8-(2-Aminopyrimidin-4-yl)-N-(2-chlorophenyl)-9-ethyl-9H-purin-2-amine;
9-Methyl-N-(3-(piperidin-1-ylmethyl)phenyl)-8-(pyridin-4-yl)-9H-purin-2-amine;
8-(6-Aminopyridin-3-yl)-9-ethyl-N-(3-ethylphenyl)-9H-purin-2-amine;
N-(4-(9-Cyclopropyl-8-(pyridin-4-yl)-9H-purin-2-ylamino)benzyl)-N-methylacetamide;
9-Cyclopropyl-8-(pyridin-3-yl)-N-(2-(thiophen-2-yl)ethyl)-9H-purin-2-amine;
N-(2,2-Dimethylbenzo[d][1,3]dioxol-5-yl)-9-ethyl-8-(pyridin-4-yl)-9H-purin-2-amine;
N-(4-(9-Cyclopropyl-8-(pyridin-4-yl)-9H-purin-2-ylamino)phenethyl)-N-methylacetamide;
9-Cyclopropyl-8-(thiazol-2-yl)-N-(2-(thiophen-2-yl)ethyl)-9H-purin-2-amine;
8-(2-Aminopyrimidin-4-yl)-N-(2,6-difluorophenyl)-9-ethyl-9H-purin-2-amine;
8-(2-Aminopyrimidin-4-yl)-9-ethyl-N-(2-fluoro-4-methylphenyl)-9H-purin-2-amine;
8-(2-Aminopyrimidin-4-yl)-N-(4-chlorophenyl)-9-ethyl-9H-purin-2-amine;
8-(2-Aminopyrimidin-4-yl)-N-(3-chloro-4-fluorophenyl)-9-cyclopropyl-9H-purin-2-amine;
9-Methyl-N-(3-(2-(4-methylpiperazin-1-yl)ethyl)phenyl)-8-(pyridin-4-yl)-9H-purin-2-amine;
9-Ethyl-N-(3-((isopropylamino)methyl)phenyl)-8-(pyridin-4-yl)-9H-purin-2-amine;
N-(8-(2-Aminopyrimidin-4-yl)-9-cyclopropyl-9H-purin-2-yl)quinolin-5-amine;
N-(2-(4-(9-Methyl-8-(pyridin-4-yl)-9H-purin-2-ylamino)phenoxy)ethyl)acetamide;
8-(2-Chloropyridin-4-yl)-9-cyclopropyl-N-(3-methoxyphenyl)-9H-purin-2-amine;
8-(2-Aminopyrimidin-4-yl)-N-(2,5-dimethylphenyl)-9-ethyl-9H-purin-2-amine;
8-(2-Aminopyrimidin-4-yl)-9-ethyl-N-(4-fluoro-2-methylphenyl)-9H-purin-2-amine;
N-(4-((Cyclopropylamino)methyl)phenyl)-9-ethyl-8-(pyridin-4-yl)-9H-purin-2-amine;
8-(2-Aminopyrimidin-4-yl)-9-ethyl-N-(2-ethylphenyl)-9H-purin-2-amine;
N-(4-Methoxyphenyl)-9-methyl-8-(pyridin-4-yl)-9H-purin-2-amine;
9-Cyclopropyl-8-(pyrimidin-4-yl)-N-(2-(thiophen-2-yl)ethyl)-9H-purin-2-amine;
8-(2-Aminopyrimidin-4-yl)-9-ethyl-N-(4-fluoro-3-methoxyphenyl)-9H-purin-2-amine;
9-Cyclopropyl-8-(1-methyl-1H-imidazol-5-yl)-N-(2-(thiophen-2-yl)ethyl)-9H-purin-2-amine;
N-(Benzo[d][1,3]dioxol-5-yl)-9-cyclopropyl-8-(pyridin-4-yl)-9H-purin-2-amine;
N-(4-(2-(Dimethylamino)ethoxy)phenyl)-9-ethyl-8-(pyridin-4-yl)-9H-purin-2-amine;
N-(Benzo[d]thiazol-6-yl)-9-cyclopropyl-8-(pyridin-4-yl)-9H-purin-2-amine;
9-Ethyl-N-(4-fluoro-3-methoxyphenyl)-8-(pyridin-4-yl)-9H-purin-2-amine;
8-(2-Aminopyrimidin-4-yl)-N-(2,3-dihydro-1H-inden-4-yl)-9-ethyl-9H-purin-2-amine;
N-(3-(2-(Cyclopropylamino)ethyl)phenyl)-9-ethyl-8-(pyridin-4-yl)-9H-purin-2-amine;
9-Ethyl-N-(4-fluorophenyl)-8-(2-(methylamino)pyrimidin-4-yl)-9H-purin-2-amine;
9-Ethyl-N-(4-(2-(isopropylamino)ethyl)phenyl)-8-(pyridin-4-yl)-9H-purin-2-amine;
8-(2-Aminopyrimidin-4-yl)-N-(3-chloro-2-fluorophenyl)-9-cyclopropyl-9H-purin-2-amine;
3-(8-(2-Aminopyrimidin-4-yl)-2-(3-methoxyphenylamino)-9H-purin-9-yl)propanenitrile;
8-(2-Aminopyridin-4-yl)-N-(4-fluorophenyl)-9-methyl-9H-purin-2-amine;
N-(4-Fluorophenyl)-8-(pyridin-4-yl)-9H-purin-2-amine;
N-(4-Chlorophenyl)-9-cyclopropyl-8-(pyridin-4-yl)-9H-purin-2-amine;
8-(2-Aminopyrimidin-4-yl)-9-cyclopropyl-N-(3-ethylphenyl)-9H-purin-2-amine;
9-Ethyl-N-(4-((methylamino)methyl)phenyl)-8-(pyridin-4-yl)-9H-purin-2-amine;

N-(4-Fluorophenyl)-8-(pyridin-4-yl)-9-(2,2,2-trifluoroethyl)-9H-purin-2-amine;
N-(3-(9-Ethyl-8-(pyridin-4-yl)-9H-purin-2-ylamino)benzyl)acetamide;
9-Methyl-8-(pyridin-4-yl)-N-(3-(pyrrolidin-1-ylmethyl)phenyl) -9H-purin-2-amine;
8-(2-Aminopyrimidin-4-yl)-9-ethyl-N-(5-fluoro-2-methylphenyl)-9H-purin-2-amine;
8-(2-Chloropyridin-4-yl)-9-cyclopropyl-N-(2-(thiophen-2-yl)ethyl)-9H-purin-2-amine;
8-(2-Aminopyrimidin-4-yl)-N-(5-chloro-2-fluorophenyl)-9-cyclopropyl-9H-purin-2-amine;
9-Methyl-N-(3-(2-morpholinoethyl)phenyl)-8-(pyridin-4-yl)-9H-purin-2-amine;
9-Cyclopropyl-N-(2-methoxyphenyl)-8-(pyridin-4-yl)-9H-purin-2-amine;
8-(2-Chloropyridin-4-yl)-9-ethyl-N-(3-ethylphenyl)-9H-purin-2-amine;
9-Cyclopropyl-N-(3-methoxyphenyl)-8-(pyridin-4-yl)-9H-purin-2-amine;
N-(2-Methoxyphenethyl)-9-cyclopropyl-8-(pyridin-4-yl)-9H-purin -2-amine;
Ethyl-4-(2-(4-fluorophenylamino)-9-methyl-9H-purin-8-yl) picolinate;
8-(2-Aminopyrimidin-4-yl)-N-(2-chloro-4-fluorophenyl)-9-cyclopropyl-9H-purin-2-amine;
N-(4-(2-Aminoethyl)phenyl)-9-cyclopropyl-8-(pyridin-4-yl)-9H-purin-2-amine;
N-Cyclopentyl-9-cyclopropyl-8-(pyridin-4-yl)-9H-purin-2-amine;
8-(2-Aminopyrimidin-4-yl)-9-cyclopropyl-N-(3-fluorophenyl)-9H-purin-2-amine;
9-Cyclopropyl-8-(pyridin-4-yl)-N-(2-(thiophen-2-yl)ethyl)-9H-purin-2-amine;
8-(2-Aminopyridin-4-yl)-9-cyclopropyl-N-phenyl-9H-purin-2-amine;
8-(2-Aminopyrimidin-4-yl)-N-(3-chlorophenyl)-9-cyclopropyl-9H-purin-2-amine;
N-(4-(Aminomethyl)phenyl)-9-ethyl-8-(pyridin-4-yl)-9H-purin-2-amine;
N-(4-(9-Methyl-8-(pyridin-4-yl)-9H-purin-2-ylamino)benzyl)-2,2,2-trifluoroacetamide;
9-Ethyl-N-(3-(2-(isopropylamino)ethyl)phenyl)-8-(pyridin-4-yl) -9H-purin-2-amine;
N-(3,4-Difluorophenyl)-9-ethyl-8-(2-(methylamino)pyrimidin-4-yl)-9H-purin-2-amine;
9-Methyl-N-(3-(piperazin-1-ylmethyl)phenyl)-8-(pyridin-4-yl)-9H-purin-2-amine;
9-Cyclopropyl-N-isobutyl-8-(pyridin-4-yl)-9H-purin-2-amine;
9-Ethyl-8-(2-(methylamino)pyrimidin-4-yl)-N-m-tolyl-9H-purin-2-amine;
8-(2-Aminopyrimidin-4-yl)-9-cyclopropyl-N-phenyl-9H-purin-2-amine;
9-Cyclopropyl-8-(1H-pyrrol-2-yl)-N-(2-(thiophen-2-yl)ethyl)-9H-purin-2-amine;
8-(2-Aminopyrimidin-4-yl)-9-ethyl-N-(4-fluorophenyl)-9H -purin-2-amine;
8-(2-Aminopyrimidin-4-yl)-9-ethyl-N-m-tolyl-9H-purin-2-amine;
9-Methyl-N-(4-(2-(piperazin-1-yl)ethyl)phenyl)-8-(pyridin-4-yl)-9H-purin-2-amine;
8-(Pyridin-4-yl)-N-(2-(thiophen-2-yl)ethyl)-9H-purin-2-amine;
N-(4-((Dimethylamino)methyl)phenyl)-9-ethyl-8-(pyridin-4-yl)-9H-purin-2-amine;
9-Cyclopropyl-N-(4-methoxyphenyl)-8-(pyridin-4-yl)-9H-purin-2-amine;
8-(2-Aminopyrimidin-4-yl)-9-ethyl-N-(5,6,7,8-tetrahydronaphthalen-1-yl)-9H-purin-2-amine.

The compositions may be administered alone or in combination with another agent, drug, or hormone, and may be administered by any number of acceptable routes. Pharmaceutical compositions suitable for the use in the invention include compositions wherein the active ingredients are contained in an effective amount to achieve the intended purpose. The determination of an effective dose is well within the capability of those skilled in the art. In addition to type 2 diabetes and metabolic disorders like obesity, such pharmaceutical composition may be used to treat cachexia, osteoarthritis, gallstones, sleep apnea, neurodegenerative disorders, and cancer.

Abbreviations: The following abbreviations and terms have the indicated meaning throughout, unless otherwise stated:
AcOH—Acetic acid
C—Carbon
$CDCl_3$—Deuterated chloroform
$CD_3OD$—Deuterated methanol
$(CD_3)_2SO$—Deuterated dimethyl sulfoxide
δ—NMR chemical shift referenced to tetramethylsilane
DMA—N,N-dimethylacetamide
DMSO—Dimethyl sulfoxide
Et—Ethyl
$Et_3N$—Triethylamine
EtOAc—Ethyl acetate
ESI—Electrospray ionization
$^1H$ NMR—Proton Nuclear Magnetic Resonance
h—hours
i—iso
$iPr_2NEt$—Diisopropylethylamine
m-—meta
MeOH—methanol=$CH_3OH$
MHz—Megahertz
min—minutes
N—nitrogen
NMR—Nuclear Magnetic Resonance
p-—para
Ph—Phenyl
r.t.—room temperature
sat.—saturated
TFA—trifluoro acetic acid
THF—tetrahydrofuran
Biological Methods
In vitro MNK1 Kinase Assay (HTRF):

MNK1 inhibitor activity was determined using recombinant full length human MNK1 with an N-terminal GST-tag (glutathione-5-transferase; GST-MNK2A). The protein construct was expressed in Sf9 cells and purified using a Glutathione Sepharose 4 FF column. The in-vitro kinase assay used for MNK1 activity was a homogeneous time resolved fluorescence (HTRF) assay. The assay uses a biotinylated 18 amino acids peptide sequence from the transcription factor CREB (biotin-AGAGKRREILSRRPSYRK purchased from NeoMPS). The amount of phosphorylated CREB-peptide was quantified by HTRF employing an europium ($Eu^{3+}$) cryptate-conjugated phosphospecific antibody (CREB Ser 133 from Cisbio International) as donor and streptavidin labelled with XL665 (cross-linked allophycocyanin; StrepX-Lent from Cisbio International) as acceptor. The kinase reaction mixture consisted of 0.63 nM GST-MNK1, 100 nM CREB peptide, 7.2 µM ATP and 0.05% Bovine Serum Albumine (BSA) in a buffer containing 50 mM HEPES pH 7.6, 0.25 mM MnCl$_2$, 1 mM dithiothreitol (DTT) and 0.001% Tween 20. The kinase reaction mixture was incubated for 30 minutes at room temperature. The kinase reaction was terminated by addition of the Eu$^3$ cryptate-conjugated phospho-specific antibody (CREB Ser 133) containing 0.6 M potassium fluoride. The final concentration 0.3 M potassium fluoride stops the reaction. The detection step was performed by adding the streptavidin labelled XL665. The final concentrations of donor and acceptor were 0.2 nM and 42 nM, respectively. The buffer used for the detection reagents was 50 mM Hepes pH 7.0, 0.6 M potassium fluoride and 0.1% BSA. The detection mixture was incubated for 1 hour at room temperature before analysis with a plate reader (Wallac Victor V) for HTRF readout. The excitation wave length used was 340 nm, while the emission for the Eu$^{3+}$cryptate and the acceptor XL665 was detected at 615 nm and 665 nm, respectively. The HTRF read-out is the ratio of the emission at 665 nm and the emission at 615 nm, since this ratio is independent of the optical characteristics of the media at the excitation wavelength. For IC$_{50}$ determinations, test compounds were dissolved at 10 mM in 100% DMSO. The compounds were added in the kinase reaction mixture by 1:100 dilutions and typically assayed over an eleven point dilution range with each point in triplicate.

The results indicated that the MNK1 to MNK2a activity ratios for the compounds ranged from 11 to 0.1, i.e. about 10:1 to 1:10. The compounds of the present invention are thus believed to generally exhibit an MNK1 activity which is 1:20 to 20:1 of that for MNK2a.

Materials

Mnk2a inhibitory activity was determined using recombinant full length human Mnk2a with an N-terminal GST-tag (glutathione-S-transferase; GST-Mnk2A). The protein construct was expressed in Sf9 cells and purified using a Glutathione Sepharose FF column followed by a gel filtration column. Reagents for the homogeneous time-resolved fluorescence assay included biotinylated CREB peptide (biotinyl-Ala-Gly-Ala-Gly-Lys-Arg-Arg-Glu-Ile-Leu-Ser-Arg-Arg-Pro-Ser-Tyr-Arg-Lys; NeoMPS, Strasbourg, France), Europium cryptate-labeled anti-phospho-CREB (Ser133) antibody (CisUS, Bedford, Mass.), and StreptXLent (CisUS). Buffer components included HEPES (BioWhittaker/Cambrex, Walkersville, Md.) manganese chloride, bovine serum albumin (BSA), adenosine triphosphate, dithiothreitol, potassium fluoride, and dimethylsulfoxide (DMSO; Sigma-Aldrich, St. Louis, Mo.). Assays were performed in white 1536-well plates (Nunc).

FLT-3 inhibitory activity was determined using recombinant cytoplasmic domain (amino acids 564-958) human FLT-3 with a C-terminal histidine tag, expressed in insect cells and activated in vitro by autophosphorylation (Invitrogen, Carlsbad, Calif.). Reagents for the homogeneous time-resolved fluorescence assay included biotinylated poly (Glu, Ala, Tyr) peptide (Sigma-Aldrich, St. Louis, Mo.), Europium-labeled anti-phospho-tyrosine antibody (PT66, PerkinElmer, Waltham, Mass.), and StreptXLent (CisUS, Bedford, Mass.). Buffer components included HEPES (BioWhittaker/Cambrex, Walkersville, Md.), magnesium chloride, sodium orthovanadate, bovine serum albumin (BSA), adenosine triphosphate (ATP), dithiothreitol, Triton X-100, ethylenediaminetetraacetic acid (EDTA), and dimethylsulfoxide (DMSO; Sigma-Aldrich, St. Louis, Mo.). Assays were performed in black 384-well plates (Corning-Costar).

Mnk2 Methods:

Mnk2: Test compounds were serially diluted in 100% DMSO to 50× final concentration, prior to 25-fold dilution into 2× concentrated ATP/CREB substrate in assay buffer (50 mM HEPES, pH 7.6, 0.25 mM MnCl$_2$, 1 mM dithiothreitol, 0.05% BSA). 2 µL of the compound/ATP/CREB substrate solution was then combined with 2 µL enzyme in assay wells. Final concentrations of reagents were 160 nM CREB peptide, 0.5 µM ATP, and 0.06 nM Mnk2a enzyme, 2% DMSO. The kinase reaction was carried out for thirty minutes at 25° C. Detection reagents (2 µL each) in detection buffer (50 mM HEPES, pH 7.0, 0.6 M KF, 0.1% BSA) were added as working solutions containing 2 µg/mL Strept XLent (lot #8) or anti-phospho-CREB antibody cryptate (0.14 µg/mL, lot #4). 4-16 hours after addition of detection reagents, time-resolved fluorescence was measured at two wavelength combinations (340/671 nm and 340/618 nm) by imaging in the ViewLux (Perkin Elmer, Boston, Mass. Data were fit using a variable slope sigmoidal dose-response equation (GraphPad Prism, GraphPad Software, San Diego, Calif.).

FLT-3 Methods:

FLT-3: Test compounds were serially diluted in 100% DMSO to 100× final concentration, prior to dilution into reaction mixes. The kinase reaction was carried out for one hour in the dark at 25° C. in assay buffer (50 mM HEPES, pH 7.6, 0.2 mM Na$_3$VO$_4$, 10 mM MgCl$_2$, 1 mM dithiothreitol, 0.01% BSA, 0.01% Triton X-100), with final concentrations of 0.12 µg/ml FLT-3, 1.4 µg/ml biotinylated poly (Glu, Ala, Tyr), 3 µM ATP, and 1% DMSO. The kinase reaction volume was 21 µL (7 µL test compound in buffer/3.3% DMSO, 7 µL enzyme, and 7 µL biotin-poly (Glu, Ala, Tyr)/ATP mix). For detection, 10 µL of a working solution of 2 µg/mL Strept XLent/0.8 µg/mL Eu-PT66 in 50 mM HEPES, pH 7.6, 12 mM EDTA, 0.05% BSA was added. After incubation for one hour in the dark at 25° C., time-resolved fluorescence was measured in the Victor V (Perkin Elmer, Waltham, Mass.) at 340 nm$_{ex}$/665 nm$_{em}$ and 340 nm$_{ex}$/615 nm$_{em}$. Data were fit using a variable slope sigmoidal dose-response equation (GraphPad Prism, GraphPad Software, San Diego, Calif.). Under these conditions, staurosporine inhibited FLT-3 with an IC$_{50}$ value of 0.5 nM.

EXAMPLES

Example 1

Synthesis of Aminopurine Derivatives

Compounds of formula I can be synthesized by means of conventional organic synthesis executable by those skilled in the art. The illustration of examples, but not the limitation, of the synthesis of compounds of formula I is detailed in Scheme 1, herein below:

Scheme 1:

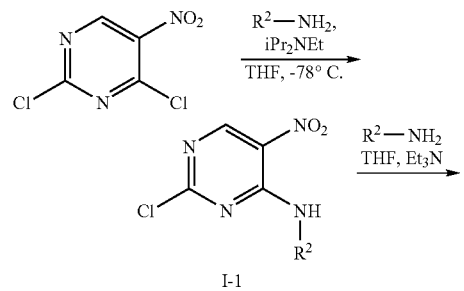

-continued

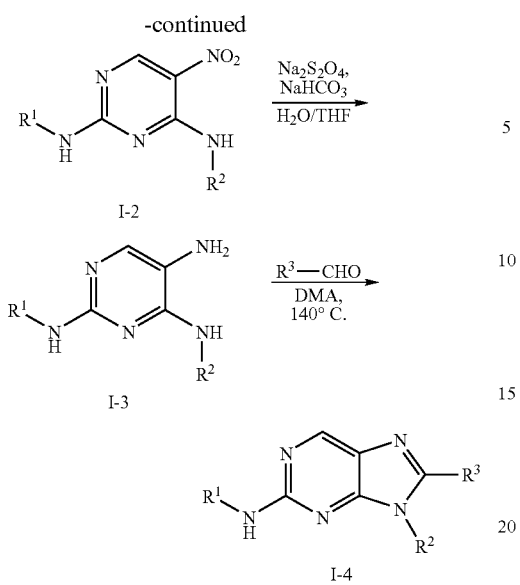

Compounds of formula I can be synthesized in four steps from commercially available 2,4-dichloro-5-nitropyrimidine (Scheme 1). Initial N-arylation of a primary amine ($R^2$—$NH_2$) with 2,4-dichloro-5-nitropyrimidine provides a mixture (typically a 10:1 ratio) of regioisomers which can be readily separated by flash chromatography. The predominant regioisomer (corresponding to amino substitution at the C-4 position, I-1) is further functionalized at C-2 with a primary amine ($R^1$—$NH_2$) to afford I-2, and followed by nitro reduction to provide I-3. Purine formation is achieved by heating with an aldehyde in DMA to afford I-4.

Analogous compounds of formula I can be synthesized using similar experimental procedures.

Procedure A: Intermediate 1 (I-1)—2-Chloro-N-cyclopropyl-5-nitropyrimidin-4-amine

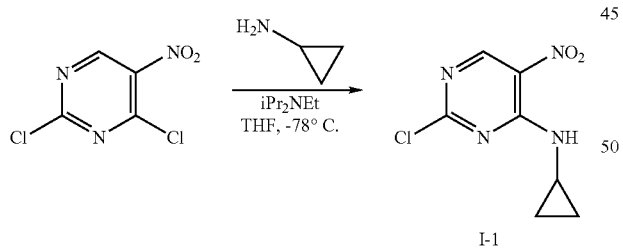

To 10.0 g (53 mmol, 1.0 eq.) of 2,4-dichloro-5-nitropyrimidine in 40 mL of THF at −78° C. was added 22 mL (120 mmol, 2.2 eq.) of N,N-diisopropylethylamine and 3.7 mL (53 mmol, 1.0 eq.) of cyclopropylamine. The reaction mixture was stirred at −78° C. for 30 min and then allowed to warm to room temperature and stirred for an additional 1 h. The solvent was removed in vacuo to afford a yellow solid. The product was purified by flash chromatography (15% EtOAc/hexanes) to provide 8.8 g (8.1 mmol, 77%) of 2-chloro-N-cyclopropyl-5-nitropyrimidin-4-amine (I-1) as a yellow solid.

Procedure B: Intermediate 3 (I-3)—$N^4$-Cyclopropyl-$N^2$-(2-(thiophen-2-yl)ethyl)pyrimidine-2,4,5-triamine

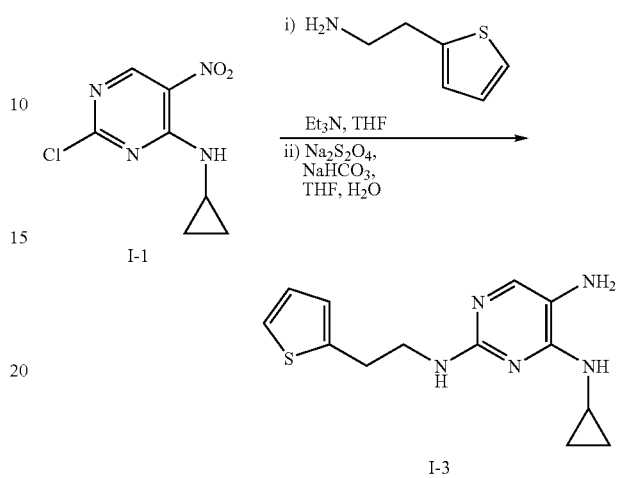

To a solution of 0.2 g (0.93 mmol, 1.0 eq.) of 2-chloro-N-cyclopropyl-5-nitropyrimidin-4-amine (I-1) in 5 mL of THF was added 0.19 mL (1.4 mmol, 1.5 eq.) of triethylamine followed by 0.14 g (1.1 mmol, 1.2 eq.) of 2-thiophene ethylamine. The reaction mixture was stirred at room temperature for 30 min and 2 mL of THF was added. A solution of 1.0 g (~5.7 mmol, ~85% tech. grade, ~6.0 eq.) of sodium hydrosulfite and 1.0 g (12 mmol, ~13 eq.) of sodium hydrogen carbonate in 10 mL of water was added, and the mixture was stirred vigorously at room temperature for 1 h. The mixture was diluted with 20 mL of EtOAc and washed 10 mL of sat. brine. The organic layer was dried ($Na_2SO_4$) and the solvent was removed in vacuo to provide 0.16 g of crude $N^4$-cyclopropyl-$N^2$-(2-(thiophen-2-yl)ethyl)pyrimidine-2,4,5-triamine (I-3).

Procedure C: Product 4 (I-4)—9-Cyclopropyl-8-(pyridin-4-yl)-N-(2-(thiophen-2-yl)ethyl)-9H-purin-2-amine

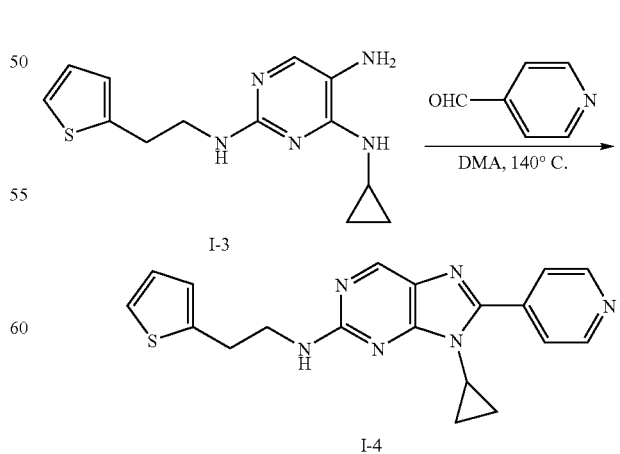

To a solution of 0.032 g (0.12 mmol, 1.0 eq.) of N⁴-cyclopropyl-N²-(2-(thiophen-2-yl)ethyl)pyrimidine-2,4,5-triamine (I-3) in 5 mL of DMA was added 0.05 mL (0.38 mmol, 3.2 eq.) of 4-pyridinecarboxaldehyde. The mixture was stirred at 140° C. for 16 h and the solvent was removed in vacuo. The residue was purified by flash chromatography (EtOAc) to afford 0.015 g (0.04 mmol, 35%) of 9-cyclopropyl-8-(pyridin-4-yl)-N-(2-(thiophen-2-yl)ethyl)-9H-purin-2-amine (I-4) as a yellow solid.

Alternatively, compounds of formula I can be synthesized in four steps from commercially available 2,4-dichloro-5-nitropyrimidine (Scheme 2) employing a modified synthesis involving production of a 2-chloropurine intermediate (I-6). Initial N-arylation of a primary amine (R²—NH₂) with 2,4-dichloro-5-nitropyrimidine provides I-1 (vide supra). Reduction of the nitro group of I-1 provides I-5 which is converted to the 2-chloropurine intermediate (I-6) by reaction with an aldehyde in DMA at 140° C. 2-Aminopurine formation is achieved by reaction of I-6 with an amine (R¹—NH₂) in the presence of BINAP, Pd₂(dba)₃ and t-BuONa at 160° C. The illustration of examples, but not the limitation, of the synthesis of compounds of formula I is detailed in procedures D-F.

Scheme 2:

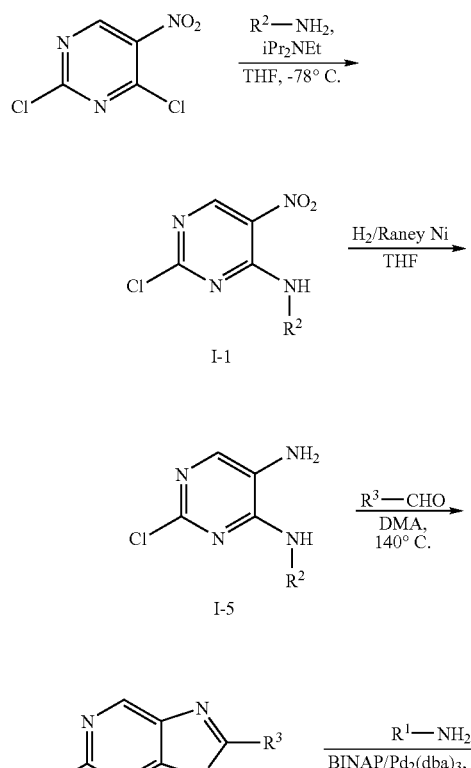

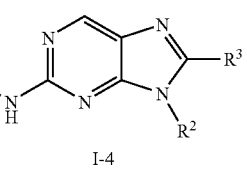

Procedure D: Intermediate 5 (I-5)—2-Chloro-N⁴-ethylpyrimidine-4,5-diamine

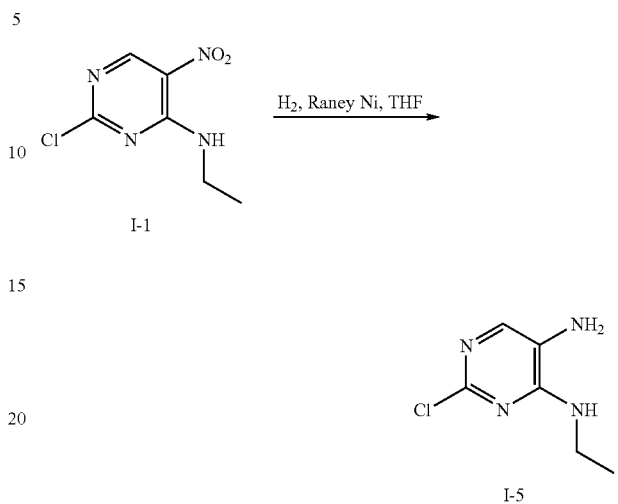

To a solution of 10.0 g (50 mmol, 1.0 eq.) of 2-chloro-N-ethyl-5-nitropyrimidin-4-amine (I-1) in 300 mL of THF was added ~4.0 g of Raney Nickel. The solution was stirred under 1 atm. of hydrogen at room temperature for 12 h. The reaction mixture was filtered through Celite® and the pad was washed with 100 mL of THF. The solvent was removed in vacuo to provide 8.0 g (46 mmol, 92%) of 2-chloro-N⁴-ethylpyrimidine-4,5-diamine (I-5).

Procedure E: Intermediate 6 (I-6)—2-Chloro-9-ethyl-8-(pyridin-4-yl)-9H-purine

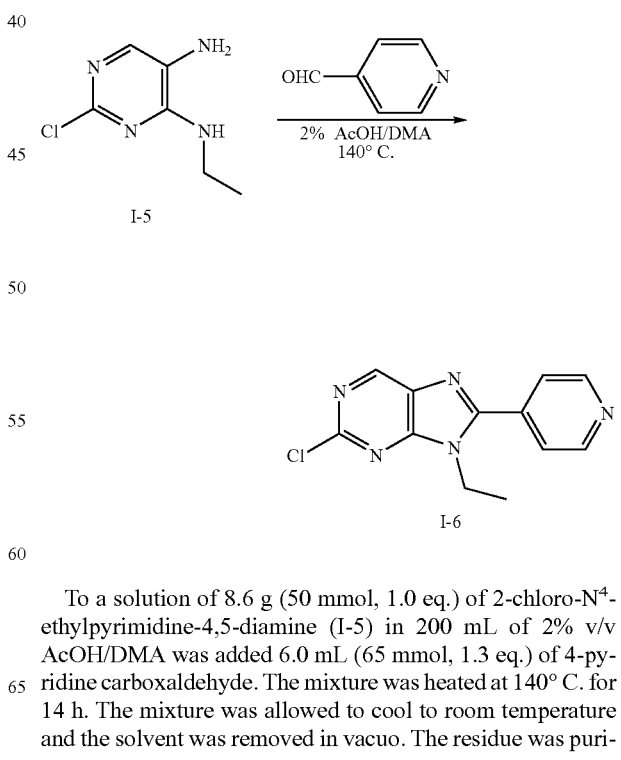

To a solution of 8.6 g (50 mmol, 1.0 eq.) of 2-chloro-N⁴-ethylpyrimidine-4,5-diamine (I-5) in 200 mL of 2% v/v AcOH/DMA was added 6.0 mL (65 mmol, 1.3 eq.) of 4-pyridine carboxaldehyde. The mixture was heated at 140° C. for 14 h. The mixture was allowed to cool to room temperature and the solvent was removed in vacuo. The residue was purified by preparative HPLC to provide 2.0 g (7.7 mmol, 15%) of 2-chloro-9-ethyl-8-(pyridin-4-yl)-9H-purine (I-6).

Procedure F: Product 4 (I-4)

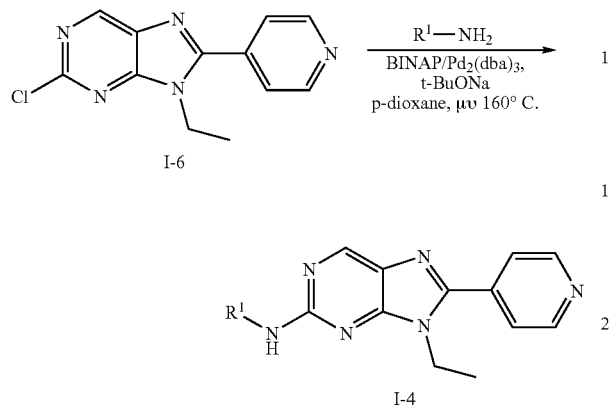

To a solution of 60 mg (0.23 mmol, 1.0 eq.) of 2-chloro-9-ethyl-8-(pyridin-4-yl)-9H-purine (I-6) in 3 mL of p-dioxane was added 0.46 mmol (2.0 eq.) of a primary amine ($R^1$—$NH_2$) followed by 10 mg (0.016 mmol, 0.07 eq.) of BINAP, 10 mg (0.01 mmol, 0.05 eq.) of $Pd_2(dba)_3$ and 30 mg (0.31 mmol, 1.4 eq.) of t-BuONa. The reaction mixture was subjected to microwave irradiation, maintaining an internal reaction temperature of 160° C. for 40 min. The mixture was filtered and the filtrate was concentrated in vacuo. The resulting residue was purified by preparative HPLC to provide I-4.

Non-commercially available pyrimidine carboxaldehydes can be synthesized by means of conventional organic synthesis executable by those skilled in the art. The illustration of examples, but not the limitation, of the synthesis of pyrimidine carboxaldehydes is detailed in procedures G-K.

Procedure G: Intermediate 7
(I-7)—Pyrimidine-4-carboxaldehyde

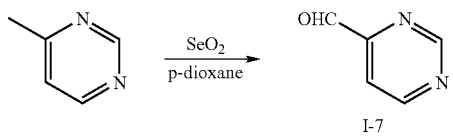

To a solution of 1.0 g (10 mmol, 1.0 eq.) of 4-methylpyrimidine in 10 mL of p-dioxane was added 1.2 g (10 mmol, 1.0 eq.) of selenium dioxide. The resulting mixture was heated at 100° C. for 5 h and then cooled to room temperature. After adding an additional 0.25 g (2.3 mmol, 0.23 eq.) of selenium dioxide, the reaction mixture was heated at 100° C. for a further 1 h. The mixture was cooled to room temperature and filtered through Celite®. The Celite® cake was washed with 200 mL of ethyl acetate and the filtrate was concentrated in vacuo. The resulting dark brown oil was suspended in 200 mL of methylene chloride and filtered. The solvent was removed in vacuo to afford 0.3 g (2.8 mmol, 28%) of pyrimidine-4-carboxaldehyde (I-7) as dark brown oil.

Procedure H: Intermediate 8
(I-8)—2-Aminopyrimidine-4-carboxaldehyde dimethylacetal

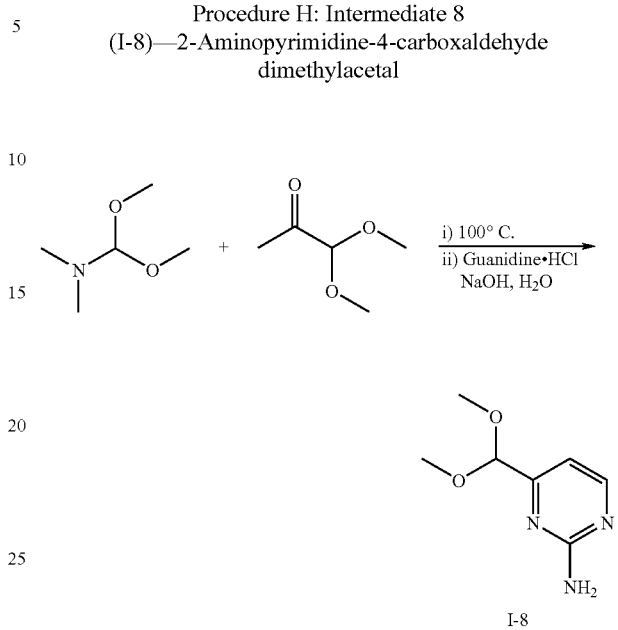

A solution of 5.5 mL (41 mmol, 1.0 eq.) of dimethylformamide dimethyl acetal and 5.0 mL (41 mmol, 1.0 eq.) pyruvic aldehyde dimethyl acetal was heated at 100° C. for 16 h. Methanol was removed in vacuo to afford a brown oil. A solution of 1.8 g (45 mmol, 1.1 eq.) of sodium hydroxide in 5 mL of water was added to a solution of 4.3 g (45 mmol, 1.1 eq.) of guanidine HCl in 10 mL of water. The resulting solution was added to the above described oil. The resulting mixture was stirred at room temperature for 48 h. The mixture was filtered to provide 2.5 g (15 mmol, 36%) of 2-aminopyrimidine-4-carboxaldehyde dimethylacetal (I-8).

Procedure I: Intermediate 9
(I-9)—2-Aminopyrimidine-4-carboxaldehyde

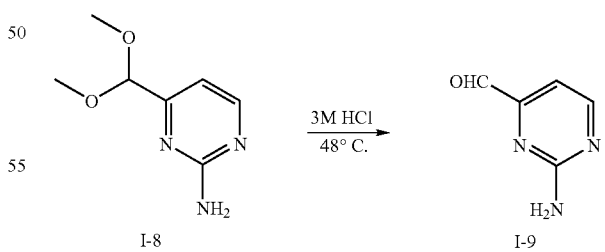

A solution of 2.5 g (15 mmol, 1.0 eq.) of 2-aminopyrimidine-4-carboxaldehyde dimethylacetal (I-8) in 16 mL (48 mmol, 3.2 eq.) of 3M HCl was heated at 48° C. for 14 h. The mixture was allowed to cool to room temperature and diluted with 50 mL of EtOAc. The aqueous layer was neutralized with $NaHCO_3$ and then extracted with EtOAc (5×50 mL). The combined organic extracts were dried ($Na_2SO_4$) and the solvent removed in vacuo to provide 0.69 g (5.6 mmol, 37%) of 2-aminopyrimidine-4-carboxaldehyde (I-9) as a yellow solid.

Procedure J: Intermediate 8 (I-10)—2-Methylaminopyrimidine-4-carboxaldehyde dimethyl acetal

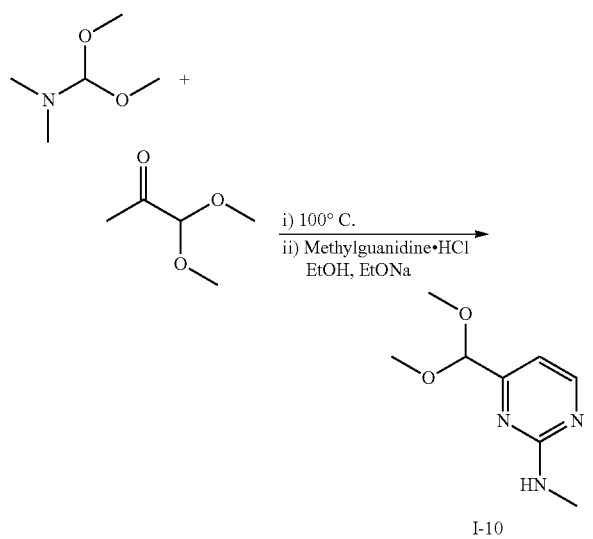

I-10

A solution of 5.5 mL (41 mmol, 1.0 eq.) of dimethylformamide dimethyl acetal and 5.0 mL (41 mmol, 1.0 eq.) of pyruvic aldehyde dimethyl acetal was heated at 100° C. for 16 h. Methanol was removed in vacuo to afford a brown oil. To a solution of 15 mL of sodium ethoxide (21% in ethanol, 41 mmol, 1.0 eq.) was added 4.5 g (41 mmol, 1.0 eq.) of methyl guanidine HCl. The mixture was stirred for 10 min before a solution of the above described oil in 15 mL anhydrous ethanol was added. The mixture was heated to reflux for 24 h, allowed to cool to room temperature and filtered. The solvent was removed in vacuo to afford 2-methylaminopyrimidine-4-carboxaldehyde dimethyl acetal (I-10) as a dark brown oil which was used in the next step without further purification Procedure K: Intermediate 11 (I-11)—2-Methylaminopyrimidine-4-carboxaldehyde

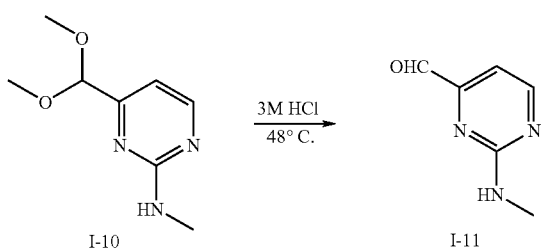

2-Methylaminopyrimidine-4-carboxaldehyde (I-11) was synthesized in a similar manner to 2-aminopyrimidine-4-carboxaldehyde (I-9, procedure I). Reaction of crude 2-methylaminopyrimidine-4-carboxaldehyde dimethyl acetal (I-10) from procedure J provided 1.7 g (30% from dimethylformamide dimethyl acetal) of 2-methylaminopyrimidine-4-carboxaldehyde (I-11) as dark brown foam.

Compounds of formula I (type I-4) can be further functionalized via alkylation of the C-2 amino group with an alkyl halide. The illustration of an example, but not the limitation, of the synthesis of compounds of formula I via alkylation of the C-2 amino group is detailed in procedure L.

Procedure L: Product 12 (I-12)—9-Cyclopropyl-N-(3-methoxyphenyl)-N-methyl-8-(pyridin-4-yl)-9H-purin-2-amine

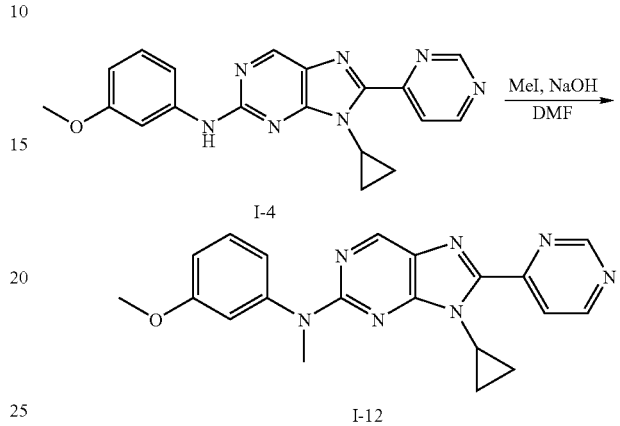

To a solution of 4.3 mg (0.012 mmol, 1.0 eq.) of 9-cyclopropyl-N-(3-methoxyphenyl-8-(pyridin-4-yl)-9H-purin-2-amine (synthesized using Procedures A-C) in 1 mL of DMF was added 0.03 mL (0.48 mmol, 40 eq.) of methyl iodide followed by 20 mg (0.48 mmol, 40 eq.) of sodium hydroxide. The reaction mixture was stirred at room temperature for 16 h. The reaction mixture was filtered, and the filtrate was concentrated in vacuo. Purification of the resulting residue by semi-preparative HPLC afforded 1.9 mg (42%) of 9-cyclopropyl-N-(3-methoxyphenyl)-N-methyl-8-(pyridin-4-yl)-9H-purin-2-amine.

Compounds of formula I where $R^3$ is 4-pyridyl, and an amino substituent is incorporated at the 2-position of the pyridine ring (I-14), can be synthesized using the procedure of Huang, X.; Buchwald, S. L. *Org. Lett.* 2001, 3, 3417, (Scheme 3). Intermediates of type I-13 were synthesized using procedures A-C.

Scheme 3:

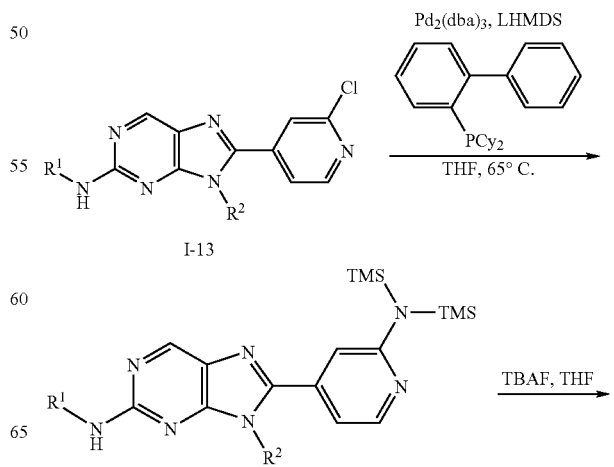

-continued

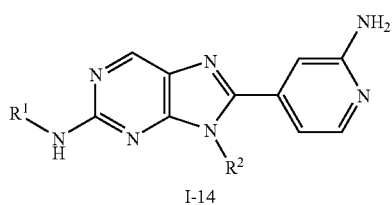

I-14

Compounds of the general formula I-15 and I-16 were synthesized from the corresponding 2-chloropyridine (I-13) according to Scheme 4.

Scheme 4:

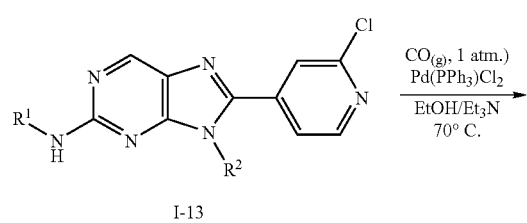

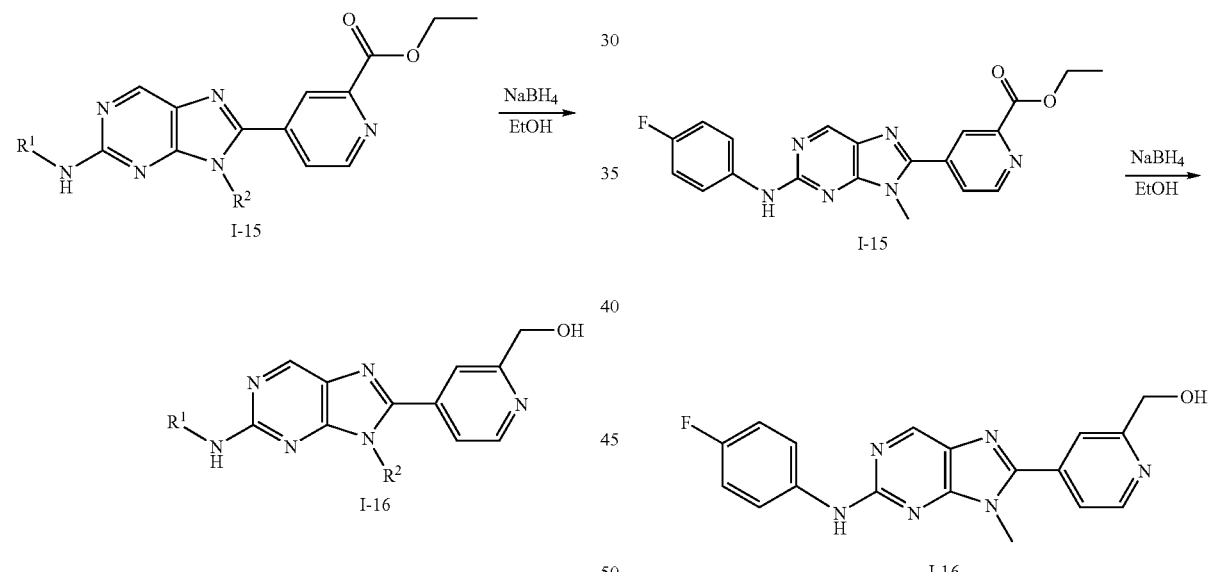

The illustration of examples, but not the limitation, of the synthesis of compounds of the general formula I-15 and I-16 is detailed in procedures M-N.

Procedure M: Product 15 (I-15)—Ethyl 4-(2-(4-fluorophenylamino)-9-methyl-9H-purin-8-yl)picolinate

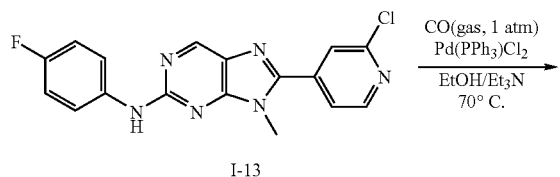

-continued

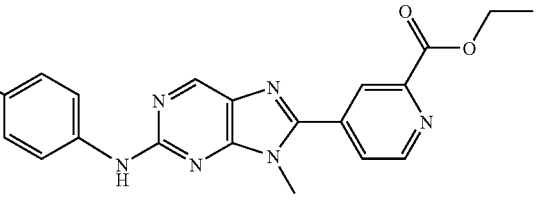

I-15

To a suspension of 0.8 g (2.3 mmol, 1.0 eq.) 8-(2-chloropyridine-4-yl)-N-(4-fluorophenyl)-9-methyl-9H-purin-2-amine (I-13) in 20 mL of EtOH and 10 mL of triethylamine was added 160 mg (0.23 mmol, 0.10 eq.) of Pd(PPh₃)Cl₂. The mixture was heated at 70° C. for 18 h with constant CO saturation. The volatiles were removed in vacuo and the resulting residue was purified by flash chromatography (EtOAc/Hexane) to afford 42 mg of I-15 and 700 mg of recovered I-13.

Procedure N: Product 16 (I-16)—(4-(2-(4-Fluorophenylamino)-9-methyl-9H-purin-8-yl)pyridine-2-yl)methanol To a solution of 30 mg (0.077 mmol, 1.0 eq.) of ethyl 4-(2-(4-fluorophenylamino)-9-methyl-9H-purin-8-yl)picolinate (I-15) in 3 mL of ethanol was added 58 mg (1.5 mmol, 20 eq.) of sodium borohydride. The mixture was stirred at room temperature for 16 h. The volatiles were removed in vacuo and the resulting residue was purified by semi-preparative HPLC to afford 0.9 mg (3%) of (4-(2-(4-fluorophenylamino)-9-methyl-9H-purin-8-yl)pyridine-2-yl)methanol (I-16).

Compounds of formula I, type I-4 that incorporate $R^2$ as hydrogen can be synthesized by incorporation of 2,4-dimethoxybenzyl at $R^2$ according to procedures A-C to generate I-17. Acid mediated debenzylation of I-17 affords I-18 (Scheme 5).

Scheme 5:

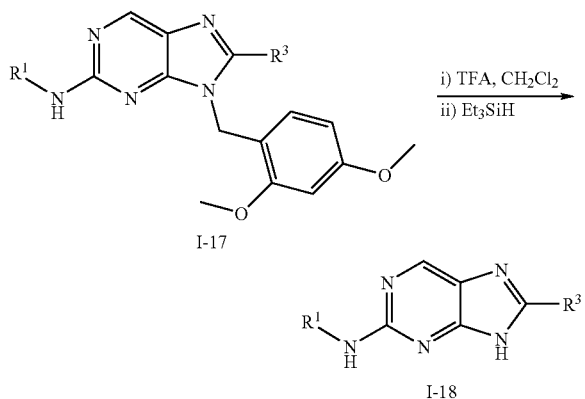

Scheme 6:

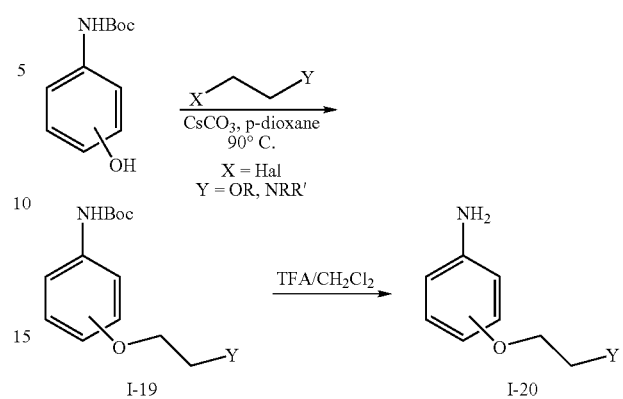

The illustration of an example, but not the limitation, of the synthesis of compounds of the general formula I-18 is detailed in procedure O.

The illustration of examples, but not the limitation, of the synthesis of compounds of general formula I-20 is detailed in procedure P.

Procedure O: Product 18 (I-18)—N-(4-Fluorophenyl)-8-(pyridin-4-yl)-9H-purin-2-amine Procedure P: Intermediate 20 (I-20)—4-(2-Morpholinoethoxy)benzenamine

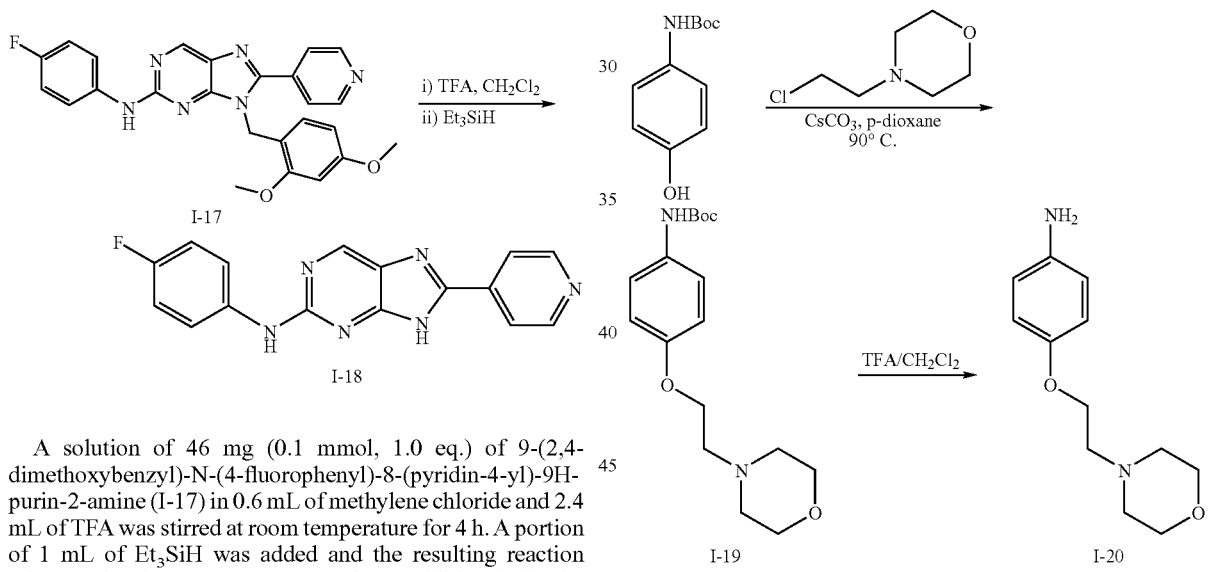

A solution of 46 mg (0.1 mmol, 1.0 eq.) of 9-(2,4-dimethoxybenzyl)-N-(4-fluorophenyl)-8-(pyridin-4-yl)-9H-purin-2-amine (I-17) in 0.6 mL of methylene chloride and 2.4 mL of TFA was stirred at room temperature for 4 h. A portion of 1 mL of Et₃SiH was added and the resulting reaction mixture stirred at room temperature for an additional 1 h. The volatiles were removed in vacuo and the residue purified by semi-preparative HPLC to provide 7.3 mg (24%) of N-(4-fluorophenyl)-8-(pyridin-4-yl)-9H-purin-2-amine (I-18).

Non-commercially available amines and anilines can be synthesized by means of conventional organic synthesis executable by those skilled in the art. The illustration of examples, but not the limitation, of the synthesis of non-commercially available amines and anilines for incorporation within the R¹ component of compounds of formula I are detailed below. Target compounds can be synthesized by employing the non-commercially available amines and anilines in the procedures outlined in the preceding schemes.

Compounds of general formula I-20 can be synthesized in two steps from commercially available N-Boc protected aminophenols. O-Alkylation of an N-Boc protected aminophenol with an alkyl halide provides I-19, which, following deprotection, provides I-20 (Scheme 6).

To a solution of 0.1 g (0.48 mmol, 1.0 eq.) of tert-butyl 4-hydroxyphenylcarbamate in 5 mL of p-dioxane was added 0.13 g (0.72 mmol, 1.5 eq.) of 4-(2-chloroethyl)morpholine and 0.47 g (1.43 mmol, 3.0 eq.) cesium carbonate. The suspension was heated at 90° C. for 16 h. The reaction mixture was allowed to cool to room temperature and filtered. The solvent was removed in vacuo to provide tert-butyl 4-(2-morpholinoethoxy)phenylcarbamate (I-19), which was redissolved in 30% v/v TFA/methylene chloride and the resulting mixture was stirred at room temperature for 1 h. The solvent was removed in vacuo, and the residue was redissolved in methylene chloride. The organic solution was washed with sat. NaHCO₃, dried (Na₂SO₄) and the solvent was removed in vacuo to provide 95 mg (0.43 mmol, 95%) of (4-(2-morpholinoethoxy)-benzenamine (I-20).

Compounds of general formula I-22 can be synthesized in two steps from the corresponding nitrophenylalkylamine.

Acylation of the nitrophenyl alkylamine followed by nitro reduction provides I-22 (Scheme 7).

Scheme 7:

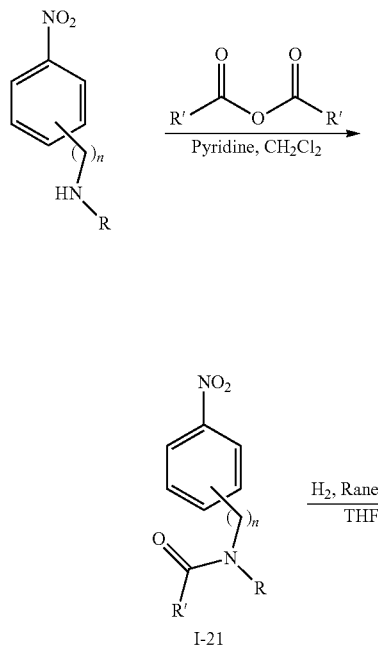

The illustration of examples, but not the limitation, of the synthesis compounds of general formula I-22 is detailed in procedures Q-R.

Procedure Q: Intermediate 22
(I-21)—N-(4-Nitrobenzyl)acetamide

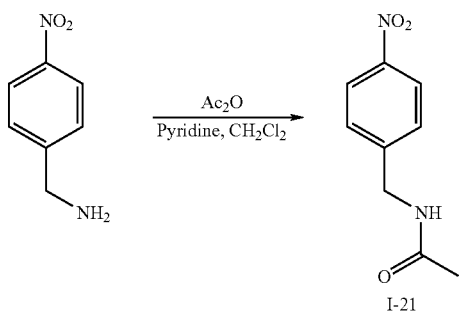

To a solution of 8.0 g (42 mmol, 1.0 eq.) of (4-nitrophenyl)methanamine hydrochloride in 40 mL of methylene chloride and 28 mL (340 mmol, 8.0 eq.) of pyridine was added 16 mL (170 mmol, 4.0 eq.) of acetic anhydride. The mixture was stirred at room temperature for 16 h and diluted with 200 mL of methylene chloride. The organic solution was washed with sat. brine and dried ($Na_2SO_4$). The solvent was removed in vacuo to provide 8.0 g (41 mmol, 98%) of N-(4-nitrobenzyl)acetamide (I-21).

Procedure R: Intermediate 22
(I-22)—N-(4-Aminobenzyl)acetamide

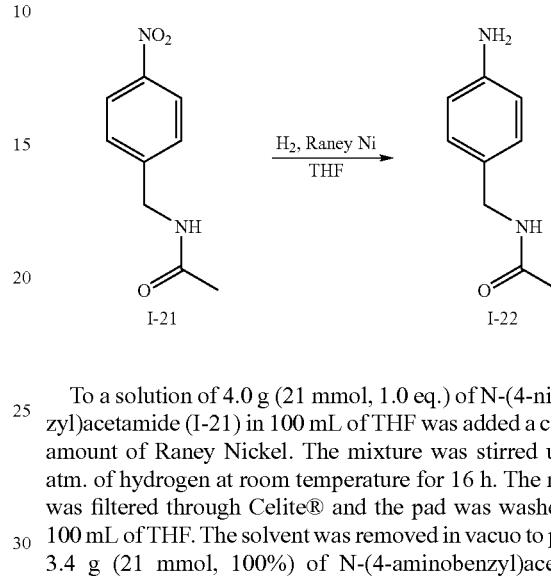

To a solution of 4.0 g (21 mmol, 1.0 eq.) of N-(4-nitrobenzyl)acetamide (I-21) in 100 mL of THF was added a catalytic amount of Raney Nickel. The mixture was stirred under 1 atm. of hydrogen at room temperature for 16 h. The mixture was filtered through Celite® and the pad was washed with 100 mL of THF. The solvent was removed in vacuo to provide 3.4 g (21 mmol, 100%) of N-(4-aminobenzyl)acetamide (I-22).

Compounds of general structure I-26 were synthesized from the corresponding nitrophenylalkylalcohol (Scheme 8). Mesylation of the primary alcohol (I-23) provides I-24, which is used to generate I-25 via alkylation of an amine (NHR(R')). Nitro reduction of I-25 provides I-26.

Scheme 8:

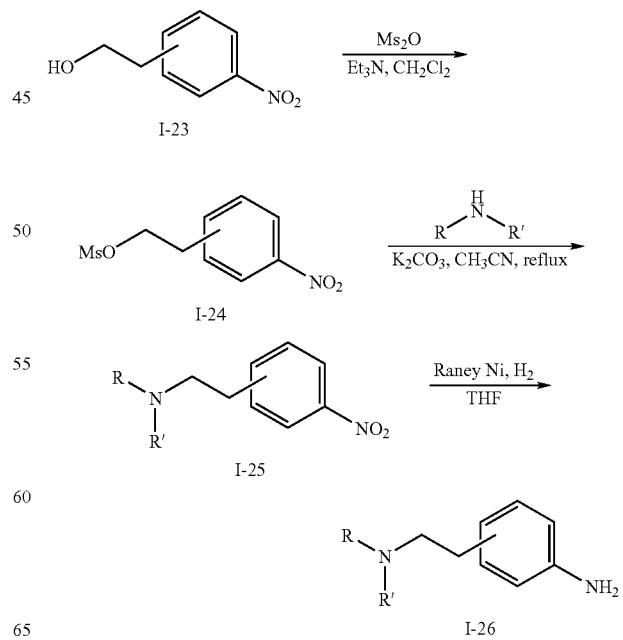

The illustration of examples, but not the limitation, of the synthesis compounds of general formula I-26 is detailed in procedures S-U.

Procedure S: Intermediate 24
(I-24)—3-Nitrophenethyl methanesulfonate

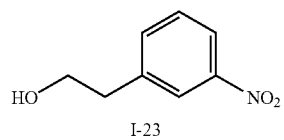

To a solution of 1.6 g (10 mmol, 1.0 eq.) of 2-(3-nitrophenyl) (I-23) in 20 mL of methylene chloride was added 2.8 mL (20 mmol, 2.0 eq.) of triethylamine. A solution of 1.7 g (10 mmol, 1.0 eq.) of methanesulfonic anhydride in 10 mL of methylene chloride was added and the mixture was stirred at room temperature for 16 h. The reaction mixture was washed with sat. brine and the organic layer was dried ($Na_2SO_4$). The solvent was removed in vacuo and the resulting residue was purified by flash chromatography to provide 2.2 g (9.0 mmol, 90%) of 3-nitrophenethyl methanesulfonate (I-24).

Procedure T: Intermediate 25
(I-25)—1-(3-Nitrophenethyl)piperidine

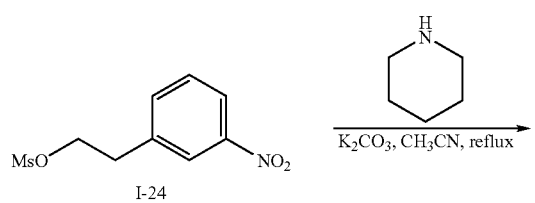

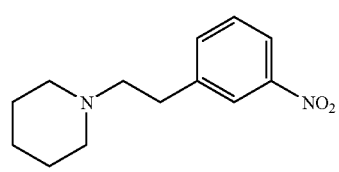

To a mixture of 0.49 g (2.0 mmol, 1.0 eq.) of 3-nitrophenethyl methanesulfonate (I-24) and 0.55 g (6.0 mmol, 3.0 eq.) of potassium carbonate in 20 mL of acetonitrile was added 0.4 mL (4.0 mmol, 2.0 eq.) of piperidine. The reaction mixture was stirred at reflux for 16 h. The reaction mixture was allowed to cool to room temperature, filtered and the solvent removed in vacuo. The resulting residue was purified by preparative TLC to provide 0.35 g (1.5 mmol, 75%) of 1-(3-nitrophenethyl)piperidine (I-25).

Procedure U: Intermediate 26 (I-26)—3-(2-(Piperidin-1-yl)ethyl)benzenamine

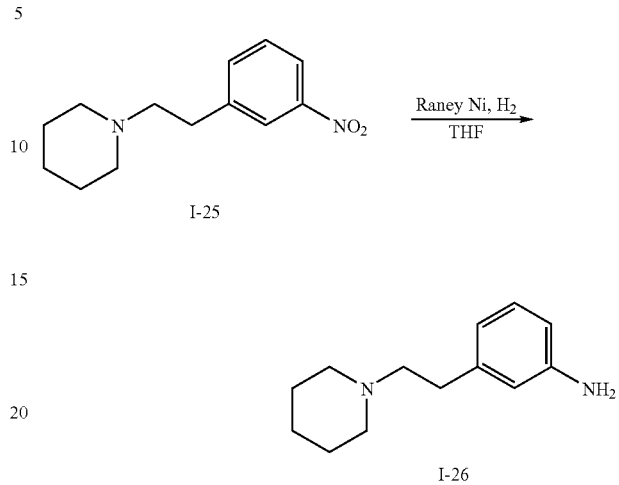

To a solution of 0.2 g (0.85 mmol, 1.0 eq.) of 1-(3-nitrophenethyl)piperidine (I-25) in 15 mL of THF was added ~30 mg of Raney Nickel. The reaction mixture was stirred under 1 atm. of hydrogen at room temperature for 16 h. The reaction mixture was then filtered through Celite® and the solvent was removed in vacuo to provide 3-(2-(piperidin-1-yl)ethyl)benzenamine (I-26).

Compounds of general structure I-28 were synthesized from the corresponding halomethyl nitrobenzene (Scheme 9). Alkylation of an amine (NHR(R')) with the halomethyl benzene provides I-27. Nitro reduction of I-27 provides I-28.

Scheme 9:

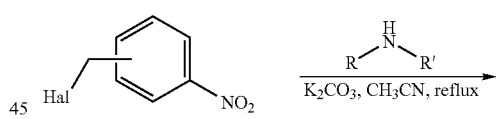

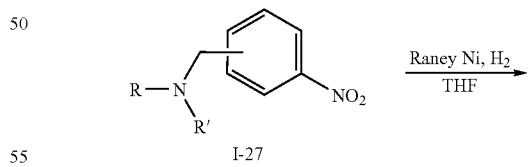

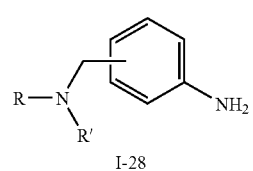

The illustration of examples, but not the limitation, of the synthesis compounds of general formula I-26 is detailed in procedures V-W.

Procedure V: Intermediate 27
(I-27)—1-(4-Nitrobenzyl)piperidine

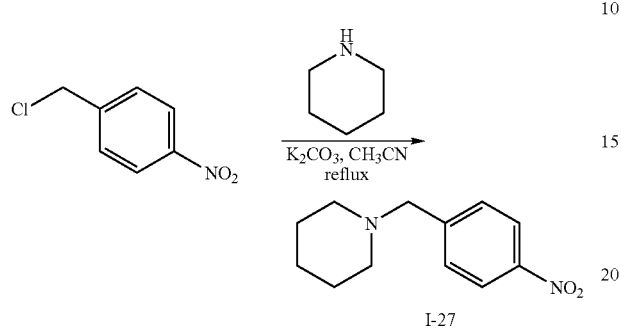

To a solution of 0.34 g (2.0 mmol, 1.0 eq.) of 1-(chloromethyl)-4-nitrobenzene in 20 mL of acetonitrile was added 0.83 g (6.0 mmol, 3.0 eq.) of potassium carbonate and 0.4 mL (4.0 mmol, 2.0 eq.) of piperidine. The reaction mixture was heated at reflux for 16 h. The reaction mixture was allowed to cool to room temperature, filtered and the solvent removed in vacuo. The resulting residue was purified by preparative TLC to give 0.31 g (1.4 mmol, 70%) of 1-(4-nitrobenzyl)piperidine (I-27).

Procedure W: Intermediate 28
(I-28)—4-(Piperidin-1-ylmethyl)benzenamine

To a solution of 0.22 g (1.0 mmol, 1.0 eq.) of 1-(4-nitrobenzyl)piperidine (I-27) in 20 mL of THF was added ~30 mg of Raney Nickel. The reaction mixture was stirred under at room temperature under 1 atm. of hydrogen for 12 h. The reaction mixture was through Celite® and the solvent removed in vacuo to provide 4-(piperidin-1-ylmethyl)benzenamine (I-28).

Compounds of general structure I-31 were synthesized from the corresponding halomethyl nitrobenzene (Scheme 10). Alkylation of a primary amine (R—NH$_2$) with the halomethyl benzene provides I-29. Protection of the secondary amino functionality with, for example, a t-butoxycarbonyl protecting group, provides I-30. Subsequent nitro reduction of I-30 provides I-31.

Scheme 10:

The illustration of examples, but not the limitation, of the synthesis compounds of general formula I-31 is detailed in procedures X-Z. t-Butoxycarbonyl protecting groups can be removed following incorporation of compounds of general formula I-31 into the previously described syntheses to provide compounds of formula 1.

Procedure X: Intermediate 29
(I-29)—N-(4-Nitrobenzyl)ethanamine

To a mixture of 0.34 g (2.0 mmol, 1.0 eq.) of 1-(chloromethyl)-4-nitrobenzene and 1.38 g (10 mmol, 5.0 eq.) of potassium carbonate in 20 mL of acetonitrile was added 0.33 g (4.0 mmol, 2.0 eq.) ethylamine hydrochloride. The reaction mixture was heated at reflux for 16 h. The reaction mixture was allowed to cool to room temperature, filtered and the solvent removed in vacuo to provide 0.18 g (1.0 mmol, 50%) of N-(4-nitrobenzyl)ethanamine (I-29).

Procedure Y: Intermediate 30 (I-30)—t-Butyl 4-nitrobenzyl(ethyl)carbamate

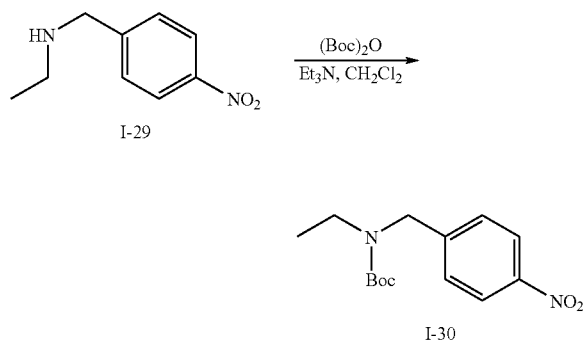

I-29

I-30

To a solution of 0.18 g (1.0 mmol, 1.0 eq.) of N-(4-nitrobenzyl)ethanamine (I-29) and 0.28 mL (2.0 mmol, 2.0 eq.) of triethylamine in 20 mL of methylene chloride was added 0.44 g (2.0 mmol, 2.0 eq.) di-tert-butyl dicarbonate. The reaction mixture was stirred at room temperature for 16 h. The resulting solution was washed with 1M $NaHCO_3$ solution and sat. brine. The organic layer was dried ($Na_2SO_4$) and the solvent was removed in vacuo. The resulting residue was purified by preparative TLC to afford 0.25 g (0.9 mmol, 89%) of t-butyl 4-nitrobenzyl(ethyl)carbamate (I-30).

Procedure Z: Intermediate 31 (I-31)—t-Butyl 4-nitrobenzyl(ethyl)carbamate

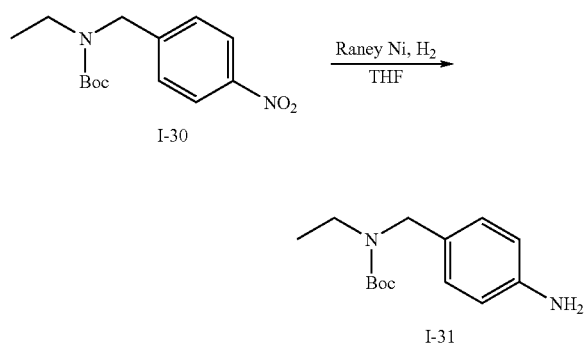

I-30

I-31

To a solution of 0.15 g (0.53 mmol, 1.0 eq.) of t-butyl 4-nitrobenzyl(ethyl)carbamate (I-30) in 10 mL of THF was added ~30 mg of Raney Nickel. The reaction mixture was stirred at room temperature under 1 atm. of hydrogen for 12 h. The reaction mixture was through Celite® and the solvent removed in vacuo to provide t-Butyl 4-nitrobenzyl(ethyl) carbamate (I-31).

Analytical HPLC Analysis:

Method A: Waters Millennium 2690/996PDA separations system employing a Phenomonex Luna 3u C8 50×4.6 mm analytical column. The aqueous acetonitrile based solvent gradient involves;

0-1 min—Isocratic 10% of (0.1% TFA/acetonitrile); 1 min-7 min—Linear gradient of 10-90% of (0.1% TFA/acetonitrile): 7 min-9 min—Isocratic 90% of (0.1% TFA/acetonitrile); 9 min-10 min—Linear gradient of 90-10% of (0.1% TFA/acetonitrile); 10 min-12 min—Isocratic 10% of (0.1% TFA/acetonitrile). Flow rate=1 mL/min.

Method B: Waters Millennium 2690/996PDA separations system employing a Phenomenex Columbus 5u C18 column 100×2.00 mm analytical column. The aqueous acetonitrile based solvent gradient involves;

0-0.5 min—Isocratic 10% of (0.05% TFA/acetonitrile); 0.5 min-5.5 min—Linear gradient of 10-90% of (0.05% TFA/acetonitrile): 5.5 min-7.5 min—Isocratic 90% of (0.05% TFA/acetonitrile); 7.5 min-8 min—Linear gradient of 90-10% of (0.05% TFA/acetonitrile); 8 min-10 min—Isocratic 10% of (0.05% TFA/acetonitrile). Flow rate=0.4 mL/min.

Method C: Waters Millennium 2695/996PDA separations system employing a Phenomonex Luna 3u C8 50×4.6 mm analytical column. The aqueous acetonitrile based solvent gradient involves;

0-1 min—Isocratic 10% of (0.1% TFA/acetonitrile); 1 min-8 min—Linear gradient of 10-90% of (0.1% TFA/acetonitrile): 8 min-9 min—Isocratic 90% of (0.1% TFA/acetonitrile); 9 min-12 min—Isocratic 10% of (0.1% TFA/acetonitrile). Flow rate=1.1 mL/min.

Mass Spectroscopy

Mass Spectroscopy was conducted using a Thermo-electron LCQ classic or an Applied Biosciences PE Sciex API150ex. Liquid Chromatography Mass Spectroscopy was conducted using a Waters Millennium 2690/996PDA linked Thermo-electron LCQ classic.

NMR Spectroscopy $^1$H NMR spectroscopy was conducted using a Varian 300 MHz Gemini 2000, Bruker 300 MHz AVANCE 300 or Bruker 400 MHz AVANCE$^{II}$ 400.

EXAMPLES

Representative species are shown below in Table 1. Compounds exhibited $IC_{50}$ values for Mnk2≦10 µM.

TABLE 1

| Example | Structure | Hplc (min/Method) | m/z found ([M + H]+) |
|---|---|---|---|
| 1 | 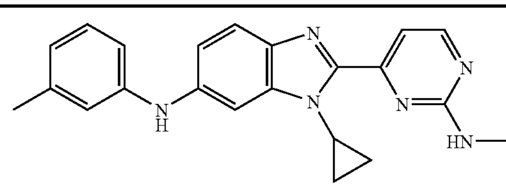 | 5.53 min/ Method A | 373.3 |

TABLE 1-continued

| Example | Structure | Hplc (min/Method) | m/z found ([M + H]+) |
|---|---|---|---|
| 2 | 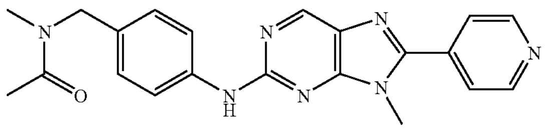 | 3.72 min/ Method A | 388.2 |
| 3 | 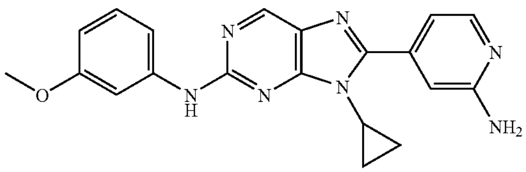 | 4.77 min/ Method A | 374.2 |
| 4 | 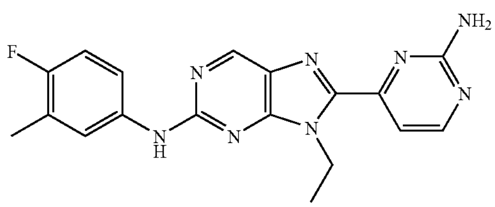 | 5.72 min/ Method B | 365.3 |
| 5 | 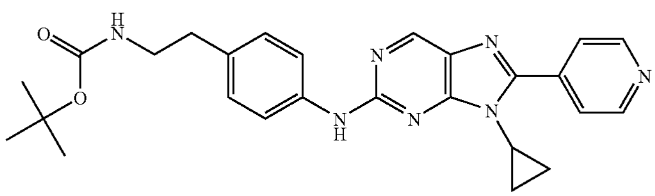 | 5.38 min/ Method A | 472.1 |
| 6 | 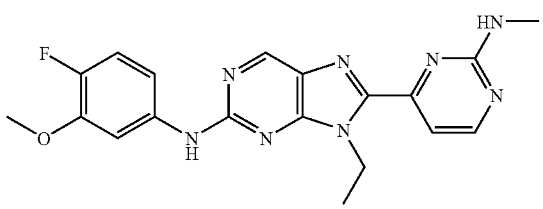 | 5.58 min/ Method A | 395.2 |
| 7 | 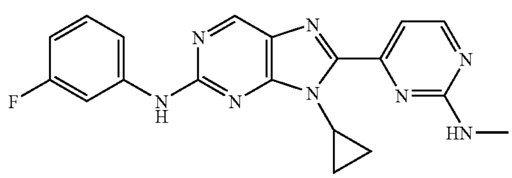 | 5.54 min/ Method A | 377.4 |
| 8 | 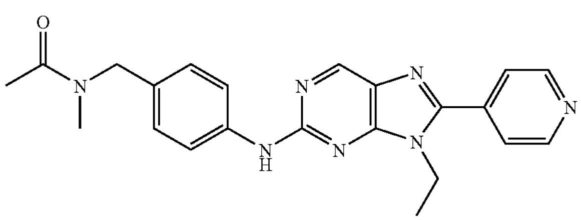 | 4.02 min/ Method A | 402.2 |
| 9 | 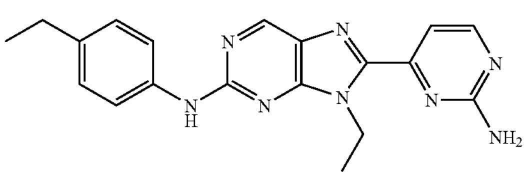 | 5.93 min/ Method B | 361.2 |

TABLE 1-continued

| Example | Structure | Hplc (min/Method) | m/z found ([M + H]+) |
|---|---|---|---|
| 10 | 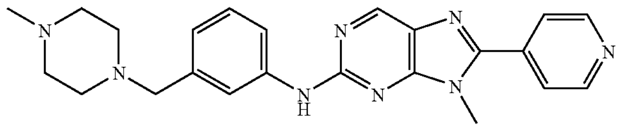 | 1.77 min/ Method B | 415.2 |
| 11 | 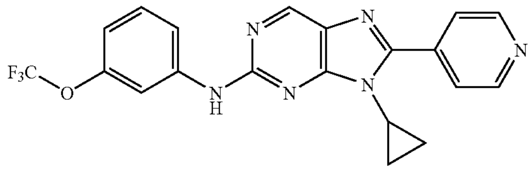 | 5.74 min/ Method A | 413.2 |
| 12 | 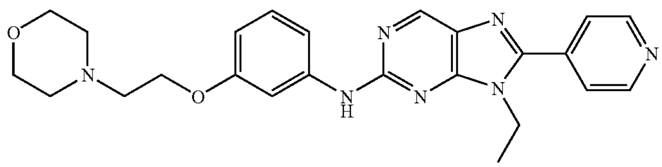 | 3.65 min/ Method A | 446.2 |
| 13 | 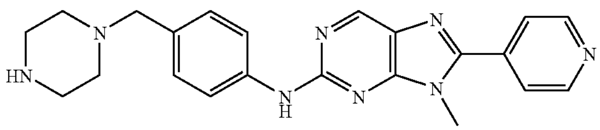 | 1.19 min/ Method B | 401.2 |
| 14 | 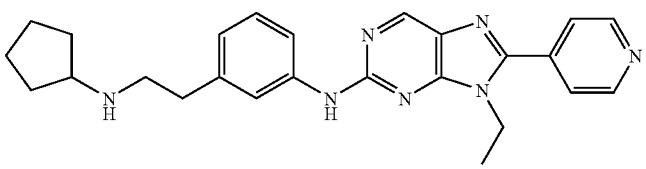 | 4.52 min/ Method B | 428.3 |
| 15 | 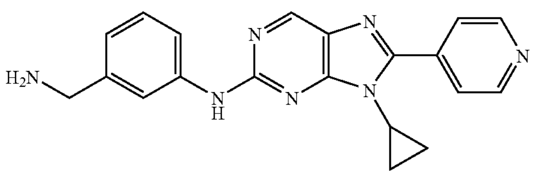 | 2.20 min/ Method A | 358.2 |
| 16 | 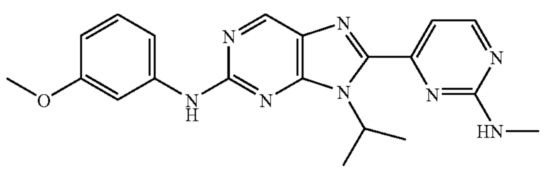 | 5.57 min/ Method A | 391.2 |
| 17 | 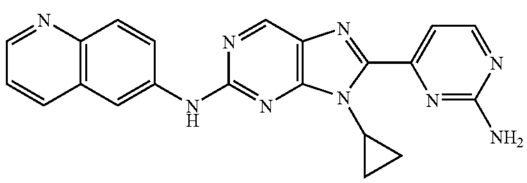 | 4.16 min/ Method B | 396.3 |
| 18 | 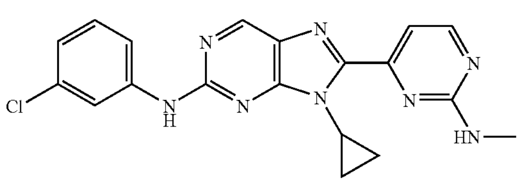 | 5.77 min/ Method A | 393.2 |

TABLE 1-continued

| Example | Structure | Hplc (min/Method) | m/z found ([M + H]$^+$) |
|---|---|---|---|
| 19 | 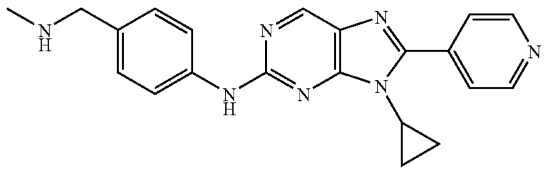 | 2.90 min/Method A | 372.2 |
| 20 | 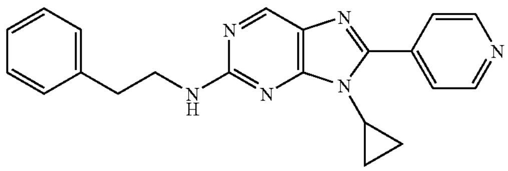 | 4.80 min/Method A | 357.3 |
| 21 | 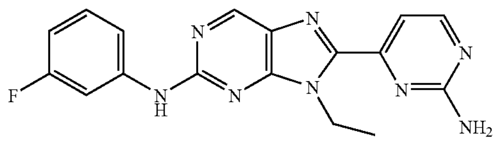 | 5.37 min/Method A | 351.2 |
| 22 | 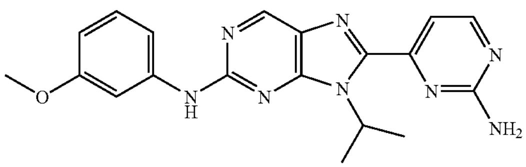 | 5.28 min/Method A | 377.1 |
| 23 | 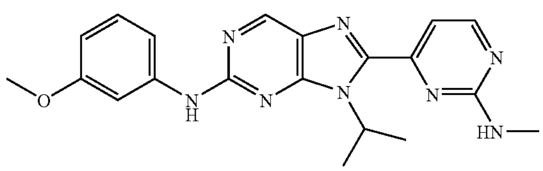 | 5.23 min/Method A | 389.2 |
| 24 | 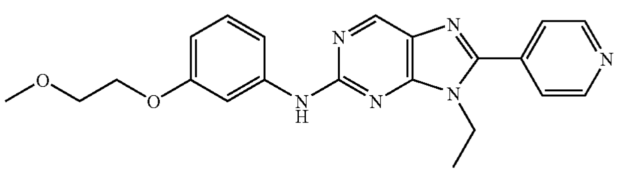 | 4.61 min/Method A | 391.2 |
| 25 | 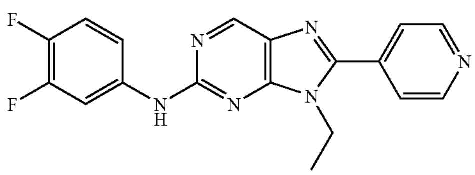 | 5.26 min/Method A | 353.2 |
| 26 | 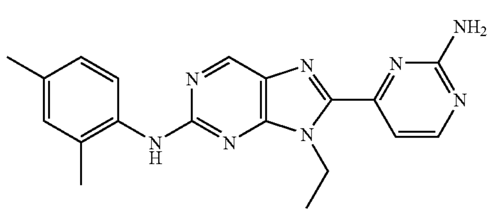 | 5.76 min/Method B | 361.2 |
| 27 | 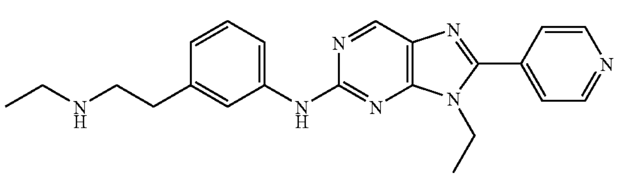 | 4.11 min/Method B | 388.3 |

TABLE 1-continued

| Example | Structure | Hplc (min/Method) | m/z found ([M + H]+) |
|---|---|---|---|
| 28 | 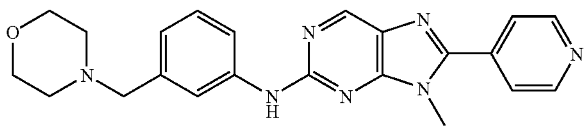 | 2.37 min/ Method B | 402.1 |
| 29 | 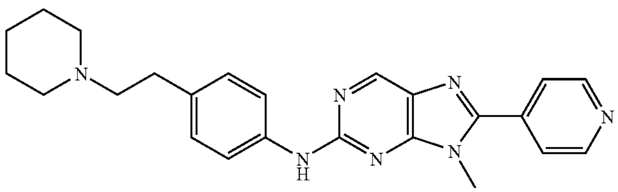 | 4.11 min/ Method B | 414.2 |
| 30 | 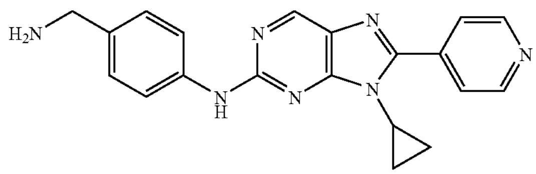 | 3.24 min/ Method A | 358.2 |
| 31 | 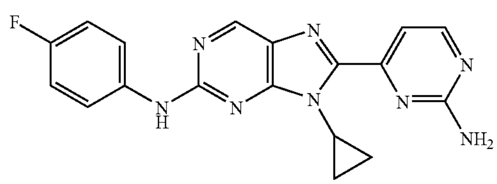 | 5.16 min/ Method A | 363.3 |
| 32 | 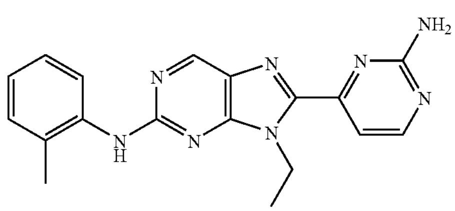 | 5.47 min/ Method B | 347.1 |
| 33 | 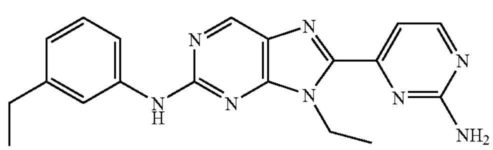 | 5.60 min/ Method A | 361.3 |
| 34 | 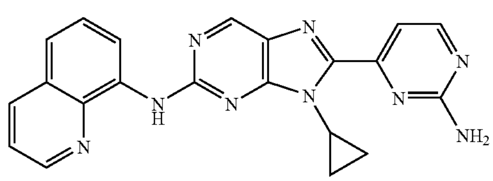 | 5.74 min/ Method B | 396.3 |
| 35 | 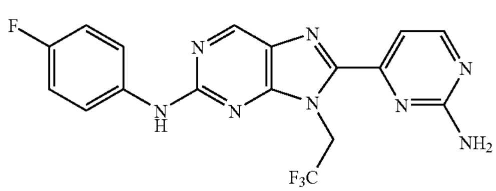 | 5.89 min/ Method A | 405.2 |

TABLE 1-continued

| Example | Structure | Hplc (min/Method) | m/z found ([M + H]+) |
| --- | --- | --- | --- |
| 36 | 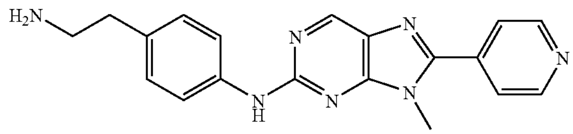 | 2.78 min/ Method A | 346.2 |
| 37 | 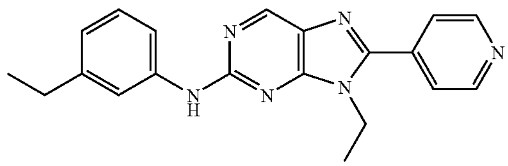 | 5.42 min/ Method A | 345.3 |
| 38 | 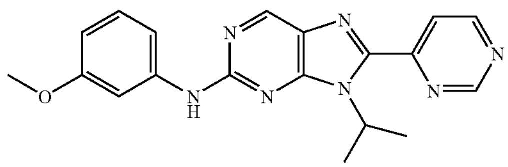 | 6.42 min/ Method A | 362.1 |
| 39 | 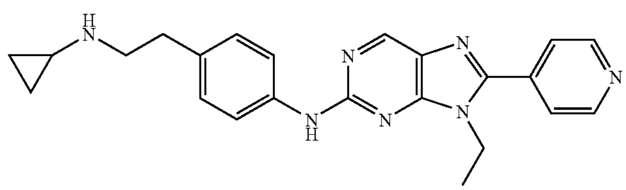 | 3.81 min/ Method B | 400.2 |
| 40 | 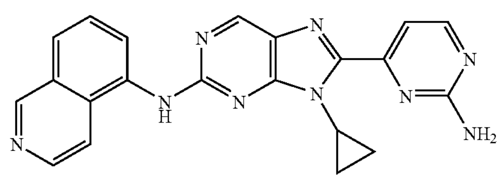 | 1.83 min/ Method A | 396.2 |
| 41 | 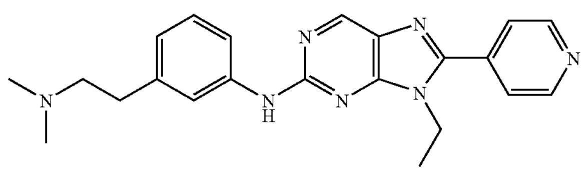 | 3.77 min/ Method B | 388.3 |
| 42 | 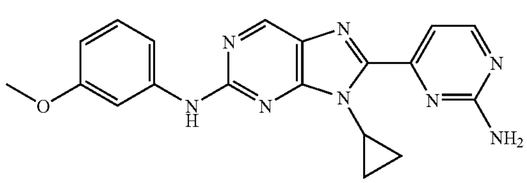 | 5.02 min/ Method A | 375.2 |
| 43 | 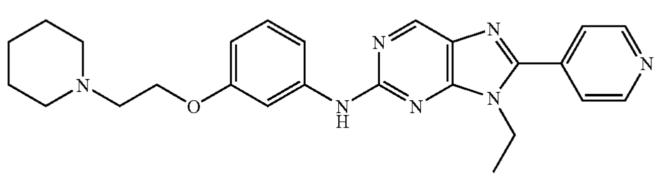 | 3.85 min/ Method A | 444.2 |
| 44 | 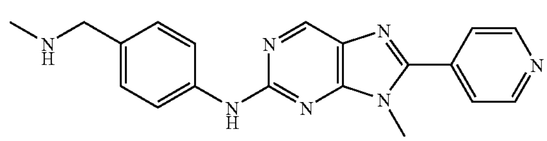 | 2.01 min/ Method A | 346.2 |

TABLE 1-continued

| Example | Structure | Hplc (min/Method) | m/z found ([M + H]+) |
|---|---|---|---|
| 45 | 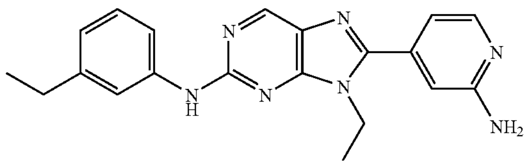 | 5.28 min/ Method A | 360.3 |
| 46 | 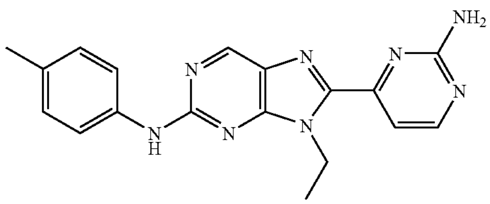 | 5.72 min/ Method B | 347.3 |
| 47 | 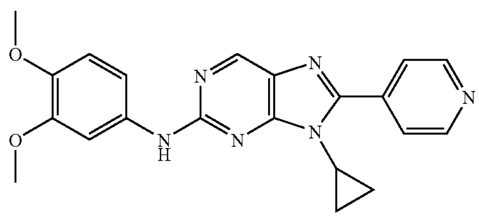 | 4.06 min/ Method C | 389.2 |
| 48 | 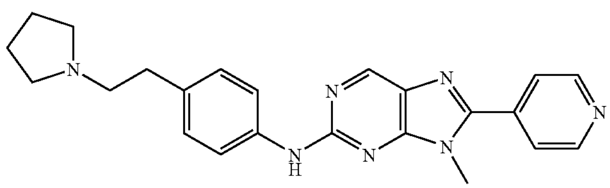 | 1.23 min/ Method B | 400.2 |
| 49 | 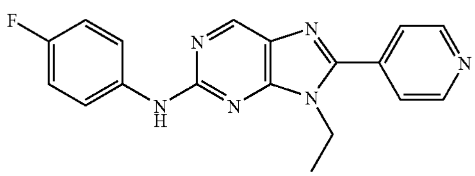 | 4.90 min/ Method A | 335.2 |
| 50 | 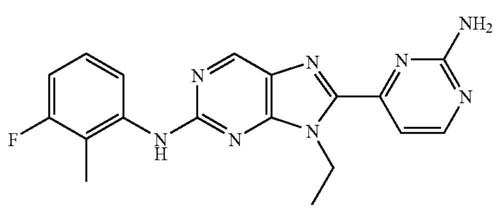 | 5.59 min/ Method B | 365.3 |
| 51 | 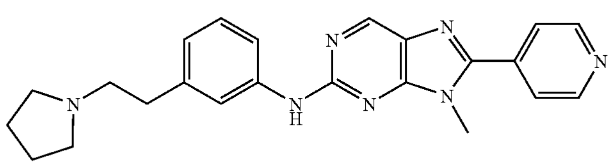 | 3.71 min/ Method B | 400.2 |
| 52 | 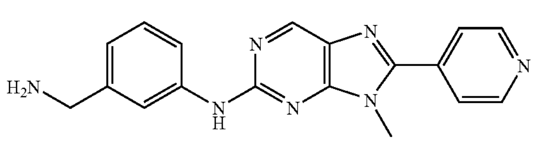 | 1.30 min/ Method A | 332.1 |

TABLE 1-continued
| Example | Structure | Hplc (min/Method) | m/z found ([M + H]+) |
|---|---|---|---|
| 53 | 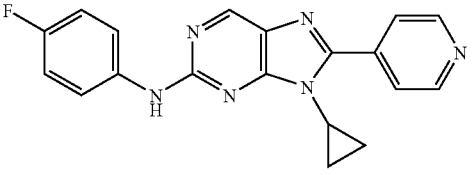 | 5.05 min/ Method C | 347.3 |
| 54 | 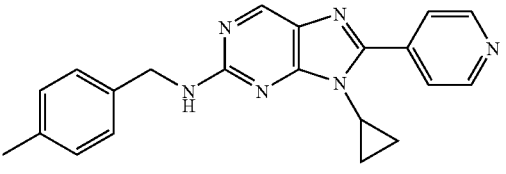 | 4.73 min/ Method A | 357.3 |
| 55 | 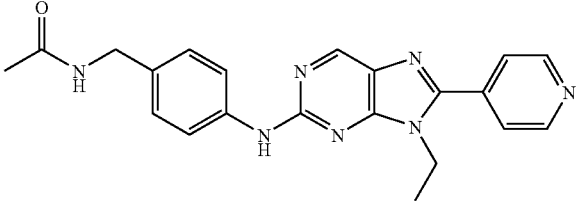 | 3.54 min/ Method A | 388.2 |
| 56 | 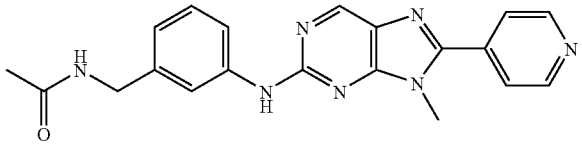 | 3.45 min/ Method A | 374.2 |
| 57 | 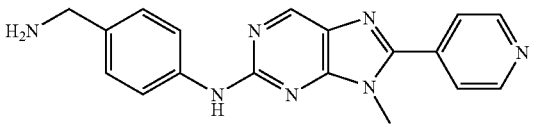 | 2.17 min/ Method A | 332.3 |
| 58 | 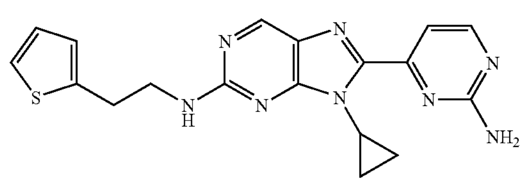 | 4.78 min/ Method A | 379.1 |
| 59 | 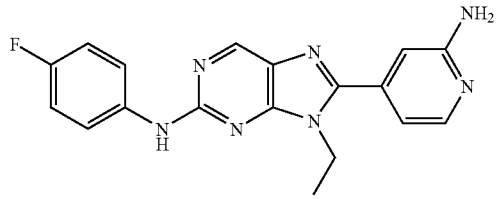 | 4.82 min/ Method A | 350.2 |
| 60 | 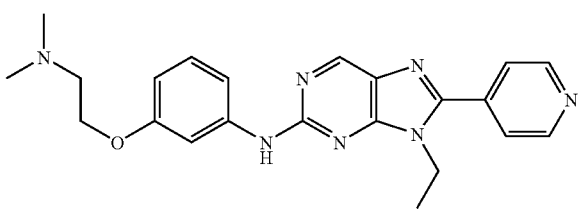 | 3.44 min/ Method A | 404.1 |

TABLE 1-continued

| Example | Structure | Hplc (min/Method) | m/z found ([M + H]+) |
|---|---|---|---|
| 61 | 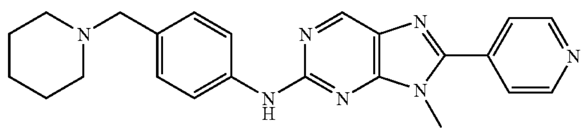 | 3.94 min/ Method B | 400.1 |
| 62 | 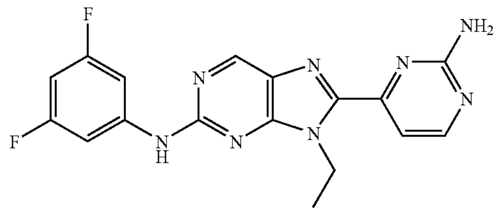 | 6.03 min/ Method B | 369.2 |
| 63 | 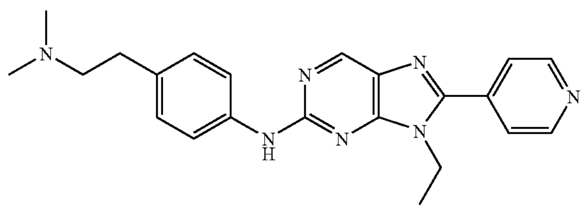 | 3.76 min/ Method B | 388.2 |
| 64 | 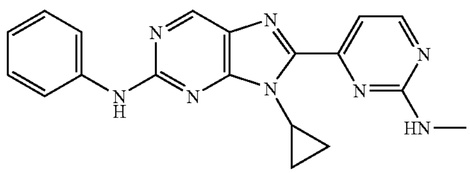 | 5.25 min/ Method A | 359.2 |
| 65 | 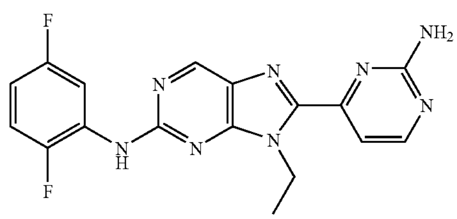 | 6.00 min/ Method B | 369.2 |
| 66 | 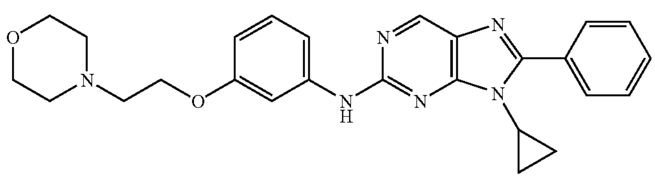 | 3.54 min/ Method A | 458.2 |
| 67 | 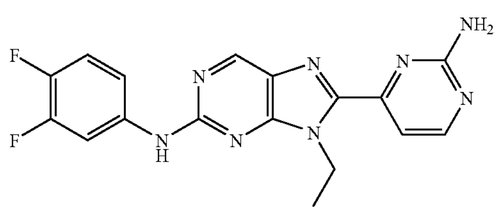 | 5.71 min/ Method B | 369.2 |
| 68 | 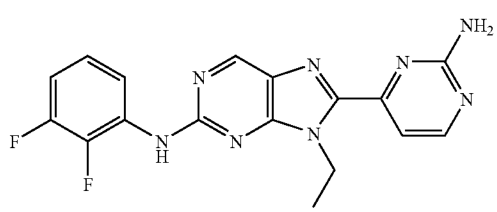 | 5.86 min/ Method B | 369.2 |

TABLE 1-continued

| Example | Structure | Hplc (min/Method) | m/z found ([M + H]+) |
|---|---|---|---|
| 69 | 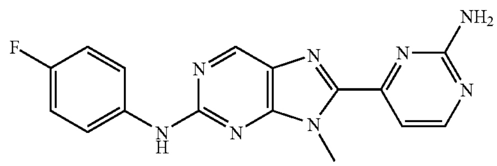 | 4.99 min/ Method A | 337.3 |
| 70 | 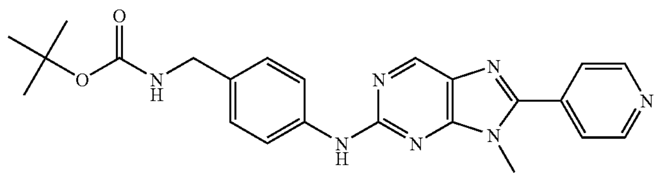 | 5.25 min/ Method A | 458.1 |
| 71 | 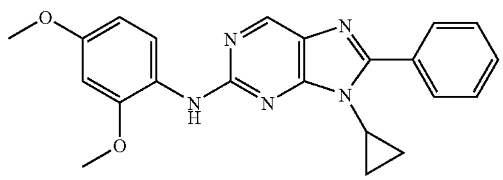 | 4.44 min/ Method B | 389.2 |
| 72 | 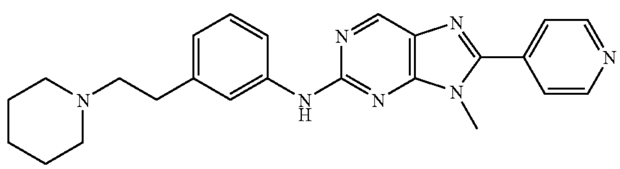 | 4.16 min/ Method B | 414.2 |
| 73 | 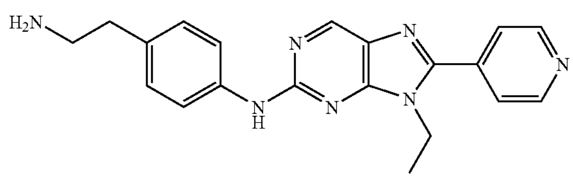 | 3.03 min/ Method A | 360.1 |
| 74 | 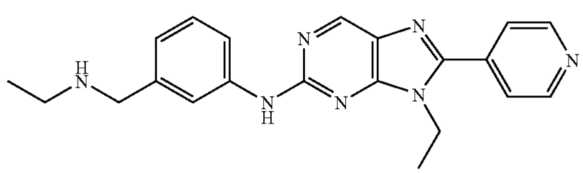 | 2.68 min/ Method B | 374.2 |
| 75 | 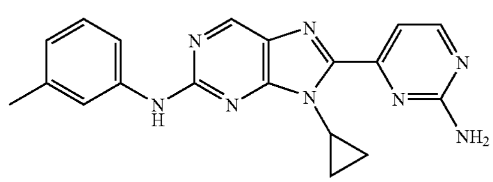 | 5.29 min/ Method A | 359.3 |
| 76 | 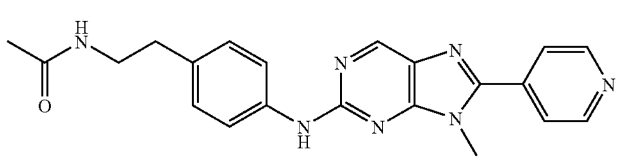 | 3.58 min/ Method A | 388.3 |

TABLE 1-continued
| Example | Structure | Hplc (min/Method) | m/z found ([M + H]+) |
|---|---|---|---|
| 77 | 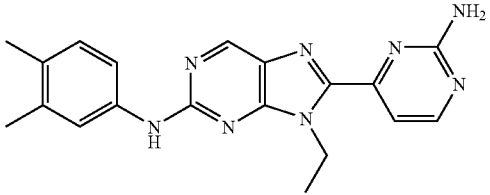 | 5.89 min/ Method B | 361.3 |
| 78 | 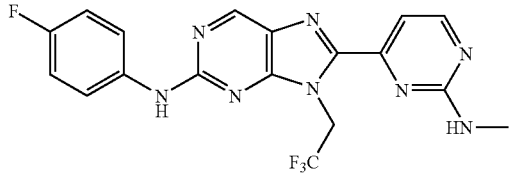 | 6.24 min/ Method A | 419.2 |
| 79 | 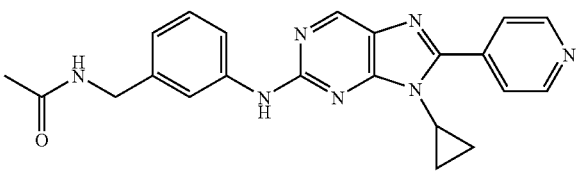 | 3.79 min/ Method A | 400.2 |
| 80 | 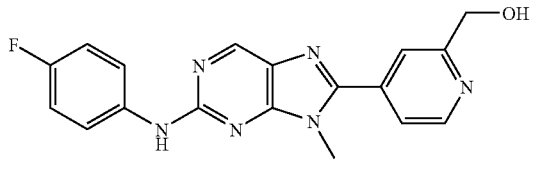 | 4.49 min/ Method A | 351.2 |
| 81 | 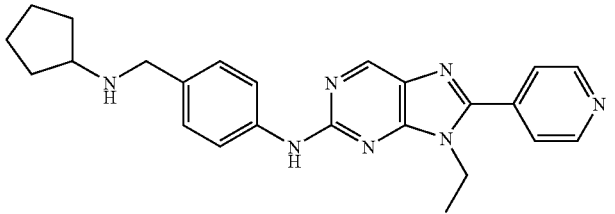 | 4.33 min/ Method B | 414.2 |
| 82 | 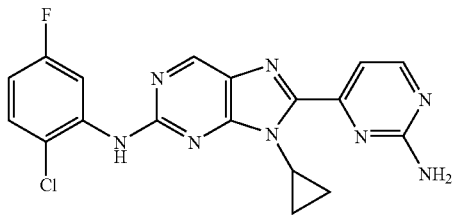 | 6.18 min/ Method B | 397.2 |
| 83 | 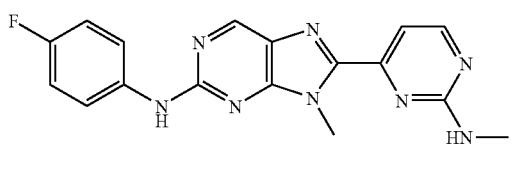 | 5.30 min/ Method A | 351.3 |
| 84 | 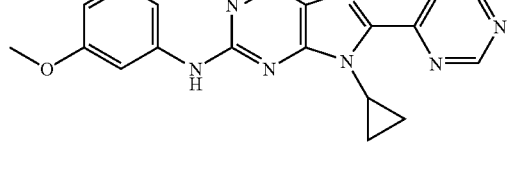 | 5.24 min/ Method A | 360.2 |

TABLE 1-continued
| Example | Structure | Hplc (min/Method) | m/z found ([M + H]+) |
|---|---|---|---|
| 85 | 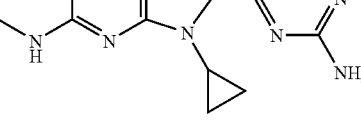 | 3.93 min/ Method B | 388.3 |
| 86 | 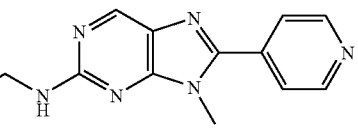 | 4.04 min/ Method B | 337.1 |
| 87 | 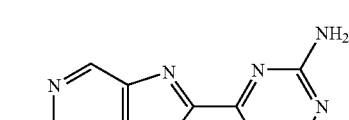 | 5.62 min/ Method B | 361.1 |
| 88 | 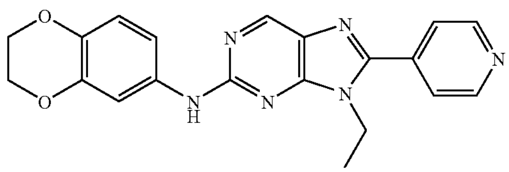 | 4.45 min/ Method A | 375.3 |
| 89 | 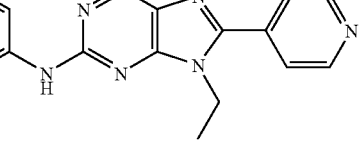 | 5.77 min/ Method A | 373.2 |
| 90 | 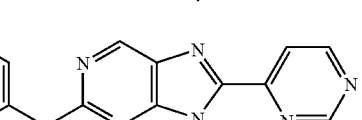 | 5.92 min/ Method A | 375.3 |
| 91 | 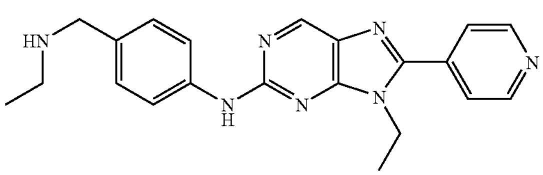 | 3.90 min/ Method B | 374.2 |
| 92 | 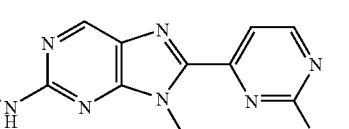 | 1.38 min/ Method B | 416.2 |

TABLE 1-continued

| Example | Structure | Hplc (min/Method) | m/z found ([M + H]+) |
|---|---|---|---|
| 93 | 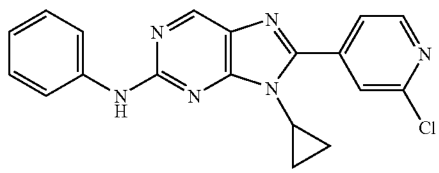 | 6.47 min/ Method A | 363.2 |
| 94 | 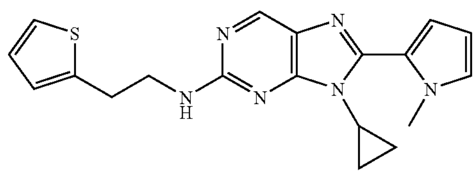 | 5.87 min/ Method A | 365.2 |
| 95 | 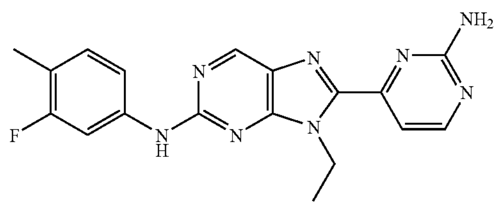 | 5.85 min/ Method B | 365.3 |
| 96 | 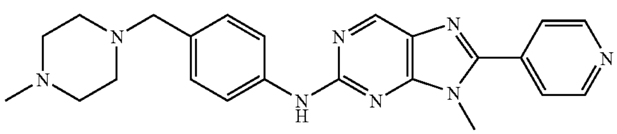 | 1.04 min/ Method B | 415.2 |
| 97 | 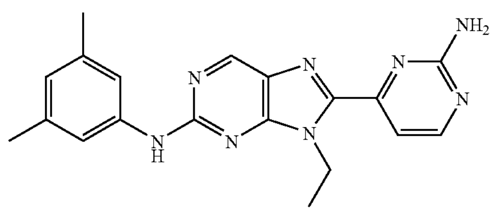 | 5.90 min/ Method B | 361.3 |
| 98 | 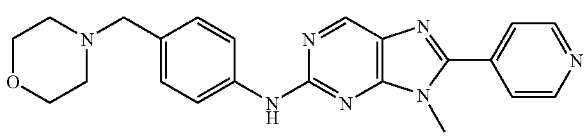 | 1.11 min/ Method B | 402.3 |
| 99 | 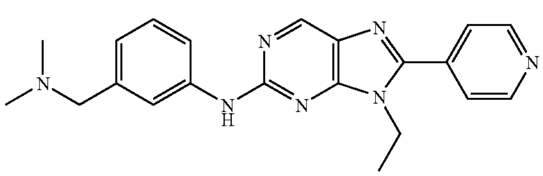 | 1.47 min/ Method B | 374.2 |
| 100 | 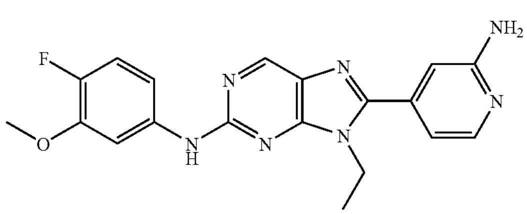 | 4.90 min/ Method A | 380.2 |

TABLE 1-continued

| Example | Structure | Hplc (min/Method) | m/z found ([M + H]$^+$) |
|---|---|---|---|
| 101 | 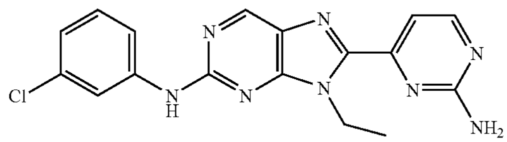 | 5.69 min/ Method A | 367.2 |
| 102 | 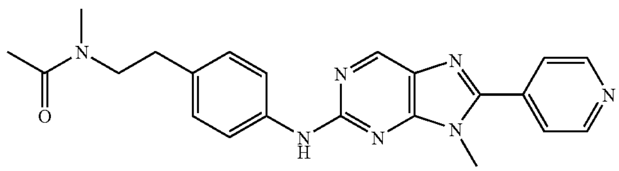 | 3.92 min/ Method A | 402.3 |
| 103 | 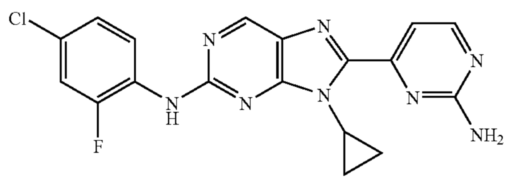 | 6.07 min/ Method B | 397.2 |
| 104 | 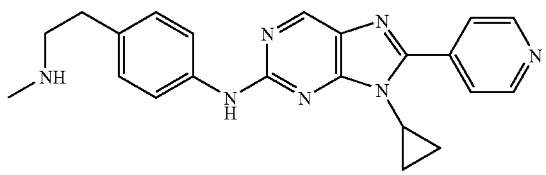 | 3.16 min/ Method A | 386.2 |
| 105 | 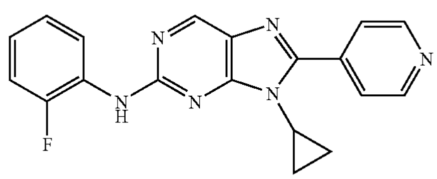 | 4.88 min/ Method A | 347.2 |
| 106 | 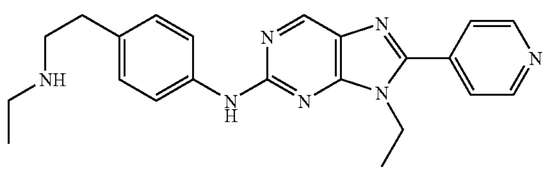 | 3.82 min/ Method B | 388.2 |
| 107 | 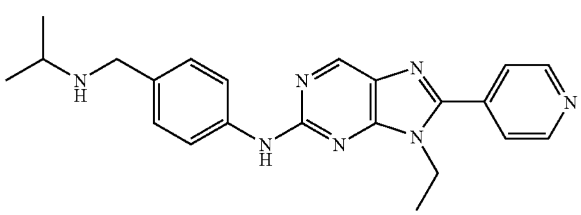 | 4.06 min/ Method B | 388.2 |
| 108 | 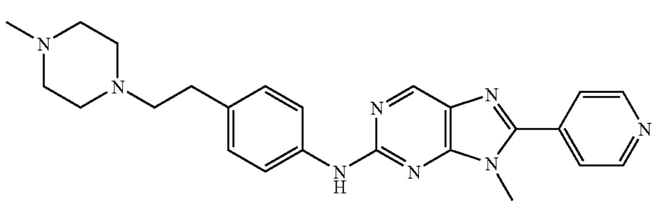 | 1.10 min/ Method B | 429.2 |

TABLE 1-continued

| Example | Structure | Hplc (min/Method) | m/z found ([M + H]+) |
|---|---|---|---|
| 109 | 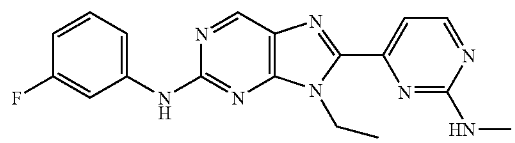 | 5.71 min/ Method A | 365.3 |
| 110 | 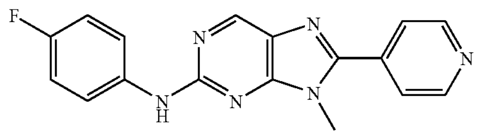 | 4.62 min/ Method A | 321.3 |
| 111 | 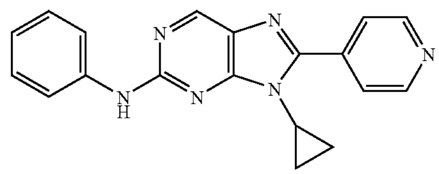 | 4.67 min/ Method A | 329.2 |
| 112 | 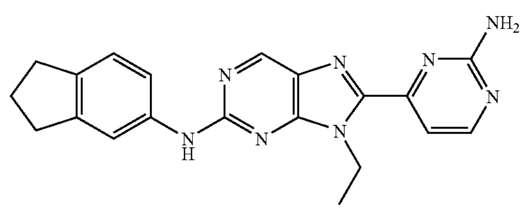 | 5.97 min/ Method B | 373.3 |
| 113 | 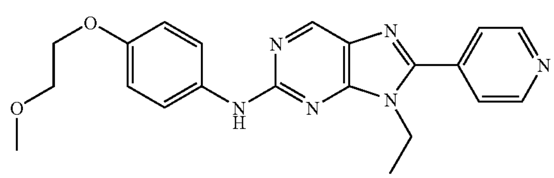 | 4.36 min/ Method A | 391.2 |
| 114 | 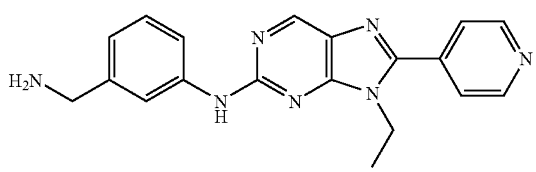 | 2.37 min/ Method A | 346.1 |
| 115 | 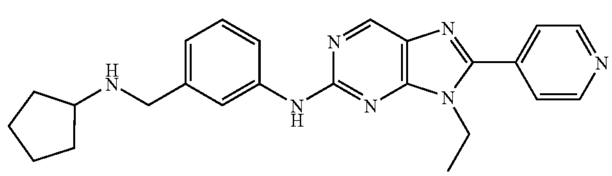 | 4.39 min/ Method B | 414.2 |
| 116 | 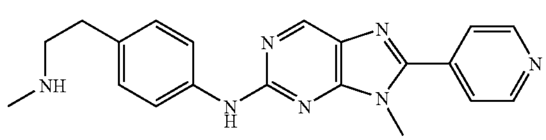 | 1.00 min/ Method A | 360.1 |
| 117 | 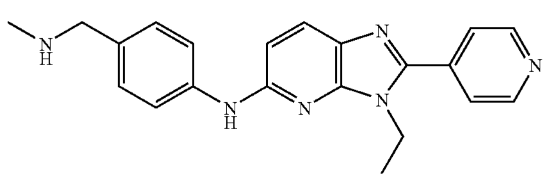 | 3.44 min/ Method A | 359.2 |

TABLE 1-continued

| Example | Structure | Hplc (min/Method) | m/z found ([M + H]+) |
|---|---|---|---|
| 118 | 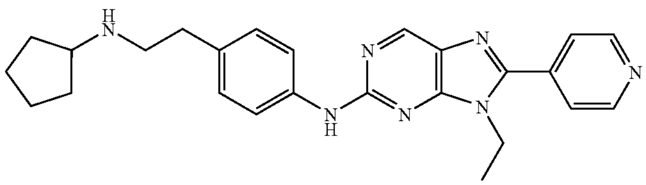 | 4.41 min/ Method B | 428.3 |
| 119 | 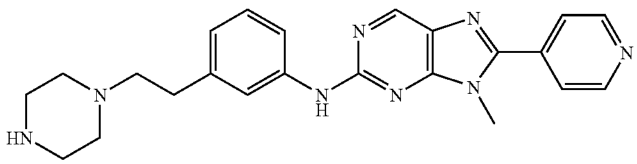 | 0.95 min/ Method B | 415.2 |
| 120 | 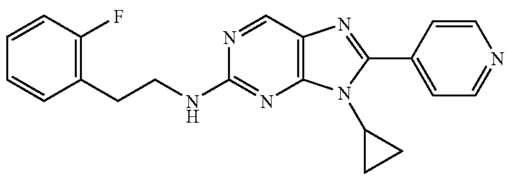 | 4.53 min/ Method B | 375.2 |
| 121 | 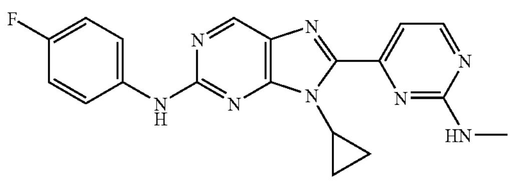 | 5.40 min/ Method A | 377.2 |
| 122 | 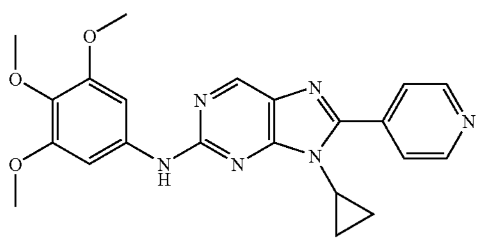 | 4.25 min/ Method C | 419.2 |
| 123 | 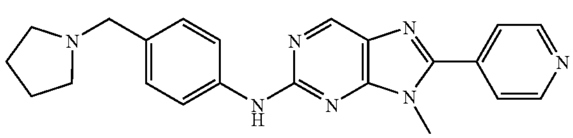 | 1.11 min/ Method B | 386.2 |
| 124 | 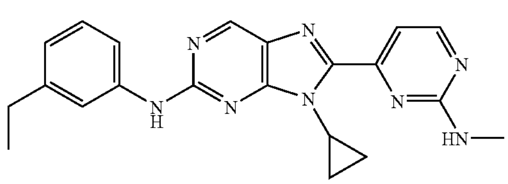 | 5.82 min/ Method A | 387.3 |
| 125 | 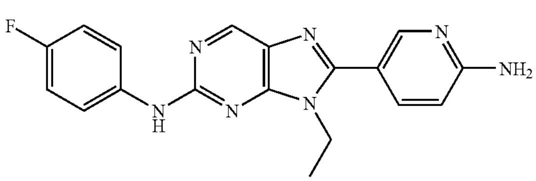 | 4.54 min/ Method A | 350.2 |

TABLE 1-continued
| Example | Structure | Hplc (min/Method) | m/z found ([M + H]+) |
|---|---|---|---|
| 126 | 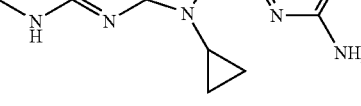 | 4.17 min/ Method B | 388.3 |
| 127 | 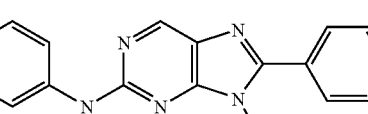 | 3.95 min/ Method B | 386.2 |
| 128 | 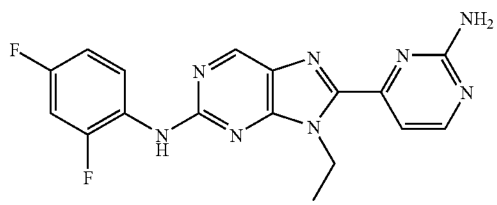 | 5.75 min/ Method B | 369.2 |
| 129 | 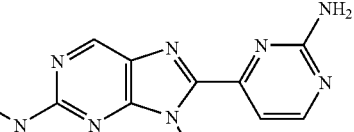 | 4.65 min/ Method C | 389.2 |
| 130 | 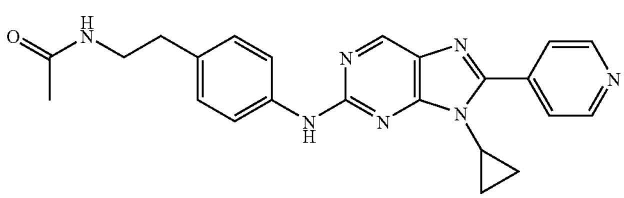 | 3.84 min/ Method A | 414.2 |
| 131 | 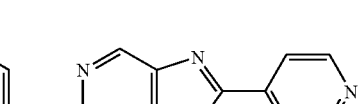 | 4.13 min/ Method A | 416.3 |
| 132 | 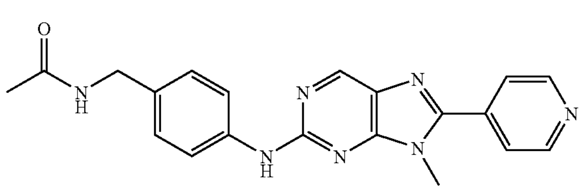 | 3.07 min/ Method A | 374.2 |

TABLE 1-continued

| Example | Structure | Hplc (min/Method) | m/z found ([M + H]$^+$) |
|---|---|---|---|
| 133 | 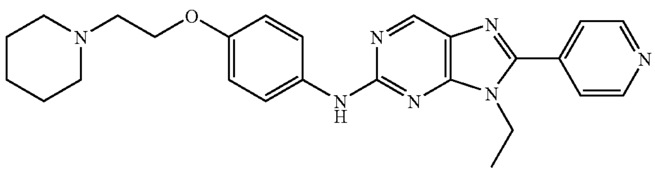 | 3.59 min/ Method A | 444.2 |
| 134 | 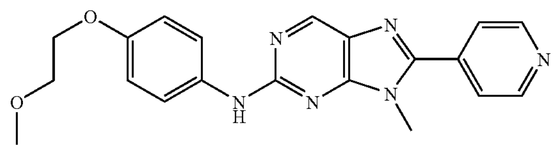 | 4.10 min/ Method A | 377.3 |
| 135 | 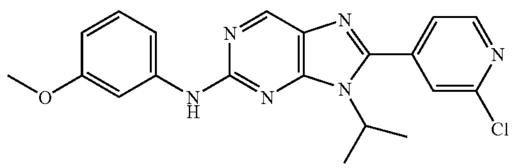 | 6.72 min/ Method A | 395.1 |
| 136 | 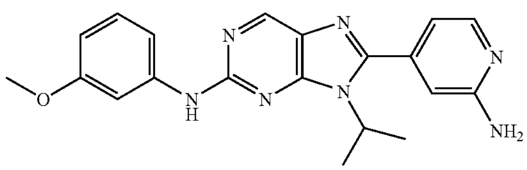 | 4.96 min/ Method A | 376.5 |
| 137 | 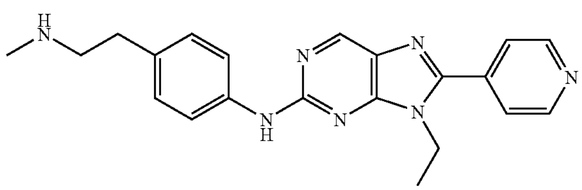 | 3.12 min/ Method A | 374.2 |
| 138 | 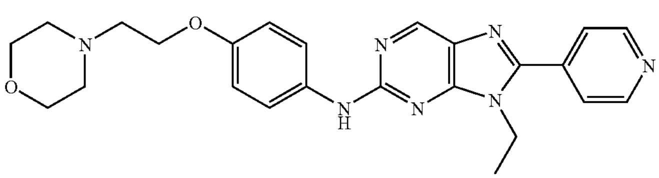 | 3.15 min/ Method A | 446.2 |
| 139 | 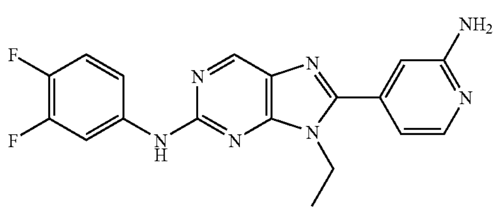 | 5.18 min/ Method A | 368.3 |
| 140 | 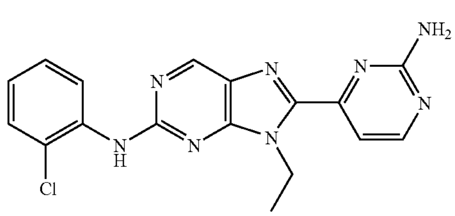 | 6.13 min/ Method B | 367.2 |

TABLE 1-continued

| Example | Structure | Hplc (min/Method) | m/z found ([M + H]+) |
|---------|-----------|-------------------|----------------------|
| 141 | 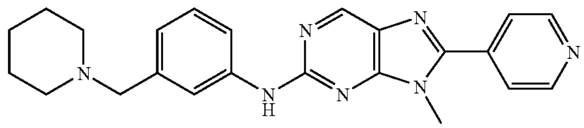 | 4.08 min/ Method B | 400.2 |
| 142 | 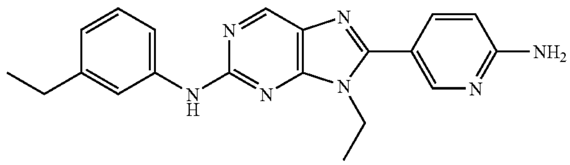 | 4.98 min/ Method A | 360.3 |
| 143 | 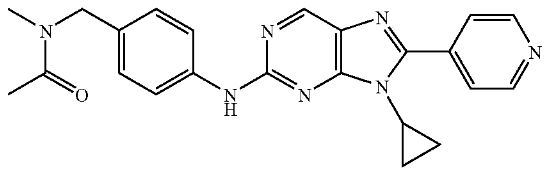 | 3.99 min/ Method A | 414.2 |
| 144 | 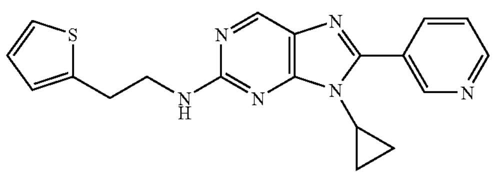 | 3.63 min/ Method A | 363.2 |
| 145 | 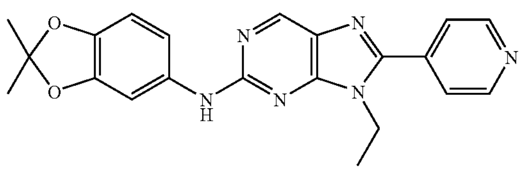 | 5.10 min/ Method A | 389.2 |
| 146 | 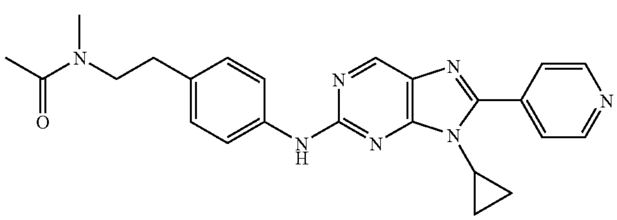 | 4.18 min/ Method A | 428.3 |
| 147 | 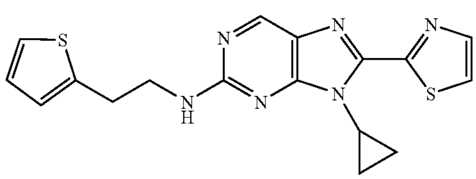 | 5.70 min/ Method A | 369.1 |
| 148 | 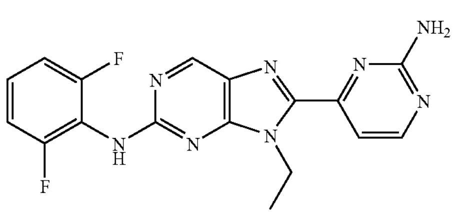 | 5.23 min/ Method A | 369.3 |

TABLE 1-continued

| Example | Structure | Hplc (min/Method) | m/z found ([M + H]+) |
|---|---|---|---|
| 149 | 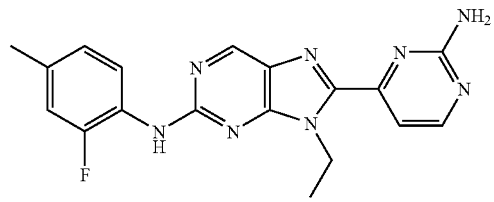 | 5.86 min/ Method B | 365.3 |
| 150 | 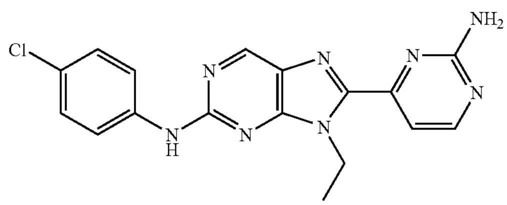 | 5.85 min/ Method B | 367.3 |
| 151 | 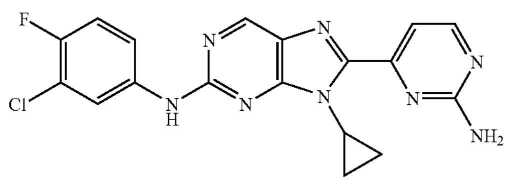 | 5.73 min/ Method A | 397.2 |
| 152 | 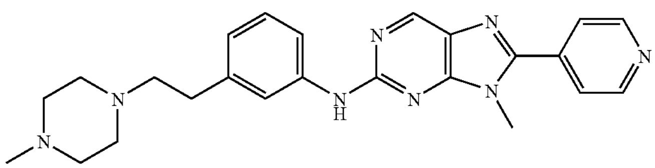 | 1.13 min/ Method B | 429.2 |
| 153 | 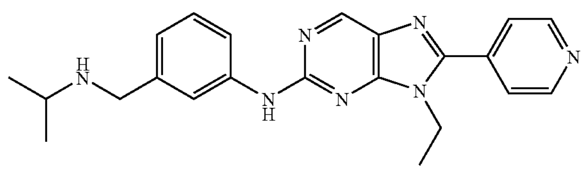 | 3.86 min/ Method B | 388.2 |
| 154 | 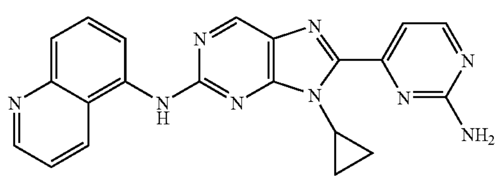 | 3.94 min/ Method B | 396.3 |
| 155 | 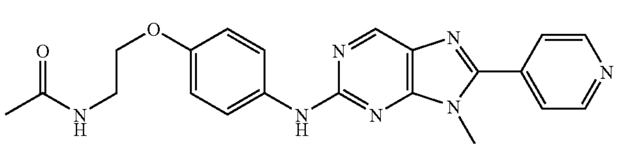 | 3.37 min/ Method A | 404.3 |
| 156 | 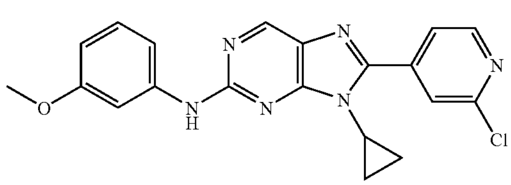 | 6.47 min/ Method A | 393.2 |

TABLE 1-continued

| Example | Structure | Hplc (min/Method) | m/z found ([M + H]+) |
|---|---|---|---|
| 157 | 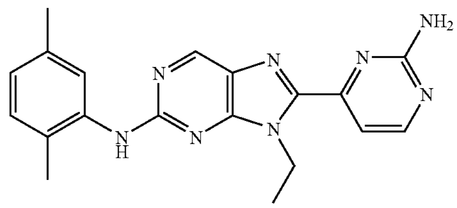 | 5.77 min/ Method B | 361.1 |
| 158 | 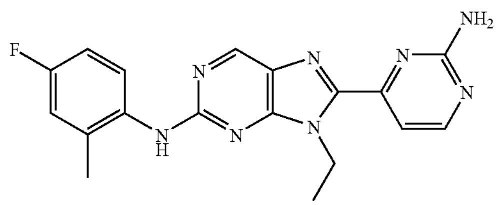 | 5.44 min/ Method B | 365.3 |
| 159 | 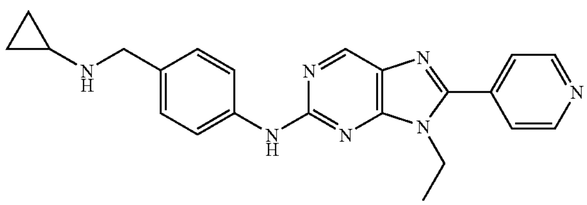 | 1.52 min/ Method B | 386.3 |
| 160 | 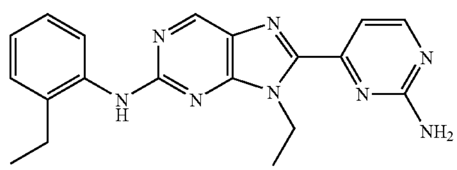 | 5.90 min/ Method B | 361.3 |
| 161 | 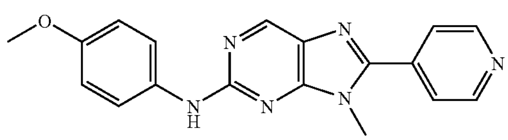 | 4.00 min/ Method B | 333.2 |
| 162 | 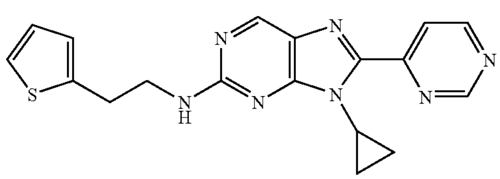 | 5.34 min/ Method A | 364.1 |
| 163 | 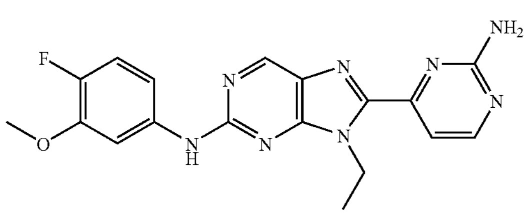 | 5.29 min/ Method A | 381.2 |
| 164 | 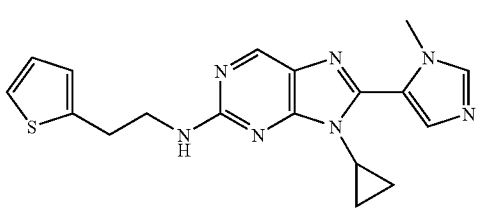 | 4.30 min/ Method A | 366.2 |

TABLE 1-continued

| Example | Structure | Hplc (min/Method) | m/z found ([M + H]+) |
|---|---|---|---|
| 165 | 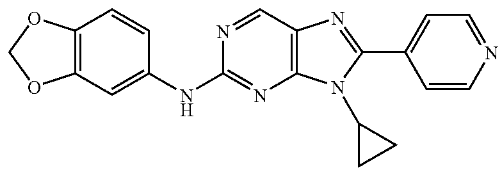 | 4.35 min/ Method C | 373.3 |
| 166 | 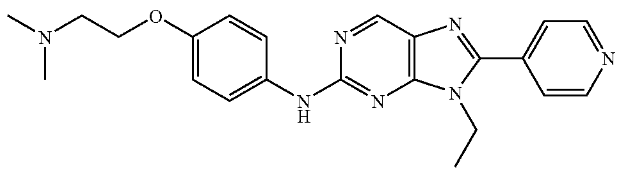 | 3.21 min/ Method A | 404.2 |
| 167 | 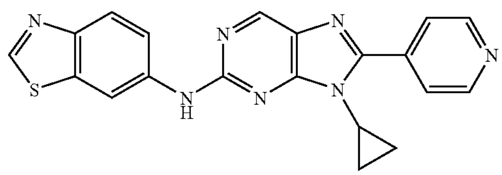 | 4.46 min/ Method A | 386.2 |
| 168 | 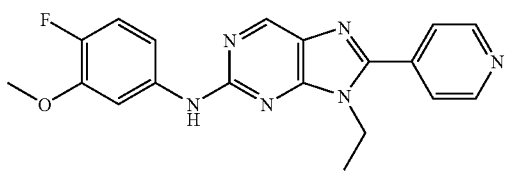 | 4.98 min/ Method A | 365.3 |
| 169 | 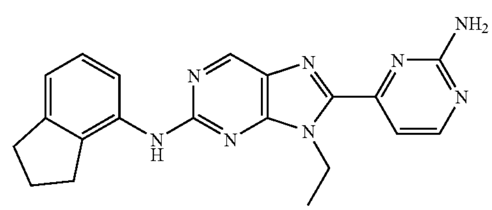 | 5.95 min/ Method B | 373.3 |
| 170 | 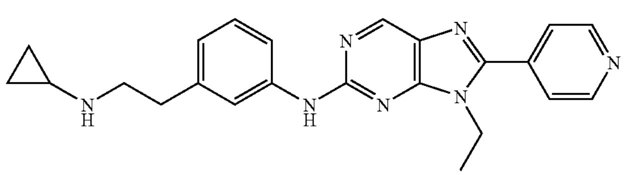 | 2.87 min/ Method A | 400.2 |
| 171 | 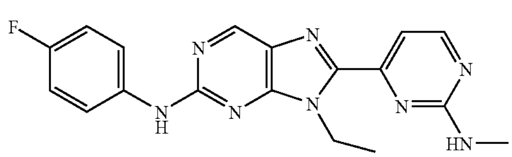 | 5.52 min/ Method A | 365.2 |
| 172 | 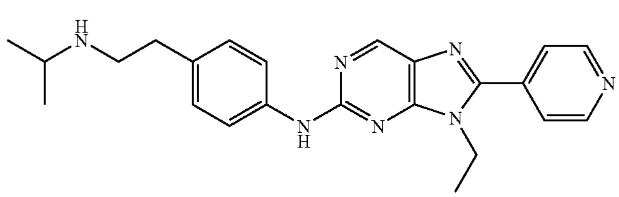 | 4.08 min/ Method B | 402.2 |

TABLE 1-continued

| Example | Structure | Hplc (min/Method) | m/z found ([M + H]+) |
|---|---|---|---|
| 173 | 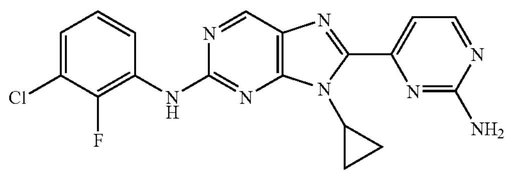 | 5.91 min/ Method B | 397.2 |
| 174 | 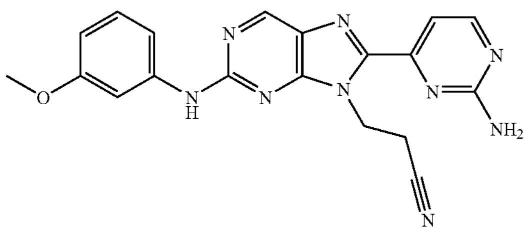 | 4.89 min/ Method A | 388.2 |
| 175 | 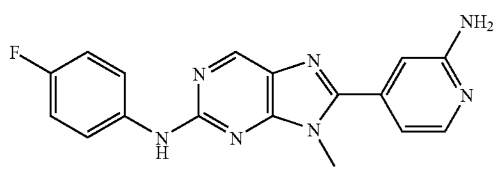 | 4.65 min/ Method A | 336.3 |
| 176 | 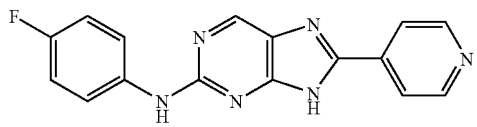 | 4.42 min/ Method A | 307.2 |
| 177 | 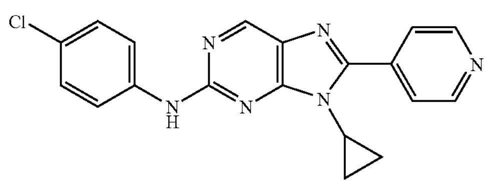 | 4.61 min/ Method B | 363.2 |
| 178 | 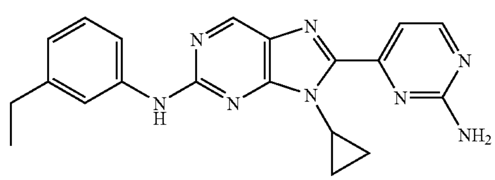 | 5.56 min/ Method A | 373.3 |
| 179 | 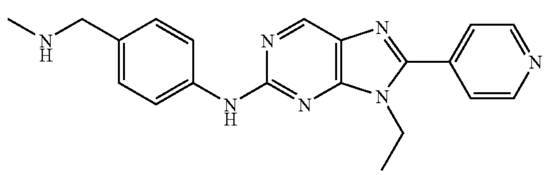 | 3.28 min/ Method A | 360.2 |
| 180 | 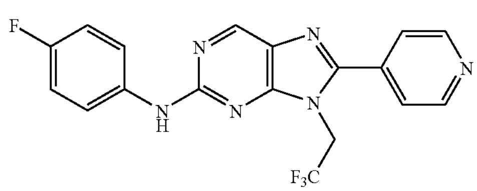 | 5.56 min/ Method A | 389.3 |

TABLE 1-continued

| Example | Structure | Hplc (min/Method) | m/z found ([M + H]+) |
|---|---|---|---|
| 181 | 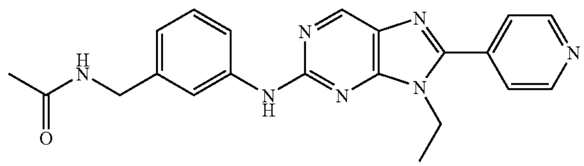 | 3.77 min/ Method A | 388.3 |
| 182 | 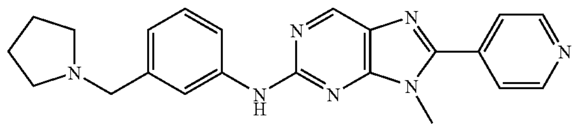 | 1.50 min/ Method B | 386.2 |
| 183 | 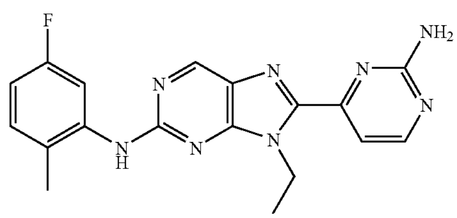 | 5.73 min/ Method B | 365.3 |
| 184 | 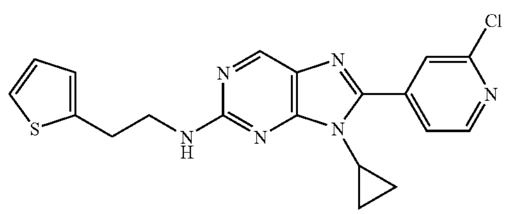 | 5.84 min/ Method A | 397.1 |
| 185 | 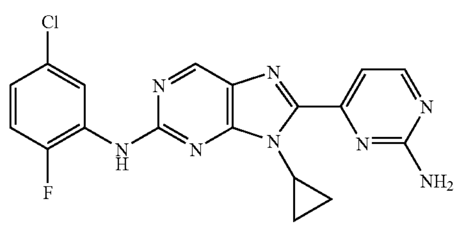 | 6.02 min/ Method B | 397.2 |
| 186 | 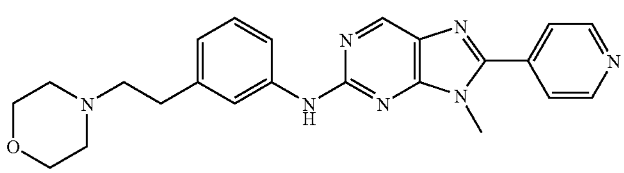 | 1.62 min/ Method B | 416.2 |
| 187 | 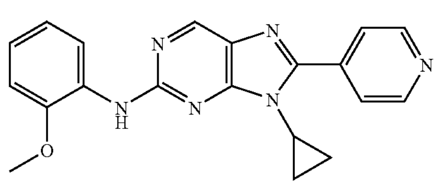 | 4.69 min/ Method B | 359.2 |
| 188 | 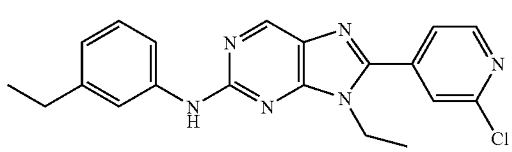 | 7.14 min/ Method A | 379.2 |

TABLE 1-continued

| Example | Structure | Hplc (min/Method) | m/z found ([M + H]+) |
|---------|-----------|-------------------|----------------------|
| 189 | 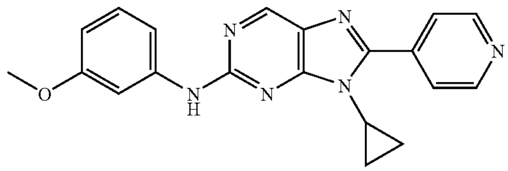 | 4.54 min/ Method C | 359.2 |
| 190 | 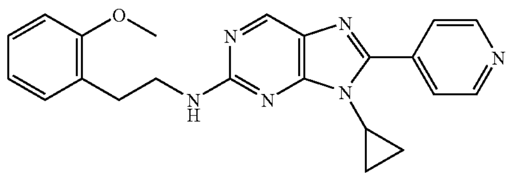 | 4.54 min/ Method B | 387.2 |
| 191 | 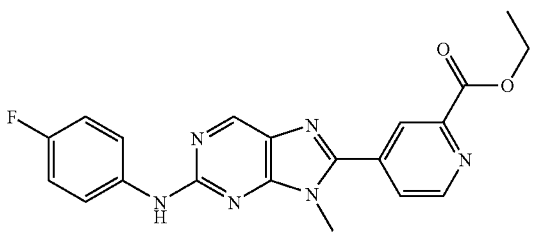 | 5.87 min/ Method A | 393.2 |
| 192 | 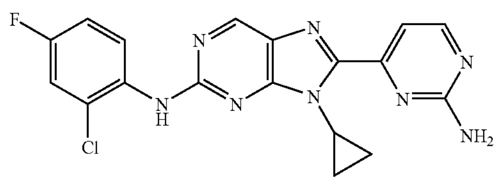 | 6.01 min/ Method B | 397.2 |
| 193 | 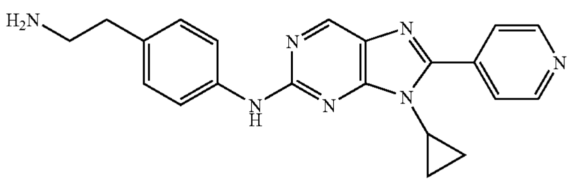 | 2.49 min/ Method A | 372.1 |
| 194 | 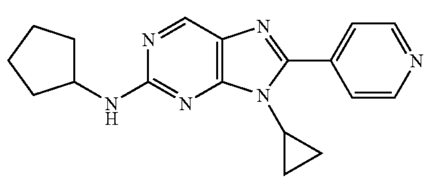 | 4.39 min/ Method A | 321.2 |
| 195 | 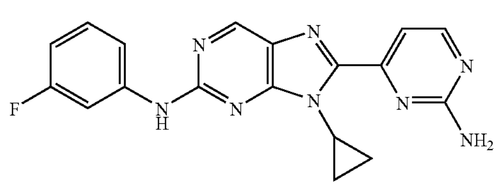 | 5.37 min/ Method A | 363.3 |
| 196 | 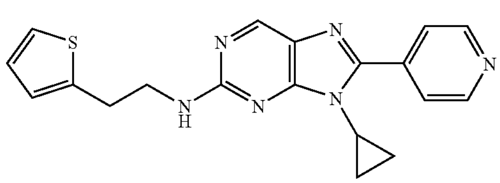 | 4.60 min/ Method A | 363.3 |

TABLE 1-continued

| Example | Structure | Hplc (min/Method) | m/z found ([M + H]+) |
|---|---|---|---|
| 197 | 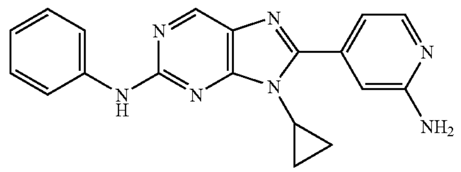 | 4.81 min/ Method A | 344.3 |
| 198 | 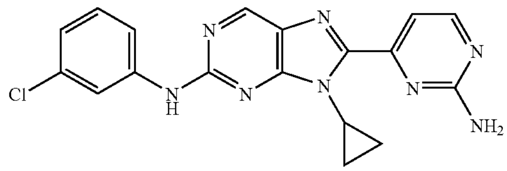 | 5.77 min/ Method A | 379.2 |
| 199 | 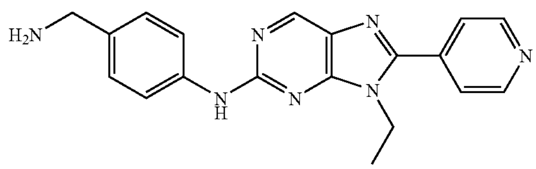 | 3.13 min/ Method A | 346.2 |
| 200 | 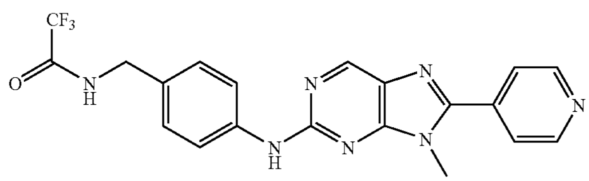 | 4.61 min/ Method A | 428.2 |
| 201 | 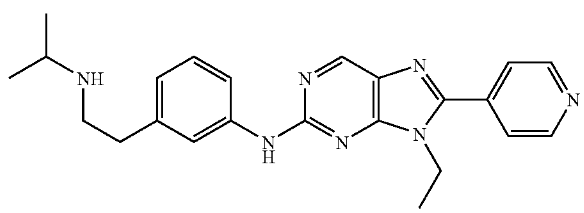 | 4.23 min/ Method B | 402.3 |
| 202 | 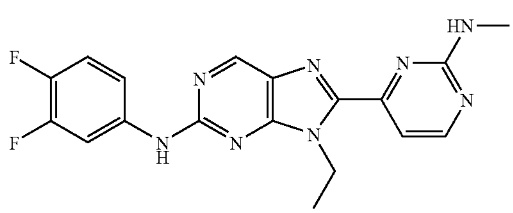 | 5.89 min/ Method A | 383.3 |
| 203 | 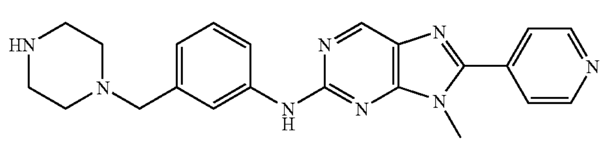 | 1.62 min/ Method B | 401.2 |
| 204 | 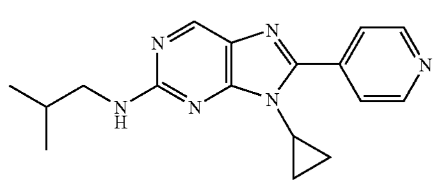 | 4.13 min/ Method A | 309.4 |

TABLE 1-continued

| Example | Structure | Hplc (min/Method) | m/z found ([M + H]+) |
|---|---|---|---|
| 205 | 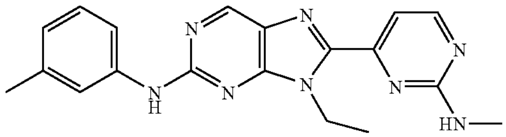 | 5.60 min/ Method A | 361.3 |
| 206 | 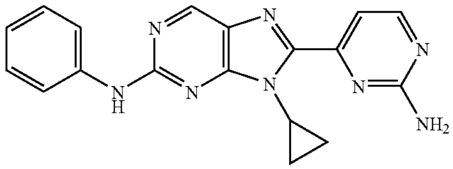 | 4.98 min/ Method A | 345.2 |
| 207 | 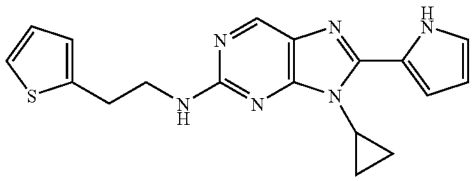 | 5.68 min/ Method A | 351.1 |
| 208 | 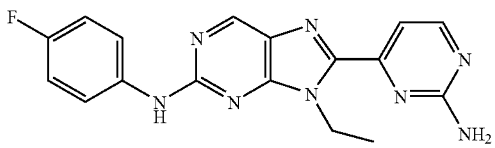 | 5.22 min/ Method A | 351.2 |
| 209 | 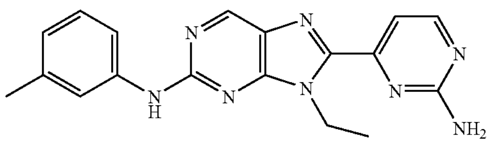 | 5.28 min/ Method A | 347.3 |
| 210 | 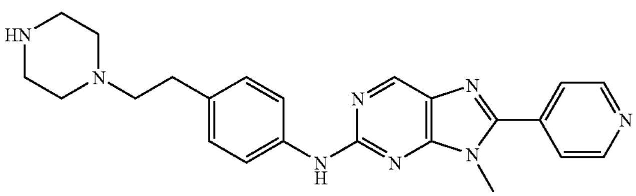 | 1.08 min/ Method B | 415.2 |
| 211 | 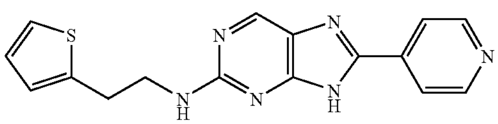 | 4.60 min/ Method A | 323.2 |
| 212 | 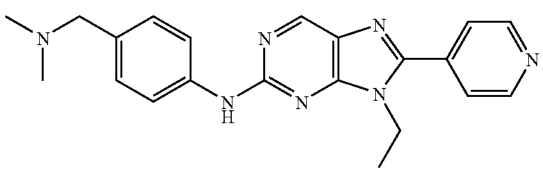 | 1.14 min/ Method B | 374.2 |
| 213 | 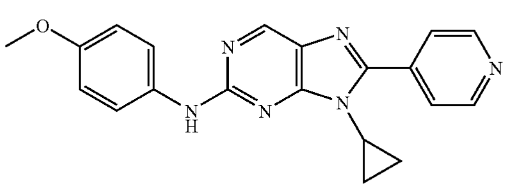 | 4.48 min/ Method C | 359.2 |

| Example | Structure | Hplc (min/Method) | m/z found ([M + H]+) |
|---|---|---|---|
| 214 | 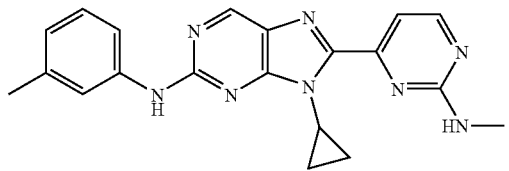 | 6.02 min/ Method B | 387.3 |

NMR Analysis:

9-Cyclopropyl-8-(2-(methylamino)pyrimidin-4-yl)-N-m-tolyl-9H-purin-2-amine

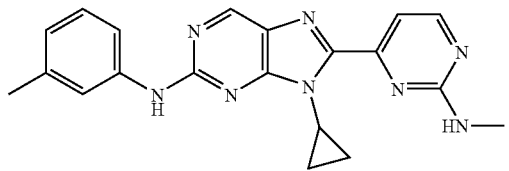

($\delta_H$, 300 MHz, CD$_3$OD) 1.39 (m, 4H), 2.53 (s, 3H), 3.24 (s, 3H), 3.98 (m, 1H), 7.03 (m, 1H), 7.36 (m, 1H), 7.69 (m, 2H), 7.89 (s, 1H), 8.54 (m, 1H), 8.96 (s, 1H); m/z (ESI) 373.3 [M+H]+.

N-(4-(9-Methyl-8-(pyridin-4-yl)-9H-purin-2-ylamino)benzyl)-N-methylacetamide

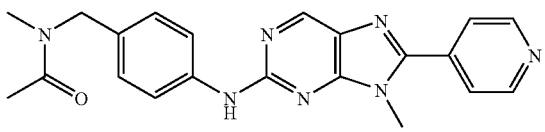

($\delta_H$, 300 MHz, CD$_3$OD, Rotational Isomers) [2.18 (s) & 2.20 (s), 3H, rotational isomers], [2.94 (s) & 3.02 (s), 3H, rotational isomers], [4.05 (s) & 4.05 (s), 3H, rotational isomers], [4.57 (s) & 4.61 (s), 2H, rotational isomers], 7.24 (m, 2H), [7.79 (d) & 7.85 (d), 2H, rotational isomers], 8.39 (m, 2H), [8.87 (s) & 8.89 (s), 1H, rotational isomers], 8.93 (d, 2H); m/z (ESI) 388.2 [M+H]+.

8-(2-Aminopyridin-4-yl)-9-cyclopropyl-N-(3-methoxyphenyl)-9H-purin-2-amine

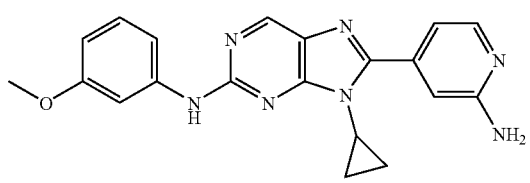

($\delta_H$, 300 MHz, CD$_3$OD) 1.23 (m, 2H), 1.46 (m, 2H), 3.79 (m, 1H), 3.99 (s, 3H), 6.76 (m, 1H), 7.37 (m, 1H), 7.46 (m, 1H), 7.68 (m, 1H), 7.84 (m, 2H), 8.12 (m, 1H), 8.97 (s, 1H); m/z (ESI) 374.2 [M+H]+.

8-(2-Aminopyrimidin-4-yl)-9-ethyl-N-(4-fluoro-3-methylphenyl)-9H-purin-2-amine

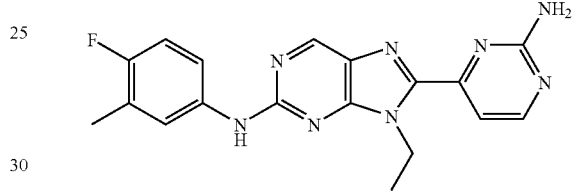

($\delta_H$, 400 MHz, d$_6$DMSO) 1.40 (t, 3H), 2.21 (s, 3H), 4.78 (q, 2H), 7.08 (m, 1H), 7.20 (bs, 2H), 7.38 (d, 1H), 7.67 (m, 1H), 7.77 (m, 1H), 8.40 (d, 1H), 8.92 (s, 1H), 9.90 (s, 1H); m/z (ESI) 365.3 [M+H]+.

tert-Butyl 4-(9-cyclopropyl-8-(pyridin-4-yl)-9H-purin-2-ylamino)phenethyl carbamate

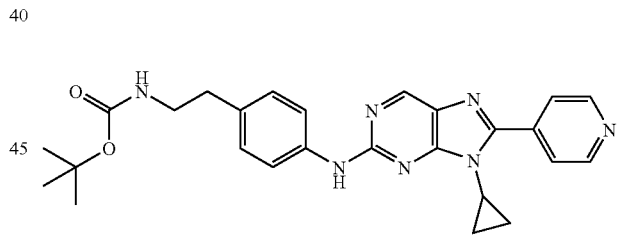

($\delta_H$, 300 MHz, CD$_3$OD) 1.01 (m, 2H), 1.27 (m, 2H), 1.44 (s, 9H), 2.78 (t, 2H), 3.27 (t, 2H), 3.72 (m, 1H), 7.21 (m, 2H), 7.79 (m, 2H), 8.37 (m, 2H), 8.82 (s, 1H), 8.86 (d, 2H); m/z (ESI) 472.1 [M+H]+.

9-Cyclopropyl-N-(3-fluorophenyl)-8-(2-(methylamino)pyrimidin-4-yl)-9H-purin-2-amine

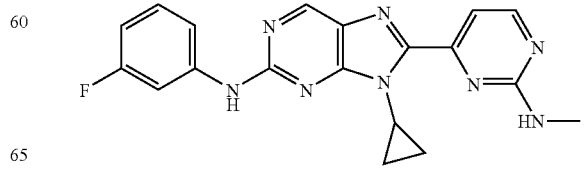

(δ$_H$, 300 MHz, CD$_3$OD) 1.21 (m, 4H), .09 (s, 3H), 3.79 (m, 1H), 6.69 (m, 1H), 7.25 (m, 1H), 7.34 (m, 1H), 7.63 (m, 1H), 7.96 (m, 1H), 8.31 (m, 1H), 8.86 (s, 1H); m/z (ESI) 377.4 [M+H]$^+$.

N-(4-(9-Ethyl-8-(pyridin-4-yl)-9H-purin-2-ylamino)benzyl)-N-methylacetamide

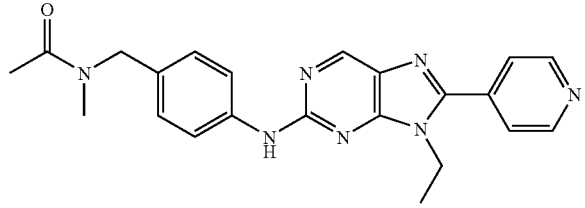

(δ$_H$, 300 MHz, CD$_3$OD, Rotational Isomers) 1.54 (t, 3H), [2.18 (s) & 2.20 (s), 3H, rotational isomers], [2.94 (s) & 3.02 (s), 3H, rotational isomers], 3.50 (m, 2H), [4.57 (s) & 4.61 (s), 2H, rotational isomers], 7.25 (m, 2H), [7.79 (d) & 7.85 (d), 2H, rotational isomers], 8.27 (m, 2H), [8.88 (s) & 8.89 (s), 1H, rotational isomers], 8.93 (d, 2H); m/z (ESI) 402.2 [M+H]$^+$.

8-(2-Aminopyrimidin-4-yl)-9-ethyl-N-(4-ethylphenyl)-9H-purin-2-amine

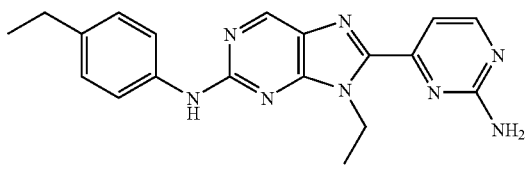

(δ$_H$, 400 MHz, d$_6$DMSO) 1.16 (t, 3H), 1.40 (t, 3H), 2.56 (q, 2H), 4.80 (q, 2H), 6.95 (bs, 2H), 7.14 (d, 2H), 7.35 (d, 1H), 7.75 (d, 2H), 8.40 (d, 1H), 8.90 (s, 1H), 9.72 (s, 1H); m/z (ESI) 361.2 [M+H]$^+$.

9-Methyl-N-(3-((4-methylpiperazin-1-yl)methyl)phenyl)-8-(pyridin-4-yl)-9H-purin-2-amine

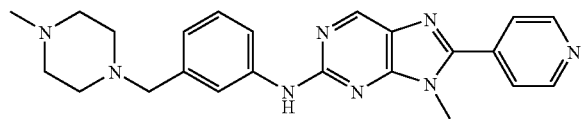

(δ$_H$, 300 MHz, CD$_3$OD) 2.93 (s, 3H), 3.31 (m, 4H), 3.48 (m, 4H), 4.06 (s, 3H), 4.14 (s, 2H), 7.14 (d, 1H), 7.42 (m, 1H), 7.87 (dd, 1H), 7.95 (d, 1H), 8.38 (d, 2H), 8.91 (s, 1H), 8.93 (d, 2H); m/z (ESI) 415.2 [M+H]$^+$.

9-Cyclopropyl-8-(pyridin-4-yl)-N-(3-(trifluoromethoxy)phenyl)-9H-purin-2-amine

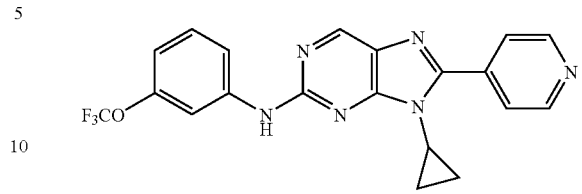

(δ$_H$, 300 MHz, CD$_3$OD) 1.01 (m, 2H), 1.30 (m, 2H), 3.76 (m, 1H), 6.91 (dd, 1H), 7.39 (m, 1H), 7.60 (dd, 1H), 8.29 (s, 1H), 8.40 (d, 2H), 8.87 (m, 3H); m/z (ESI) 413.2 [M+H]$^+$.

9-Ethyl-N-(3-(2-morpholinoethoxy)phenyl)-8-(pyridin-4-yl)-9H-purin-2-amine

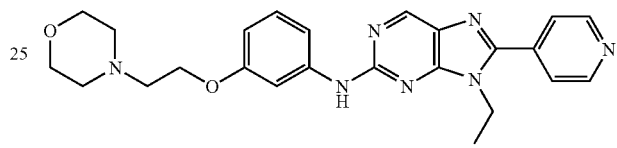

(δ$_H$, 300 MHz, CD$_3$OD) 1.55 (t, 3H), 3.20 (m, 2H), 3.61 (m, 2H), 3.68 (t, 2H), 3.70 (m, 2H), 3.85 (m, 2H), 4.44 (t, 2H), 4.50 (q, 2H), 7.72 (dd, 1H), 7.32 (m, 1H), 7.48 (m, 1H), 7.60 (m, 1H), 8.25 (d, 2H), 8.90 (s, 1H), 8.94 (d, 2H); m/z (ESI) 446.2 [M+H]$^+$.

9-Methyl-N-(4-(piperazin-1-ylmethyl)phenyl)-8-(pyridin-4-yl)-9H-purin-2-amine

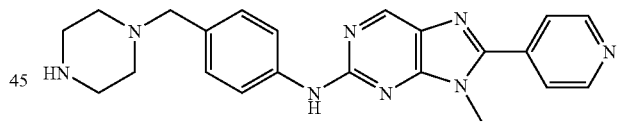

(δ$_H$, 300 MHz, CD$_3$OD) 3.61 (m, 8H), 4.12 (s, 3H), 4.44 (s, 2H), 7.51 (d, 2H), 8.03 (d, 2H), 8.43 (d, 2H), 8.95 (s, 1H), 9.00 (bs, 2H); m/z (ESI) 401.2 [M+H]$^+$.

N-(3-(2-(Cyclopentylamino)ethyl)phenyl)-9-ethyl-8-(pyridin-4-yl)-9H-purin-2-amine

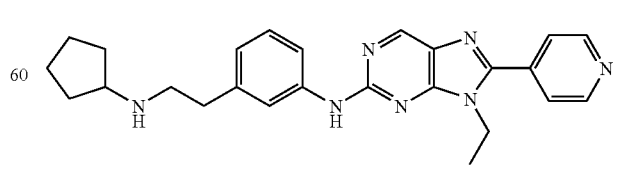

(δ$_H$, 300 MHz, CD$_3$OD) 1.52 (t, 3H), 1.66 (m, 4H), 1.81 (m, 2H), 2.17 (m, 2H), 3.05 (t, 2H), 3.26 (t, 2H), 3.59 (m, 1H), 4.51 (q, 2H), 7.01 (d, 1H), 7.35 (m, 1H), 7.68 (s, 1H), 7.79 (d, 1H), 8.24 (d, 2H), 8.86 (s, 1H), 8.92 (d, 2H); m/z (ESI) 428.3 [M+H]⁺.

N-(3-(Aminomethyl)phenyl)-9-cyclopropyl-8-(pyridin-4-yl)-9H-purin-2-amine

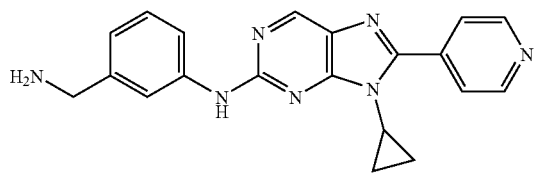

(δ_H, 300 MHz, CD₃OD) 1.06 (m, 2H), 1.32 (m, 2H), 3.78 (m, 1H), 4.15 (s, 2H), 7.14 (d, 1H), 7.45 (m, 1H), 7.95 (m, 1H), 8.01 (dd, 1H), 8.57 (d, 2H), 8.91 (s, 1H), 8.95 (d, 2H); m/z (ESI) 358.2 [M+H]⁺.

9-Isopropyl-N-(3-methoxyphenyl)-8-(2-(methylamino)pyrimidin-4-yl)-9H-purin-2-amine

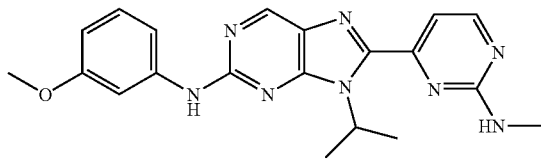

(δ_H, 300 MHz, CD₃OD) 1.97 (d, 6H), 3.20 (s, 3H), 3.99 (s, 3H), 6.20 (m, 1H), 6.78 (m, 1H), 7.38 (m, 2H), 7.62 (m, 1H), 7.72 (m, 1H), 8.55 (m, 1H), 8.99 (s, 1H); m/z (ESI) 391.2 [M+H]⁺.

N-(3-Chlorophenyl)-9-cyclopropyl-8-(2-(methylamino)pyrimidin-4-yl)-9H-purin-2-amine

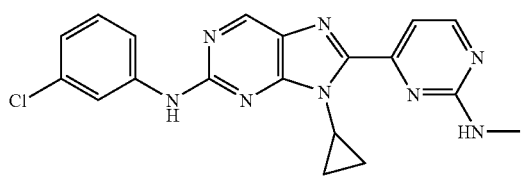

(δ_H, 300 MHz, CD₃OD) 1.33 (m, 2H), 1.47 (m, 2H), 3.26 (s, 3H), 3.99 (m, 1H), 7.15 (m, 1H), 7.44 (m, 1H), 7.69 (m, 2H), 8.52 (m, 2H), 9.02 (s, 1H); m/z (ESI) 393.2 [M+H]⁺.

9-Cyclopropyl-N-(4-((methylamino)methyl)phenyl)-8-(pyridin-4-yl)-9H-purin-2-amine

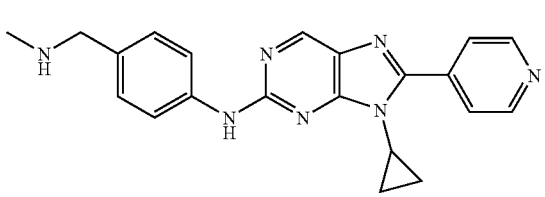

(δ_H, 300 MHz, CD₃OD) 1.05 (m, 2H), 1.32 (m, 2H), 2.73 (s, 3H), 3.77 (m, 1H), 4.17 (s, 2H), 7.46 (d, 2H), 8.02 (d, 2H), 8.54 (d, 2H), 8.90 (s, 1H), 8.93 (d, 2H); m/z (ESI) 372.2 [M+H]⁺.

8-(2-Aminopyrimidin-4-yl)-9-ethyl-N-(3-fluorophenyl)-9H-purin-2-amine

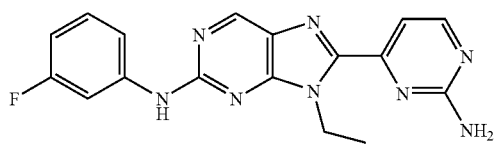

(δ_H, 300 MHz, CD₃OD) 1.42 (t, 3H), 4.84 (q, 2H), 6.62 (m, 1H), 7.12 (m, 1H), 7.37 (dd, 1H), 7.58 (d, 1H), 7.82 (m, 1H), 8.30 (d, 1H), 8.82 (s, 1H); m/z (ESI) 351.2 [M+H]⁺.

8-(2-Aminopyrimidin-4-yl)-9-isopropyl-N-(3-methoxyphenyl)-9H-purin-2-amine

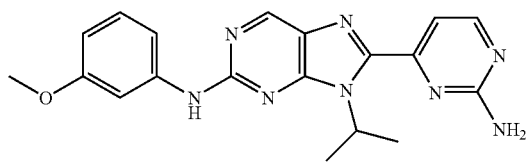

(δ_H, 300 MHz, CD₃OD) 1.96 (m, 6H), 3.99 (s, 3H), 6.25 (m, 1H), 6.78 (m, 1H), 7.38 (m, 2H), 7.72 (m, 1H), 7.76 (m, 1H), 8.52 (m, 1H), 9.01 (s, 1H) m/z (ESI) 377.1 [M+H]⁺.

9-Ethyl-N-(3-(2-methoxyethoxy)phenyl)-8-(pyridin-4-yl)-9H-purin-2-amine

(δ$_H$, 300 MHz, CD$_3$OD) 1.54 (t, 3H), 3.45 (s, 3H), 3.77 (t, 2H), 4.15 (t, 2H), 4.50 (q, 2H), 7.62 (m, 1H), 7.23 (m, 2H), 7.61 (m, 1H), 8.21 (d, 2H), 8.85 (s, 1H), 8.91 (d, 2H); m/z (ESI) 391.2 [M+H]$^+$.

N-(3,4-Difluorophenyl)-9-ethyl-8-(pyridin-4-yl)-9H-purin-2-amine

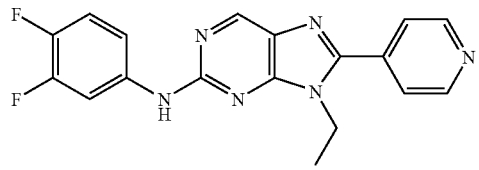

(δ$_H$, 300 MHz, CD$_3$OD) 1.56 (t, 3H), 4.51 (q, 2H), 7.20 (m, 1H), 7.42 (m, 1H), 8.02 (m, 1H), 8.29 (d, 2H), 8.85 (s, 1H), 8.94 (b, 2H); m/z (ESI) 353.2 [M+H]$^+$.

8-(2-Aminopyrimidin-4-yl)-N-(2,4-dimethylphenyl)-9-ethyl-9H-purin-2-amine

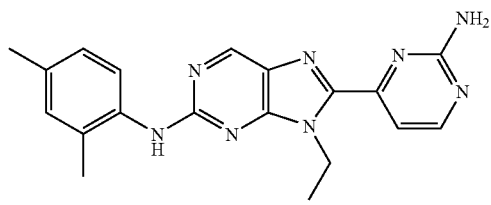

(δ$_H$, 400 MHz, d$_6$DMSO) 1.30 (t, 3H), 2.19 (s, 3H), 2.26 (s, 3H), 4.67 (q, 2H), 6.82 (s, 2H), 6.97 (d, 1H), 7.02 (s, 1H), 7.31 (d, 1H), 7.41 (d, 1H), 8.38 (d, 1H), 8.79 (s, 1H), 8.83 (s, 1H); m/z (ESI) 361.2 [M+H]$^+$.

9-Ethyl-N-(3-(2-(ethylamino)ethyl)phenyl)-8-(pyridin-4-yl)-9H-purin-2-amine

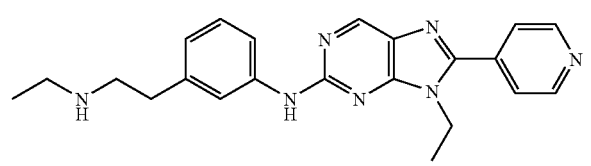

(δ$_H$, 300 MHz, CD$_3$OD) 1.29 (t, 3H), 1.53 (t, 3H), 3.04 (t, 2H), 3.07 (q, 2H), 3.26 (t, 2H), 4.48 (q, 2H), 6.98 (d, 1H), 7.34 (m, 1H), 7.66 (s, 1H), 7.77 (m, 1H), 8.23 (d, 2H), 8.87 (s, 1H), 8.92 (m, 2H); m/z (ESI) 388.3 [M+H]$^+$.

9-Methyl-N-(3-(morpholinomethyl)phenyl)-8-(pyridin-4-yl)-9H-purin-2-amine

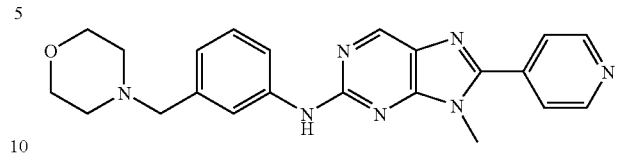

(δ$_H$, 300 MHz, CD$_3$OD) 3.30 (m, 2H), 3.43 (m, 2H), 3.78 (m, 2H), 4.05 (m, 2H), 4.06 (s, 3H), 4.39 (s, 2H), 7.19 (d, 1H), 7.47 (m, 1H), 7.93 (dd, 1H), 8.00 (m, 1H), 8.42 (d, 2H), 8.92 (s, 1H), 8.96 (bd, 2H); m/z (ESI) 402.1 [M+H]$^+$.

4-(9-Ethyl-2-(4-fluorophenoxy)-9H-purin-8-yl)pyrimidin-2-amine

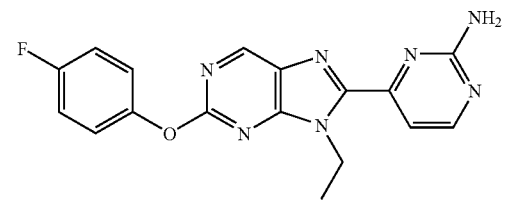

(δ$_H$, 300 MHz, CD$_3$OD) 1.42 (t, 3H), 4.80 (q, 2H), 7.23 (m, 4H), 7.79 (d, 1H), 8.43 (m, 1H), 9.02 (s, 1H); m/z (ESI) 352.2 [M+H]$^+$.

9-Methyl-N-(4-(2-(piperidin-1-yl)ethyl)phenyl)-8-(pyridin-4-yl)-9H-purin-2-amine

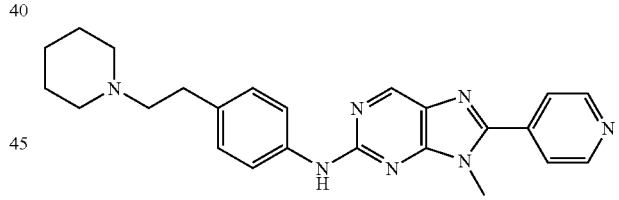

(δ$_H$, 300 MHz, CD$_3$OD) 1.55 (m, 2H), 1.80 (m, 2H), 1.96 (m, 2H), 3.02 (m, 4H), 3.35 (m, 2H), 3.62 (m, 2H), 4.02 (s, 3H), 7.28 (d, 2H), 7.81 (d, 2H), 8.25 (d, 2H), 8.86 (s, 1H), 8.88 (m, 2H); m/z (ESI) 414.2 [M+H]$^+$.

N-(4-(Aminomethyl)phenyl)-9-cyclopropyl-8-(pyridin-4-yl)-9H-purin-2-amine

(δ$_H$, 300 MHz, CD$_3$OD) 1.04 (m, 2H), 1.30 (m, 2H), 3.76 (m, 1H), 4.10 (s, 2H), 7.44 (d, 2H), 8.00 (d, 2H), 8.49 (d, 2H), 8.89 (s, 1H), 8.93 (d, 2H); m/z (ESI) 358.2 [M+H]$^+$.

8-(2-Aminopyrimidin-4-yl)-9-cyclopropyl-N-(4-fluorophenyl)-9H-purin-2-amine

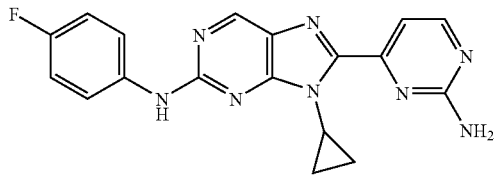

(δ$_H$, 300 MHz, CD$_3$OD) 1.30 (m, 2H), 1.43 (m, 2H), 3.94 (m, 1H), 7.23 (m, 2H), 7.74 (d, 1H), 7.97 (m, 2H), 8.53 (d, 1H), 8.99 (s, 1H); m/z (ESI) 363.3 [M+H]$^+$.

8-(2-Aminopyrimidin-4-yl)-9-ethyl-N-o-tolyl-9H-purin-2-amine

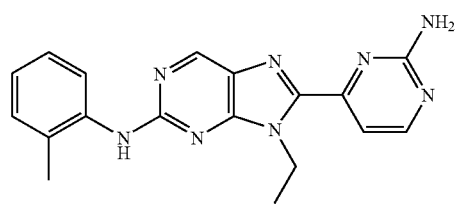

(δ$_H$, 300 MHz, d$_6$DMSO) 1.42 (t, 3H), 2.25 (s, 3H). 4.70 (q, 2H), 6.89 (bs, 2H), 7.05 (m, 1H), 7.20 (m, 2H), 7.32 (d, 1H), 7.59 (d, 1H), 8.39 (d, 1H), 8.82 (s, 1H), 8.90 (s, 1H); m/z (ESI) 347.1 [M+H]$^+$.

N-(4-(2-Aminoethyl)phenyl)-9-methyl-8-(pyridin-4-yl)-9H-purin-2-amine

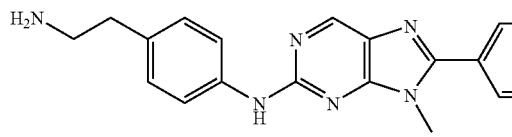

(δ$_H$, 300 MHz, CD$_3$OD) 2.97 (t, 2H), 3.19 (t, 2H), 4.03 (s, 3H), 7.28 (d, 2H), 7.82 (d, 2H), 8.31 (d, 2H), 8.87 (s, 1H), 8.92 (d, 2H); m/z (ESI) 346.2 [M+H]$^+$.

9-Isopropyl-N-(3-methoxyphenyl)-8-(pyrimidin-4-yl)-9H-purin-2-amine

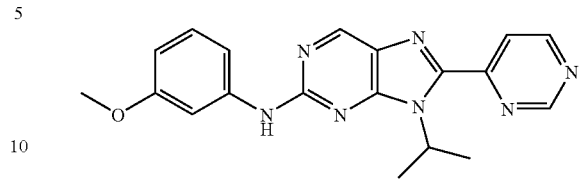

(δ$_H$, 300 MHz, CD$_3$OD) 1.74 (d, 6H), 3.76 (s, 3H), 5.95 (m, 1H), 6.53 (m, 1H), 7.14 (m, 2H), 7.50 (m, 1H), 8.16 (m, 1H), 8.76 (s, 1H), 8.88 (m, 1H), 9.23 (s, 1H); m/z (ESI) 362.1 [M+H]$^+$.

N-(4-(2-(Cyclopropylamino)ethyl)phenyl)-9-ethyl-8-(pyridin-4-yl)-9H-purin-2-amine

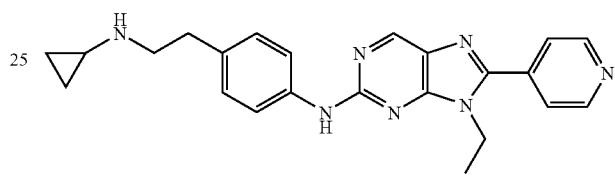

(δ$_H$, 300 MHz, CD$_3$OD) 0.93 (m, 4H), 1.53 (t, 3H), 2.80 (m, 1H), 3.00 (t, 2H), 3.39 (t, 2H), 4.51 (q, 2H), 7.30 (d, 2H), 7.82 (d, 2H), 8.21 (d, 2H), 8.88 (s, 1H), 8.93 (d, 2H); m/z (ESI) 400.2 [M+H]$^+$.

N-(3-(2-(Dimethylamino)ethyl)phenyl)-9-ethyl-8-(pyridin-4-yl)-9H-purin-2-amine

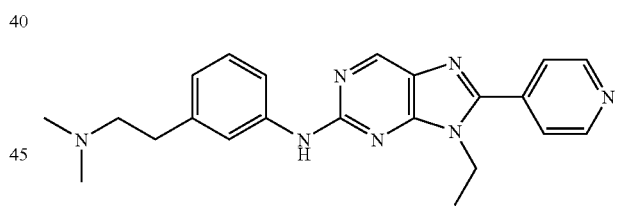

(δ$_H$, 300 MHz, CD$_3$OD) 1.52 (t, 3H), 2.41 (s, 6H), 2.72 (m, 2H), 2.85 (m, 2H), 4.48 (q, 2H), 6.90 (d, 1H), 7.26 (m, 1H), 7.66 (dd, 1H), 7.74 (m, 1H), 7.87 (d, 2H), 8.80 (m, 3H); m/z (ESI) 388.3 [M+H]$^+$.

9-Ethyl-N-(3-(2-(piperidin-1-yl)ethoxy)phenyl)-8-(pyridin-4-yl)-9H-purin-2-amine

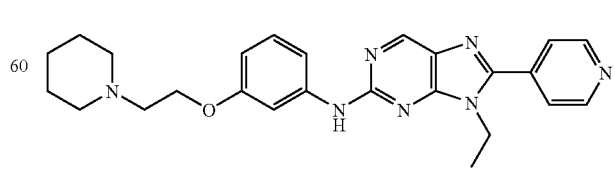

(δ$_H$, 300 MHz, CD$_3$OD) 1.55 (t, 3H), 1.90 (m, 6H), 3.10 (m, 2H), 3.62 (m, 4H), 4.42 (t, 2H), 4.50 (q, 2H), 7.70 (dd,

1H), 7.31 (m, 1H), 7.46 (m, 1H), 7.63 (m, 1H), 8.07 (d, 2H), 8.88 (m, 3H); m/z (ESI) 444.2 [M+H]⁺.

9-Methyl-N-(4-((methylamino)methyl)phenyl)-8-(pyridin-4-yl)-9H-purin-2-amine

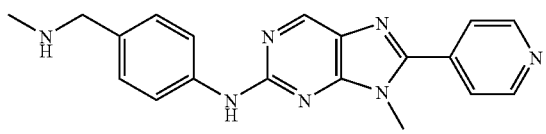

($\delta_H$, 300 MHz, CD$_3$OD) 2.73 (s, 3H), 4.08 (s, 3H), 4.17 (s, 2H), 7.46 (d, 2H), 7.96 (d, 2H), 8.49 (d, 2H), 8.94 (s, 1H), 8.96 (d, 2H); m/z (ESI) 346.2 [M+H]⁺.

8-(2-Aminopyridin-4-yl)-9-ethyl-N-(3-ethylphenyl)-9H-purin-2-amine

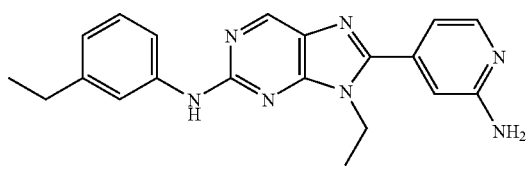

($\delta_H$, 300 MHz, CD$_3$OD) 1.20 (t, 3H), 1.49 (t, 3H), 2.58 (q, 2H), 4.37 (q, 2H), 6.81 (d, 1H), 7.17 (m, 1H), 7.23 (dd, 1H), 7.34 (s, 1H), 7.51 (m, 1H), 7.62 (s, 1H), 7.92 (d, 1H), 8.76 (s, 1H); m/z (ESI) 360.3 [M+H]⁺.

8-(2-Aminopyrimidin-4-yl)-9-ethyl-N-p-tolyl-9H-purin-2-amine

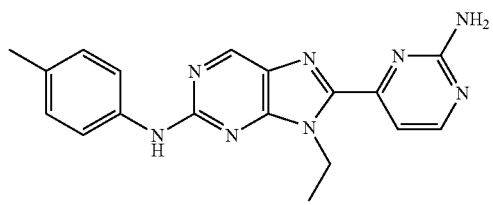

($\delta_H$, 400 MHz, d$_6$DMSO) 1.38 (t, 3H), 2.25 (s, 3H). 4.79 (q, 2H), 6.91 (bs, 2H), 7.10 (d, 2H), 7.33 (d, 1H), 7.73 (d, 2H), 8.39 (d, 1H), 8.97 (s, 1H), 9.70 (s, 1H); m/z (ESI) 347.1 [M+H]⁺.

9-Methyl-8-(pyridin-4-yl)-N-(4-(2-(pyrrolidin-1-yl)ethyl)phenyl)-9H-purin-2-amine

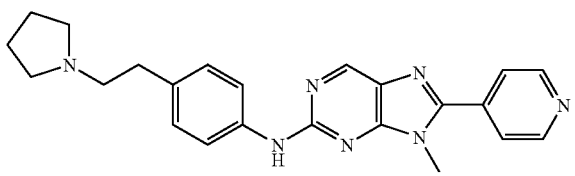

($\delta_H$, 300 MHz, CD$_3$OD) 2.01 (m, 2H), 2.18 (m, 2H), 3.05 (t, 2H), 3.16 (m, 2H), 3.48 (t, 2H), 3.69 (m, 2H), 4.00 (s, 3H), 7.29 (d, 2H), 7.84 (d, 2H), 8.11 (d, 2H), 8.84 (m, 3H); m/z (ESI) 400.2 [M+H]⁺.

9-Methyl-8-(pyridin-4-yl)-N-(3-(2-(pyrrolidin-1-yl)ethyl)phenyl)-9H-purin-2-amine

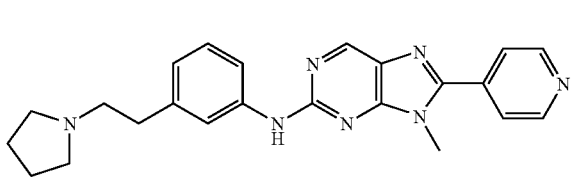

($\delta_H$, 300 MHz, CD$_3$OD) 2.03 (m, 2H), 2.19 (m, 2H), 3.08 (t, 2H), 3.14 (m, 2H), 3.52 (t, 2H), 4.02 (s, 3H), 4.41 (s, 2H), 7.00 (d, 1H), 7.36 (m, 1H), 7.71 (m, 1H), 7.84 (dd, 1H), 8.18 (d, 2H), 8.87 (s, 1H), 8.89 (m, 2H); m/z (ESI) 400.2 [M+H]⁺.

N-(3-(Aminomethyl)phenyl)-9-methyl-8-(pyridin-4-yl)-9H-purin-2-amine

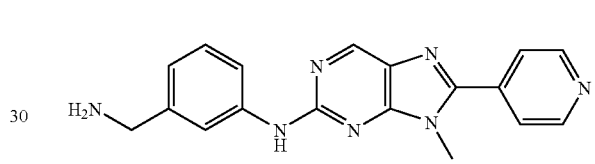

($\delta_H$, 300 MHz, CD$_3$OD) 4.08 (s, 3H), 4.15 (s, 2H), 7.15 (d, 1H), 7.44 (m, 1H), 7.91 (m, 2H), 8.46 (d, 2H), 8.94 (s, 1H), 8.98 (d, 2H); m/z (ESI) 332.1 [M+H]⁺.

N-(4-(9-Ethyl-8-(pyridin-4-yl)-9H-purin-2-ylamino)benzyl)acetamide

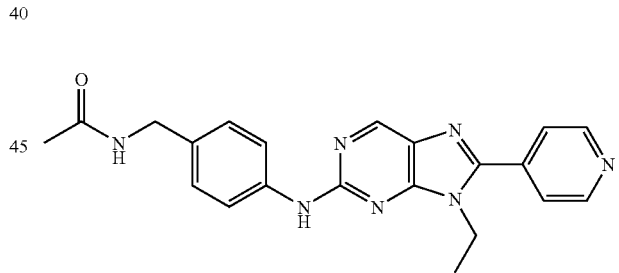

($\delta_H$, 300 MHz, CD$_3$OD) 1.53 (t, 3H), 2.00 (s, 3H), 4.34 (s, 2H), 4.50 (q, 2H), 7.29 (d, 2H), 7.76 (d, 2H), 8.25 (d, 2H), 8.87 (s, 1H), 8.92 (d, 2H); m/z (ESI) 388.2 [M+H]⁺.

N-(3-(9-Methyl-8-(pyridin-4-yl)-9H-purin-2-ylamino)benzyl)acetamide

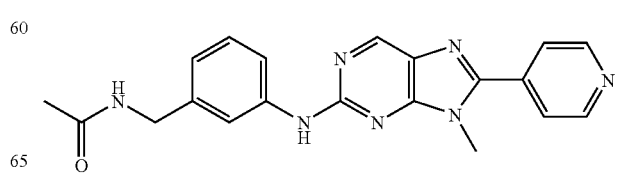

($δ_H$, 300 MHz, CD$_3$OD) 2.02 (s, 3H), 4.06 (s, 3H), 4.40 (s, 2H), 6.99 (d, 1H), 7.31 (m, 1H), 7.66 (m, 1H), 7.84 (s, 1H), 8.39 (d, 2H), 8.88 (s, 1H), 8.93 (d, 2H); m/z (ESI) 374.2 [M+H]$^+$.

N-(4-(Aminomethyl)phenyl)-9-methyl-8-(pyridin-4-yl)-9H-purin-2-amine

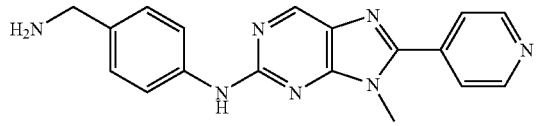

($δ_H$, 300 MHz, CD$_3$OD) 4.05 (s, 3H), 4.10 (s, 2H), 7.44 (d, 2H), 7.94 (d, 2H), 8.35 (d, 2H), 8.91 (m, 3H); m/z (ESI) 332.3 [M+H]$^+$.

8-(2-Aminopyridin-4-yl)-9-ethyl-N-(4-fluorophenyl)-9H-purin-2-amine

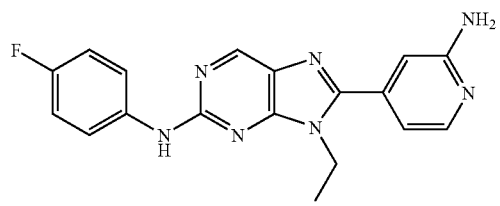

($δ_H$, 300 MHz, CD$_3$OD) 1.68 (t, 3H), 4.59 (q, 2H), 7.22 (m, 2H), 7.49 (m, 1H), 7.57 (m, 1H), 7.91 (m, 2H), 8.14 (d, 1H), 8.99 (s, 1H); m/z (ESI) 350.2 [M+H]$^+$.

N-(3-(2-(Dimethylamino)ethoxy)phenyl)-9-ethyl-8-(pyridin-4-yl)-9H-purin-2-amine

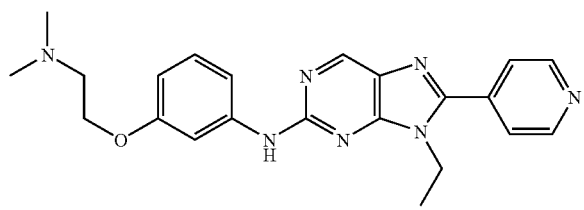

($δ_H$, 300 MHz, CD$_3$OD) 1.45 (t, 3H), 3.02 (s, 6H), 3.63 (t, 2H), 4.40 (t, 2H), 4.53 (q, 2H), 7.73 (dd, 1H), 7.32 (m, 1H), 7.47 (m, 1H), 7.59 (m, 1H), 8.27 (d, 2H), 8.89 (s, 1H), 8.93 (d, 2H); m/z (ESI) 404.1 [M+H]$^+$.

9-Methyl-N-(4-(piperidin-1-ylmethyl)phenyl)-8-(pyridin-4-yl)-9H-purin-2-amine

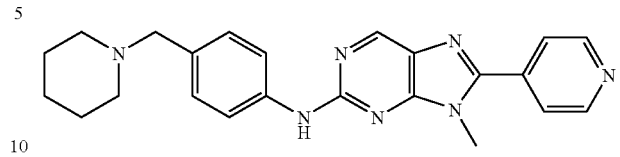

($δ_H$, 300 MHz, CD$_3$OD) 1.51 (m, 2H), 1.64 (m, 4H), 2.59 (m, 4H), 3.62 (m, 2H), 3.96 (s, 3H), 7.30 (d, 2H), 7.84 (d, 2H), 7.94 (d, 2H), 8.78 (d, 2H), 8.82 (s, 1H); m/z (ESI) 400.1 [M+H]$^+$.

8-(2-Aminopyrimidin-4-yl)-N-(3,5-difluorophenyl)-9-ethyl-9H-purin-2-amine

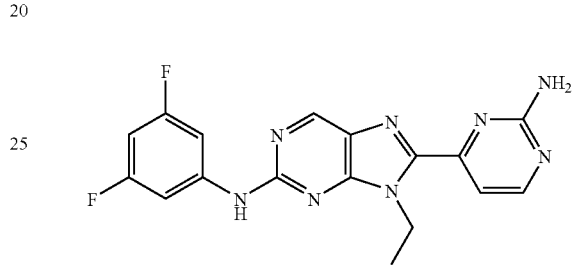

($δ_H$, 400 MHz, d$_6$DMSO) 1.42 (t, 3H), 4.83 (q, 2H), 6.75 (m, 1H), 6.98 (bs, 2H), 7.35 (d, 1H), 7.66 (m, 2H), 8.42 (d, 1H), 9.02 (s, 1H), 10.29 (s, 1H); m/z (ESI) 369.2 [M+H]$^+$.

N-(4-(2-(Dimethylamino)ethyl)phenyl)-9-ethyl-8-(pyridin-4-yl)-9H-purin-2-amine

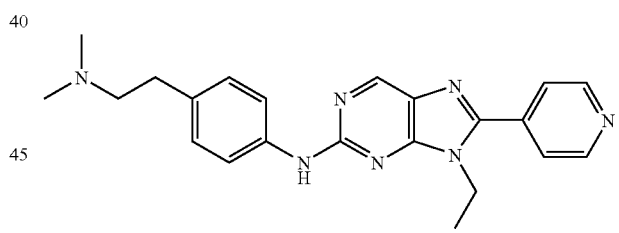

($δ_H$, 300 MHz, CD$_3$OD) 1.53 (t, 3H), 2.90 (s, 6H), 3.05 (m, 2H), 3.40 (m, 2H), 4.51 (q, 2H), 7.32 (d, 2H), 7.82 (d, 2H), 8.19 (d, 2H), 8.79 (s, 1H), 8.91 (s, 2H); m/z (ESI) 388.2 [M+H]$^+$.

9-Cyclopropyl-8-(2-(methylamino)pyrimidin-4-yl)-N-phenyl-9H-purin-2-amine

(δ$_H$, 300 MHz, CD$_3$OD) 1.10 (m, 2H), 1.18 (m, 2H), 3.01 (s, 3H), 3.79 (m, 1H), 6.97 (m, 1H), 7.27 (m, 2H), 7.44 (m, 1H), 7.74 (m, 2H), 8.31 (m, 1H), 8.76 (s, 1H); m/z (ESI) 359.2 [M+H]$^+$.

8-(2-Aminopyrimidin-4-yl)-N-(2,5-difluorophenyl)-9-ethyl-9H-purin-2-amine

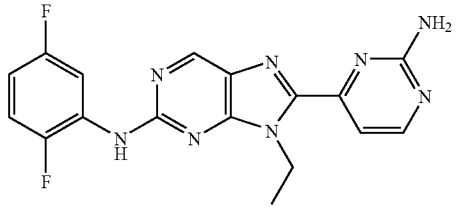

(δ$_H$, 300 MHz, CD$_3$OD) 1.50 (t, 3H), 4.94 (q, 2H), 6.78 (m, 1H), 7.19 (m, 1H), 7.72 (d, 1H), 8.37 (m, 2H), 8.97 (s, 1H); m/z (ESI) 369.2 [M+H]$^+$.

9-Cyclopropyl-N-(3-(2-morpholinoethoxy)phenyl)-8-(pyridin-4-yl)-9H-purin-2-amine

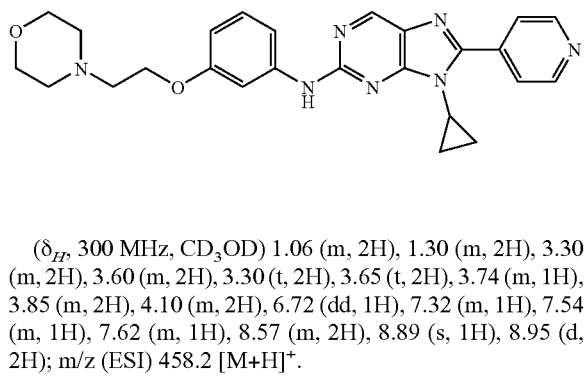

(δ$_H$, 300 MHz, CD$_3$OD) 1.06 (m, 2H), 1.30 (m, 2H), 3.30 (m, 2H), 3.60 (m, 2H), 3.30 (t, 2H), 3.65 (t, 2H), 3.74 (m, 1H), 3.85 (m, 2H), 4.10 (m, 2H), 6.72 (dd, 1H), 7.32 (m, 1H), 7.54 (m, 1H), 7.62 (m, 1H), 8.57 (m, 2H), 8.89 (s, 1H), 8.95 (d, 2H); m/z (ESI) 458.2 [M+H]$^+$.

8-(2-Aminopyrimidin-4-yl)-N-(3,4-difluorophenyl)-9-ethyl-9H-purin-2-amine

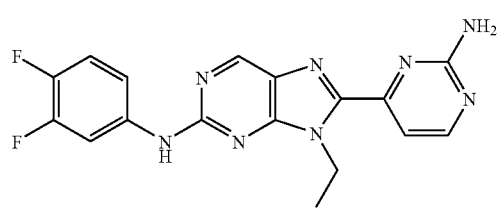

(δ$_H$, 400 MHz, d$_6$DMSO) 1.42 (t, 3H), 4.81 (q, 2H), 6.93 (bs, 2H), 7.33 (m, 2H), 7.45 (m, 1H), 8.07 (m, 1H), 8.41 (d, 1H), 8.95 (s, 1H), 10.04 (s, 1H); m/z (ESI) 369.2 [M+H]$^+$.

8-(2-Aminopyrimidin-4-yl)-N-(2,3-difluorophenyl)-9-ethyl-9H-purin-2-amine

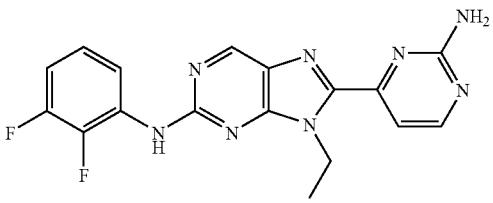

(δ$_H$, 300 MHz, CD$_3$OD) 1.51 (t, 3H), 4.89 (q, 2H), 6.97 (m, 1H), 7.15 (m, 1H), 7.44 (d, 1H), 8.14 (m, 1H), 8.41 (d, 1H), 8.84 (s, 1H); m/z (ESI) 369.2 [M+H]$^+$.

8-(2-Aminopyrimidin-4-yl)-N-(4-fluorophenyl)-9-methyl-9H-purin-2-amine

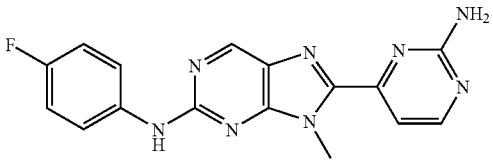

(δ$_H$, 300 MHz, CD$_3$OD) 4.24 (s, 3H), 7.08 (m, 2H), 7.65 (d, 1H), 7.79 (m, 2H), 8.37 (d, 1H), 8.87 (s, 1H); m/z (ESI) 337.3 [M+H]$^+$.

tert-Butyl 4-(9-cyclopropyl-8-(pyridin-4-yl)-9H-purin-2-ylamino)benzylcarbamate

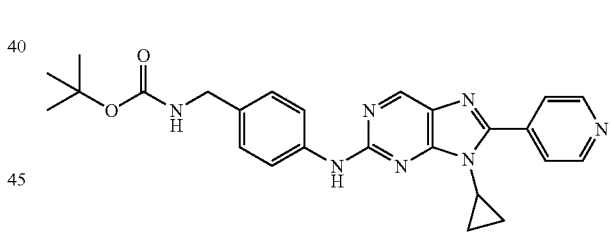

(δ$_H$, 300 MHz, CD$_3$OD) 1.02 (m, 2H), 1.31 (m, 2H), 1.46 (s, 9H), 3.73 (m, 1H), 4.22 (s, 2H), 7.28 (d, 2H), 7.82 (d, 2H), 7.48 (d, 2H), 8.84 (s, 1H), 8.90 (d, 2H); m/z (ESI) 458.2 [M+H]$^+$.

9-Methyl-N-(3-(2-(piperidin-1-yl)ethyl)phenyl)-8-(pyridin-4-yl)-9H-purin-2-amine

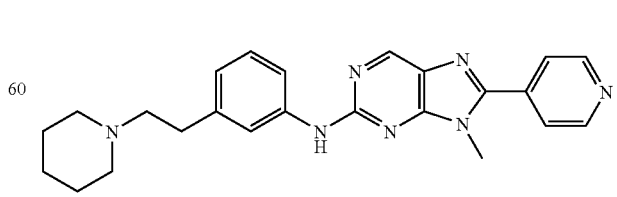

(δ$_H$, 300 MHz, CD$_3$OD) 1.52 (m, 2H), 1.82 (m, 2H), 1.96 (m, 2H), 3.05 (m, 4H), 3.37 (m, 2H), 3.65 (m, 2H), 4.01 (s,

3H), 6.98 (d, 1H), 7.34 (m, 1H), 7.70 (m, 1H), 7.80 (dd, 1H), 8.17 (d, 2H), 8.86 (s, 1H), 8.87 (d, 2H); m/z (ESI) 414.2 [M+H]⁺.

N-(4-(2-Aminoethyl)phenyl)-9-ethyl-8-(pyridin-4-yl)-9H-purin-2-amine

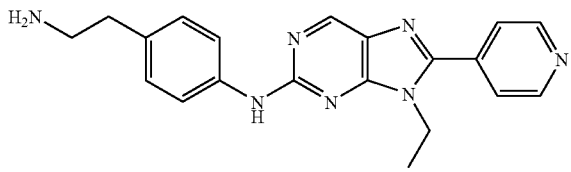

($\delta_H$, 300 MHz, CD$_3$OD) 1.42 (t, 3H), 2.87 (t, 2H), 3.10 (t, 2H), 4.37 (q, 2H), 7.18 (d, 2H), 7.73 (d, 2H), 8.92 (d, 2H), 8.74 (m, 3H); m/z (ESI) 360.1 [M+H]⁺.

9-Ethyl-N-(3-((ethylamino)methyl)phenyl)-8-(pyridin-4-yl)-9H-purin-2-amine

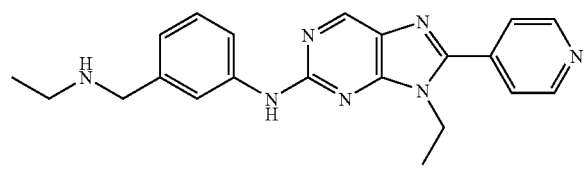

($\delta_H$, 300 MHz, CD$_3$OD) 1.28 (t, 3H), 1.49 (t, 3H), 2.95 (q, 2H), 4.02 (s, 2H), 4.44 (q, 2H), 7.08 (d, 1H), 7.37 (m, 1H), 7.85 (m, 4H), 8.80 (m, 3H); m/z (ESI) 374.2 [M+H]⁺.

8-(2-Aminopyrimidin-4-yl)-9-cyclopropyl-N-m-tolyl-9H-purin-2-amine

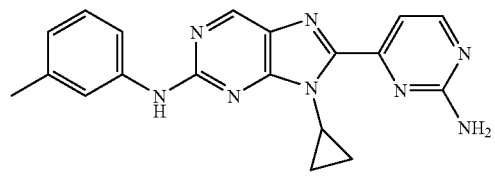

($\delta_H$, 300 MHz, CD$_3$OD) 1.34 (m, 2H), 1.44 (m, 2H), 2.53 (s, 3H), 3.94 (m, 1H), 7.01 (m, 1H), 7.35 (m, 1H), 7.71 (m, 2H), 7.89 (s, 1H), 8.50 (m, 1H), 8.96 (m, 1H); m/z (ESI) 359.3 [M+H]⁺.

N-(4-(9-Methyl-8-(pyridin-4-yl)-9H-purin-2-ylamino)phenethyl)acetamide

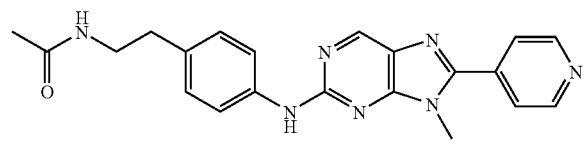

($\delta_H$, 300 MHz, CD$_3$OD) 1.93 (s, 3H), 2.81 (t, 2H), 3.38 (t, 2H), 4.02 (s, 3H), 7.22 (d, 2H), 7.73 (d, 2H), 8.27 (d, 2H), 8.85 (s, 1H), 8.9 (d, 2H); m/z (ESI) 388.3 [M+H]⁺.

8-(2-Aminopyrimidin-4-yl)-N-(3,4-dimethylphenyl)-9-ethyl-9H-purin-2-amine

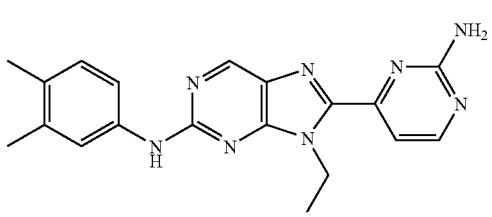

($\delta_H$, 300 MHz, d$_6$DMSO) 1.42 (t, 3H), 2.15 (s, 3H), 2.18 (s, 3H), 4.69 (q, 2H), 7.06 (d, 1H), 7.10 (bs, 2H), 7.37 (d, 1H), 7.59 (m 1H), 7.62 (s, 1H), 8.40 (d, 1H), 8.92 (s, 1H), 9.69 (s, 1H); m/z (ESI) 361.3 [M+H]⁺.

N-(3-(9-Cyclopropyl-8-(pyridin-4-yl)-9H-purin-2-ylamino)benzyl)acetamide

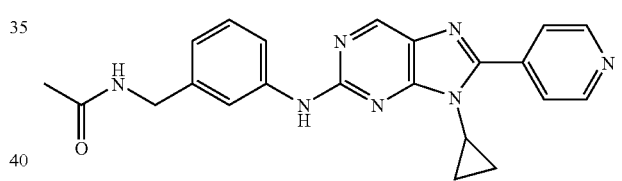

($\delta_H$, 300 MHz, CD$_3$OD) 1.06 (m, 2H), 1.34 (m, 2H), 2.01 (s, 3H), 3.76 (m, 1H), 4.41 (s, 2H), 7.00 (d, 1H), 7.32 (m, 1H), 7.71 (m, 1H), 7.89 (s, 1H), 8.60 (d, 2H), 8.87 (s, 1H), 8.94 (d, 2H); m/z (ESI) 400.2 [M+H]⁺.

N-(4-((Cyclopentylamino)methyl)phenyl)-9-ethyl-8-(pyridin-4-yl)-9H-purin-2-amine

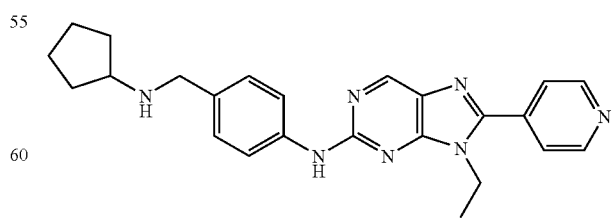

($\delta_H$, 300 MHz, CD$_3$OD) 1.51 (t, 3H), 1.75 (m, 6H), 2.20 (m, 2H), 3.61 (m, 1H), 4.18 (s, 2H), 4.46 (q, 2H), 7.46 (d, 2H), 7.96 (m, 4H), 8.84 (m, 3H); m/z (ESI) 414.2 [M+H]⁺.

111

8-(2-Aminopyrimidin-4-yl)-N-(2-chloro-5-fluorophenyl)-9-cyclopropyl-9H-purin-2-amine

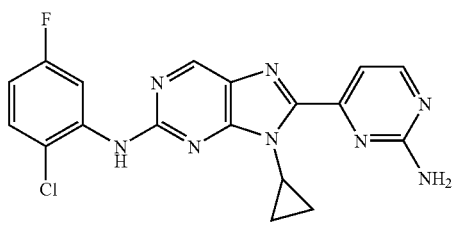

(δ_H, 300 MHz, d_6DMSO) 1.08 (m, 4H), 3.77 (m, 1H), 6.94 (m, 2H), 7.24 (d, 1H), 7.54 (dd, 1H), 8.26 (m, 1H), 8.42 (d, 1H), 8.75 (s, 1H), 8.94 (s, 1H); m/z (ESI) 397.2 [M+H]$^+$.

9-Cyclopropyl-N-(3-methoxyphenyl)-8-(pyrimidin-4-yl)-9H-purin-2-amine

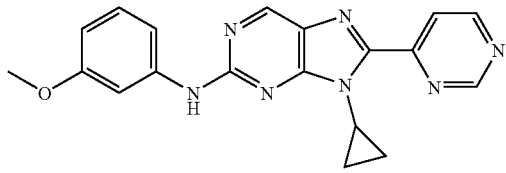

(δ_H, 300 MHz, CDCl_3) 1.11 (m, 2H), 1.32 (m, 2H), 3.92 (m, 4H), 6.78 (m, 1H), 7.33 (m, 2H), 7.50 (s, 1H), 8.28 (m, 1H), 8.76 (s, 1H), 9.06 (m, 1H), 9.46 (m, 1H), 10.97 (s, 1H); m/z (ESI) 360.2 [M+H]$^+$.

8-(2-Aminopyrimidin-4-yl)-N-(2,3-dimethylphenyl)-9-ethyl-9H-purin-2-amine

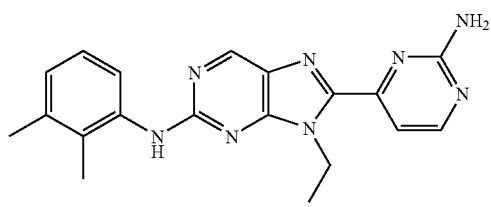

(δ_H, 400 MHz, d_6DMSO) 1.32 (t, 3H), 2.10 (s, 3H), 2.26 (s, 3H), 4.69 (q, 2H), 6.82 (s, 2H), 6.88 (d, 1H), 7.03 (m, 1H), 7.31 (m, 2H), 8.36 (d, 1H), 8.78 (s, 1H), 8.97 (s, 1H); m/z (ESI) 361.1 [M+H]$^+$.

112

N-(2,3-Dihydrobenzo[b][1,4]dioxin-6-yl)-9-ethyl-8-(pyridin-4-yl)-9H-purin-2-amine

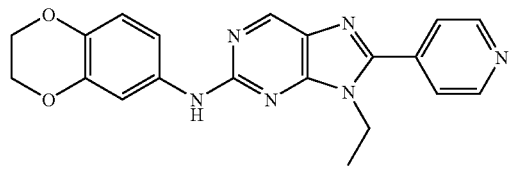

(δ_H, 300 MHz, CD_3OD) 1.51 (t, 3H), 4.25 (m, 4H), 4.45 (q, 2H), 6.81 (d, 1H), 7.08 (dd, 1H), 7.44 (d, 1H), 8.12 (d, 2H), 8.80 (s, 1H), 8.88 (d, 2H); m/z (ESI) 375.3 [M+H]$^+$.

3-(2-(3-Methoxyphenylamino)-8-(pyrimidin-4-yl)-9H-purin-9-yl)propanenitrile

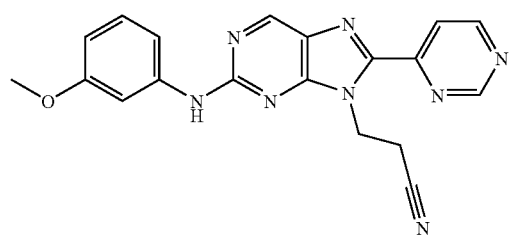

(δ_H, 300 MHz, CDCl_3) 3.17 (m, 2H), 3.86 (s, 3H), 5.15 (m, 2H), 6.98 (m, 1H), 7.22 (m, 2H), 8.38 (m, 2H), 8.74 (s, 1H), 9.00 (m, 2H), 9.38 (m, 1H); m/z (ESI) 373.2 [M+H]$^+$.

9-Ethyl-N-(3-ethylphenyl)-8-(2-(methylamino)pyrimidin-4-yl)-9H-purin-2-amine

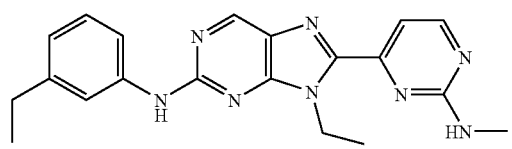

(δ_H, 300 MHz, CDCl_3) 1.23 (t, 3H), 1.58 (t, 3H), 2.65 (q, 2H), 3.08 (s, 3H), 4.88 (q, 2H), 7.00 (d, 1H), 7.30 (m, 1H), 7.58 (d, 1H), 7.60 (s, 1H), 7.76 (m, 1H), 8.20 (m, 1H), 8.80 (s, 1H). 9.25 (bs, 1H), 9.90 (bs, 1H); m/z (ESI) 375.3 [M+H]$^+$

9-Ethyl-N-(4-((ethylamino)methyl)phenyl)-8-(pyridin-4-yl)-9H-purin-2-amine

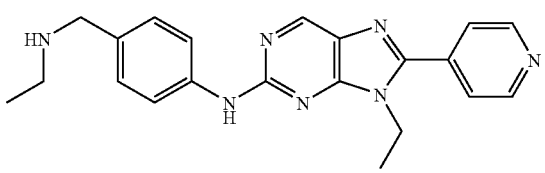

(δ$_H$, 300 MHz, CD$_3$OD) 1.30 (t, 3H), 1.55 (t, 3H), 3.15 (q, 2H), 4.17 (s, 2H), 4.52 (q, 2H), 7.45 (d, 2H), 7.35 (d, 1H), 7.96 (d, 2H), 8.18 (d, 2H), 8.90 (m, 3H); m/z (ESI) 374.2 [M+H]$^+$.

9-Methyl-N-(4-(2-morpholinoethyl)phenyl)-8-(pyridin-4-yl)-9H-purin-2-amine

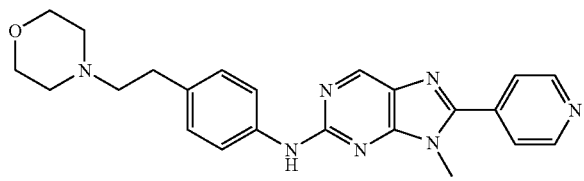

(δ$_H$, 300 MHz, CD$_3$OD) 3.06 (m, 2H), 3.25 (m, 2H), 3.41 (m, 2H), 3.56 (m, 2H), 3.81 (m, 2H), 4.01 (s, 3H), 4.92 (m, 2H), 7.28 (d, 2H), 7.79 (d, 2H), 8.34 (d, 2H), 8.85 (s, 1H), 8.90 (d, 2H); m/z (ESI) 416.2 [M+H]$^+$.

8-(2-Chloropyridin-4-yl)-9-cyclopropyl-N-phenyl-9H-purin-2-amine

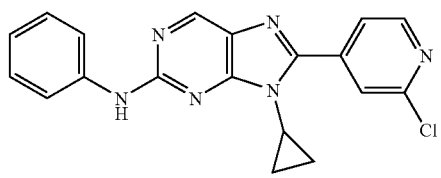

(δ$_H$, 300 MHz, CDCl$_3$) 1.01 (m, 2H), 1.32 (m, 2H), 3.51 (m, 1H), 7.17 (m, 2H), 7.40 (m, 2H), 7.84 (m, 3H), 7.97 (s, 1H), 8.64 (s, 1H), 11.4 (s, 1H); m/z (ESI) 363.2 [M+H]$^+$.

8-(2-Aminopyrimidin-4-yl)-9-ethyl-N-(3-fluoro-4-methylphenyl)-9H-purin-2-amine

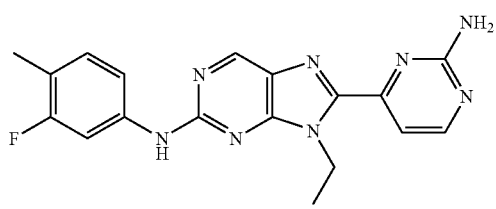

(δ$_H$, 400 MHz, d$_6$DMSO) 1.40 (t, 3H), 2.16 (s, 3H). 4.80 (q, 2H), 6.96 (bs, 2H), 7.17 (m, 1H), 7.35 (d, 1H), 7.47 (dd, 1H), 7.83 (d, 1H), 8.40 (d, 1H), 8.95 (s, 1H), 9.94 (s, 1H); m/z (ESI) 365.3 [M+H]$^+$.

9-Methyl-N-(4-((4-methylpiperazin-1-yl)methyl)phenyl)-8-(pyridin-4-yl)-9H-purin-2-amine

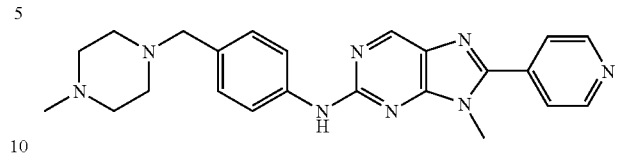

(δ$_H$, 300 MHz, CD$_3$OD) 2.56 (s, 3H), 2.71 (m, 4H), 2.88 (m, 4H), 3.63 (m, 2H), 3.95 (s, 3H), 7.31 (d, 2H), 7.81 (d, 2H), 7.93 (d, 2H), 8.77 (d, 2H), 8.79 (s, 1H); m/z (ESI) 415.2 [M+H]$^+$.

8-(2-Aminopyrimidin-4-yl)-N-(3,5-dimethylphenyl)-9-ethyl-9H-purin-2-amine

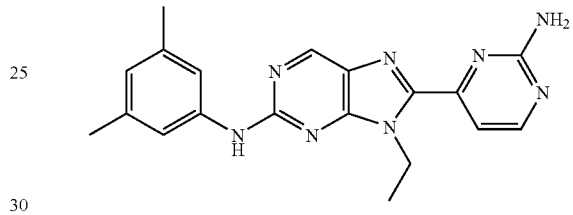

(δ$_H$, 400 MHz, d$_6$DMSO) 1.42 (t, 3H), 2.30 (s, 6H). 4.79 (q, 2H), 6.60 (s, 1H), 7.03 (bs, 2H), 7.35 (d, 1H), 7.50 (s, 2H), 8.40 (d, 1H), 8.92 (s, 1H), 9.68 (s, 1H); m/z (ESI) 361.3 [M+H]$^+$.

9-Methyl-N-(4-(morpholinomethyl)phenyl)-8-(pyridin-4-yl)-9H-purin-2-amine

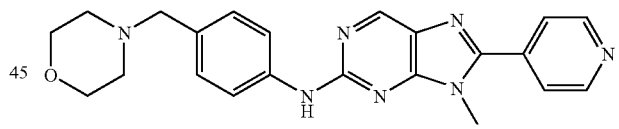

(δ$_H$, 300 MHz, CD$_3$OD) 3.20 (m, 2H), 3.39 (m, 2H), 3.72 (m, 2H), 4.04 (s, 3H), 4.08 (m, 2H), 4.34 (s, 2H), 7.49 (d, 2H), 8.00 (d, 2H), 8.24 (d, 2H), 8.88 (d, 2H), 8.90 (s, 1H); m/z (ESI) 402.3 [M+H]$^+$.

N-(3-((Dimethylamino)methyl)phenyl)-9-ethyl-8-(pyridin-4-yl)-9H-purin-2-amine

(δ$_H$, 300 MHz, CD$_3$OD) 1.53 (t, 3H), 2.92 (s, 6H), 4.38 (s, 2H), 4.53 (q, 2H), 7.16 (d, 1H), 7.49 (m, 1H), 7.95 (m, 2H), 8.18 (d, 2H), 8.91 (m, 3H); m/z (ESI) 374.2 [M+H]$^+$.

8-(2-Aminopyridin-4-yl)-9-ethyl-N-(4-fluoro-3-methoxyphenyl)-9H-purin-2-amine

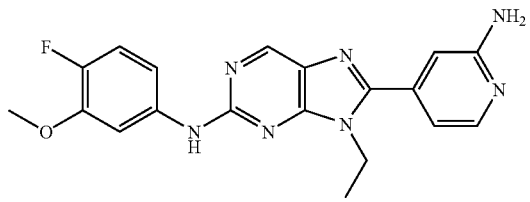

(δ$_H$, 300 MHz, CD$_3$OD) 1.56 (t, 3H), 3.93 (s, 3H), 4.44 (q, 2H), 7.03 (m, 1H), 7.20 (m, 1H), 7.33 (dd, 1H), 7.42 (s, 1H), 7.80 (dd, 1H), 8.01 (d, 1H), 8.85 (s, 1H); m/z (ESI) 380.2 [M+H]$^+$.

8-(2-Aminopyrimidin-4-yl)-N-(3-chlorophenyl)-9-ethyl-9H-purin-2-amine

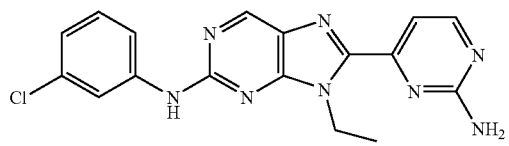

(δ$_H$, 300 MHz, CD$_3$OD) 1.46 (t, 3H), 4.84 (q, 2H), 6.92 (m, 1H), 7.22 (t, 1H), 7.54 (m, 1H), 7.60 (d, 1H), 8.06 (m, 1H), 8.29 (d, 1H), 8.84 (s, 1H); m/z (ESI) 367.2 [M+H]$^+$.

N-(4-(9-Methyl-8-(pyridin-4-yl)-9H-purin-2-ylamino)phenethyl)-N-methylacetamide

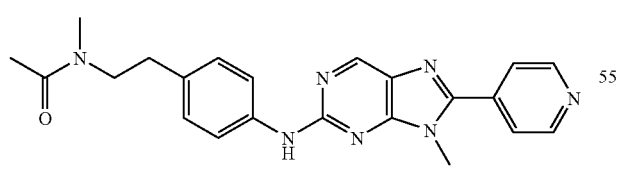

(δ$_H$, 300 MHz, CD$_3$OD, Rotational Isomers) [1.79 (s) & 2.07 (s), 3H, rotational isomers], 2.85 (m, 2H), [2.95 (s) & 3.00 (s), 3H, rotational isomers], 3.62 (m, 2H), 4.04 (s, 3H), 7.22 (m, 2H), 7.75 (m, 2H), 8.36 (m, 2H), [8.87 (s) & 8.88 (s), 1H, rotational isomers], 8.93 (d, 2H); m/z (ESI) 402.3 [M+H]$^+$.

8-(2-Aminopyrimidin-4-yl)-N-(4-chloro-2-fluorophenyl)-9-cyclopropyl-9H-purin-2-amine

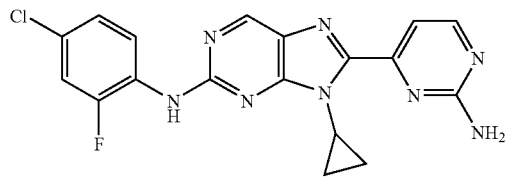

(δ$_H$, 400 MHz, d$_6$DMSO) 1.07 (m, 4H), 3.74 (m, 1H), 7.00 (bs, 2H), 7.24 (d, 1H), 7.27 (d, 1H), 7.47 (dd, 1H), 7.96 (m, 1H), 8.41 (d, 1H), 9.39 (s, 1H); m/z (ESI) 397.2 [M+H]$^+$.

9-Cyclopropyl-N-(4-(2-(methylamino)ethyl)phenyl)-8-(pyridin-4-yl)-9H-purin-2-amine

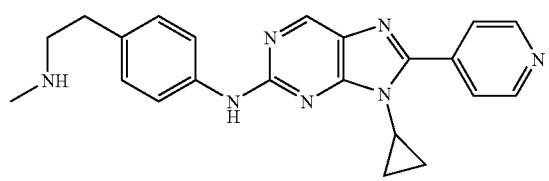

(δ$_H$, 300 MHz, CD$_3$OD) 1.05 (m, 2H), 1.32 (m, 2H), 2.74 (s, 3H), 3.00 (t, 2H), 3.30 (t, 2H), 3.76 (m, 1H), 7.30 (m, 2H), 7.86 (m, 2H), 8.66 (m, 2H), 8.90 (s, 1H), 8.98 (d, 2H); m/z (ESI) 486.2 [M+H]$^+$.

9-Cyclopropyl-N-(2-fluorophenyl)-8-(pyridin-4-yl)-9H-purin-2-amine

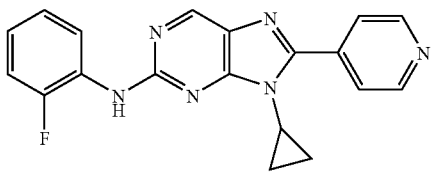

(δ$_H$, 300 MHz, CD$_3$OD) 1.01 (m, 2H), 1.26 (m, 2H), 3.78 (m, 1H), 7.15 (m, 1H), 7.19 (m, 2H), 8.40 (d, 2H), 8.43 (m, 1H), 8.60 (m, 3H); m/z (ESI) 347.2 [M+H]$^+$.

9-Ethyl-N-(4-(2-(ethylamino)ethyl)phenyl)-8-(pyridin-4-yl)-9H-purin-2-amine

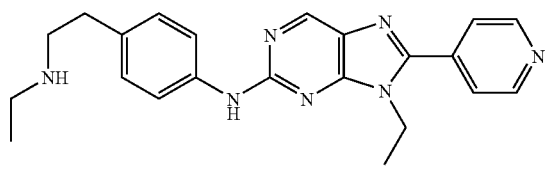

($\delta_H$, 300 MHz, CD$_3$OD) 1.32 (t, 3H), 1.53 (t, 3H), 2.98 (t, 2H), 3.12 (q, 2H), 3.28 (t, 2H), 4.50 (q, 2H), 7.28 (d, 2H), 7.80 (d, 2H), 8.22 (d, 2H), 8.87 (s, 1H), 8.92 (s, 2H); m/z (ESI) 388.2 [M+H]$^+$.

9-Ethyl-N-(4-((isopropylamino)methyl)phenyl)-8-(pyridin-4-yl)-9H-purin-2-amine

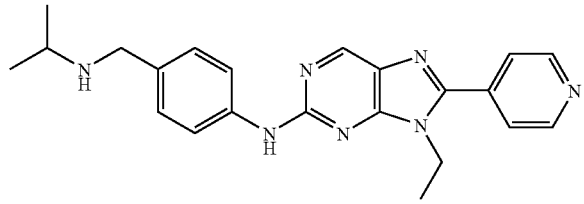

($\delta_H$, 300 MHz, CD$_3$OD) 1.41 (d, 6H), 1.53 (t, 3H), 3.44 (m, 1H), 4.18 (s, 2H), 4.50 (q, 2H), 7.49 (d, 2H), 7.96 (d, 2H), 8.18 (d, 2H), 8.92 (m, 3H); m/z (ESI) 388.2 [M+H]$^+$.

9-Methyl-N-(4-(2-(4-methylpiperazin-1-yl)ethyl)phenyl)-8-(pyridin-4-yl)-9H-purin-2-amine

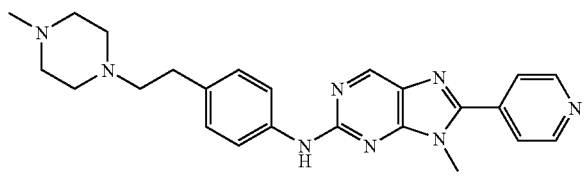

($\delta_H$, 300 MHz, CD$_3$OD) 2.66 (s, 3H), 3.04 (m, 2H), 3.36 (m, 2H), 3.59 (m, 8H), 4.03 (s, 3H), 7.29 (d, 2H), 7.80 (d, 2H), 8.35 (d, 2H), 8.88 (s, 1H), 8.92 (d, 2H); m/z (ESI) 429.2 [M+H]$^+$.

N-(4-Fluorophenyl)-9-methyl-8-(pyridin-4-yl)-9H-purin-2-amine

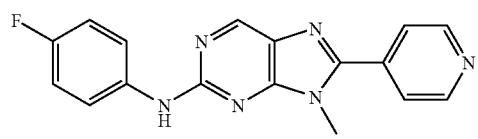

($\delta_H$, 300 MHz, CD$_3$OD) 4.02 (s, 3H), 7.08 (m, 2H), 7.77 (m, 2H), 8.35 (d, 2H), 8.85 (s, 1H), 8.93 (d, 2H); m/z (ESI) 321.3 [M+H]$^+$.

9-Cyclopropyl-N-phenyl-8-(pyridin-4-yl)-9H-purin-2-amine

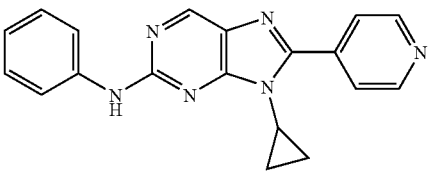

($\delta_H$, 300 MHz, CD$_3$OD) 1.17 (m, 2H), 1.43 (m, 2H), 3.88 (m, 1H), 7.20 (m, 1H), 7.49 (m, 2H), 7.99 (m, 2H), 8.59 (m, 2H), 8.99 (s, 1H), 9.02 (m, 2H); m/z (ESI) 329.2 [M+H]$^+$.

8-(2-Aminopyrimidin-4-yl)-N-(2,3-dihydro-1H-inden-5-yl)-9-ethyl-9H-purin-2-amine

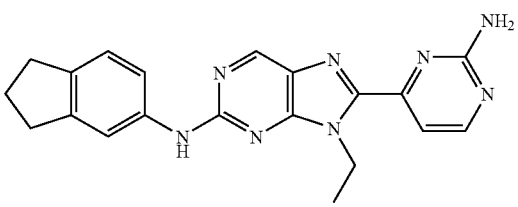

($\delta_H$, 400 MHz, d$_6$DMSO) 1.38 (t, 3H), 2.00 (m, 2H), 2.80 (m, 4H), 4.79 (q, 2H), 6.98 (bs, 2H), 7.13 (d, 1H), 7.34 (d, 1H), 7.57 (d 1H), 7.73 (s, 1H), 8.89 (d, 1H), 8.90 (s, 1H), 9.68 (s, 1H); m/z (ESI) 373.3 [M+H]$^+$.

9-Ethyl-N-(4-(2-methoxyethoxy)phenyl)-8-(pyridin-4-yl)-9H-purin-2-amine

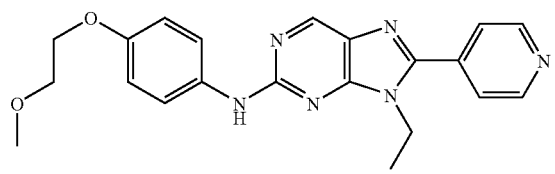

($\delta_H$, 300 MHz, CD$_3$OD) 1.27 (m, 2H), 1.50 (m, 2H), 3.43 (s, 3H), 3.75 (m, 2H), 4.14 (m, 2H), 4.46 (m, 1H), 6.97 (d, 2H), 7.63 (d, 2H), 8.17 (d, 2H), 8.82 (s, 1H), 8.91 (d, 2H); m/z (ESI) 391.2 [M+H]$^+$.

N-(3-(Aminomethyl)phenyl)-9-ethyl-8-(pyridin-4-yl)-9H-purin-2-amine

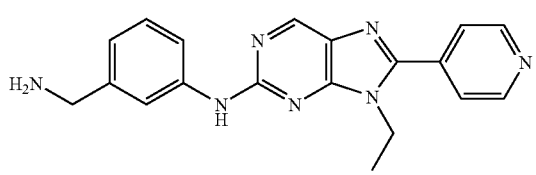

(δ_H, 300 MHz, CD_3OD) 1.56 (t, 3H), 4.15 (s, 2H), 4.54 (q, 2H), 7.15 (d, 1H), 7.44 (m, 1H), 7.91 (s, 1H), 7.93 (dd, 1H), 8.34 (d, 2H), 8.94 (s, 1H), 8.98 (d, 2H); m/z (ESI) 346.1 [M+H]+.

N-(3-((Cyclopentylamino)methyl)phenyl)-9-ethyl-8-(pyridin-4-yl)-9H-purin-2-amine

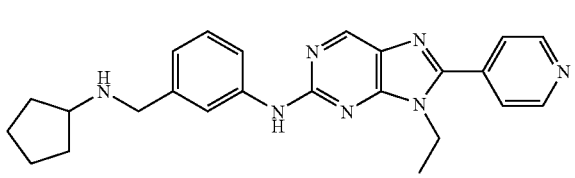

(δ_H, 300 MHz, CD_3OD) 1.53 (t, 3H), 1.70 (m, 6H), 2.20 (m, 2H), 3.62 (m, 1H), 4.22 (s, 2H), 4.54 (q, 2H), 7.18 (d, 1H), 7.46 (m, 1H), 7.93 (m, 2H), 8.29 (d, 2H), 8.95 (m, 3H); m/z (ESI) 414.2 [M+H]+.

9-Methyl-N-(4-(2-(methylamino)ethyl)phenyl)-8-(pyridin-4-yl)-9H-purin-2-amine

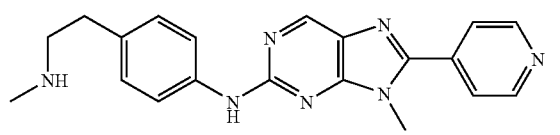

(δ_H, 300 MHz, CD_3OD) 2.75 (s, 3H), 3.03 (t, 2H), 3.28 (t, 2H), 4.08 (s, 3H), 7.38 (d, 2H), 7.77 (d, 2H), 8.67 (d, 2H), 9.02 (s, 1H), 9.08 (d, 2H); m/z (ESI) 360.1 [M+H]+.

N-(4-(2-(Cyclopentylamino)ethyl)phenyl)-9-ethyl-8-(pyridin-4-yl)-9H-purin-2-amine

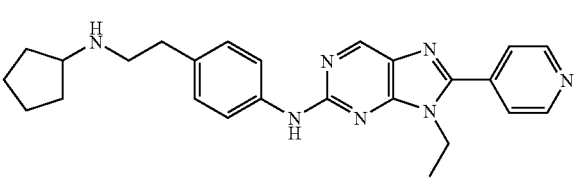

(δ_H, 300 MHz, CD_3OD) 1.53 (t, 3H), 1.70 (m, 6H), 2.12 (m, 2H), 2.93 (t, 2H), 3.25 (t, 2H), 3.56 (m, 1H), 4.48 (q, 2H), 7.28 (d, 2H), 7.79 (d, 2H), 8.28 (d, 2H), 8.85 (s, 1H), 8.94 (b, 2H); m/z (ESI) 428.3 [M+H]+.

9-Methyl-N-(3-(2-(piperazin-1-yl)ethyl)phenyl)-8-(pyridin-4-yl)-9H-purin-2-amine

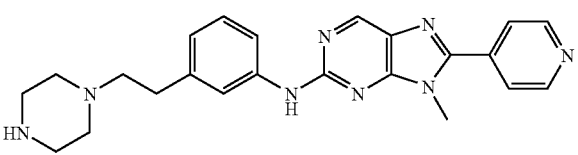

(δ_H, 300 MHz, CD_3OD) 2.73 (m, 6H), 2.83 (m, 2H), 3.12 (m, 4H), 3.94 (s, 3H), 6.88 (d, 1H), 7.25 (m, 1H), 7.68 (m, 2H), 7.92 (m, 2H), 8.77 (m, 3H); m/z (ESI) 415.2 [M+H]+.

9-Cyclopropyl-N-(4-fluorophenyl)-8-(2-(methylamino)pyrimidin-4-yl)-9H-purin-2-amine

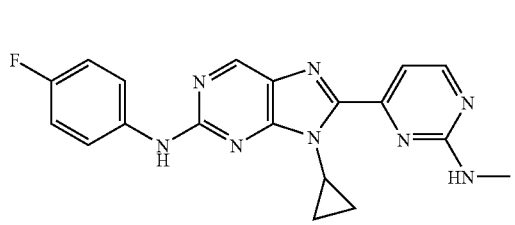

(δ_H, 300 MHz, CD_3OD) 1.26 (m, 2H), 1.38 (m, 2H), 3.36 (s, 3H), 3.98 (m, 1H), 7.23 (m, 2H), 7.57 (d, 1H), 7.97 (m, 2H), 8.56 (d, 1H), 8.96 (s, 1H); m/z (ESI) 377.2 [M+H]+.

9-Methyl-8-(pyridin-4-yl)-N-(4-(pyrrolidin-1-ylmethyl)phenyl)-9H-purin-2-amine

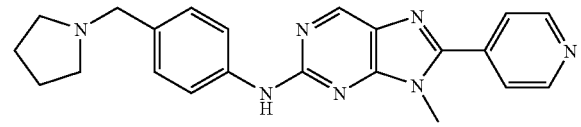

(δ_H, 300 MHz, CD_3OD) 2.00 (m, 2H), 2.19 (m, 2H), 3.19 (m, 2H), 3.51 (m, 2H), 4.04 (s, 3H), 4.35 (s, 2H), 7.50 (d, 2H), 8.00 (d, 2H), 8.26 (d, 2H), 8.90 (d, 2H), 8.91 (s, 1H); m/z (ESI) 386.2 [M+H]+.

9-Cyclopropyl-N-(3-ethylphenyl)-8-(2-(methylamino)pyrimidin-4-yl)-9H-purin-2-amine

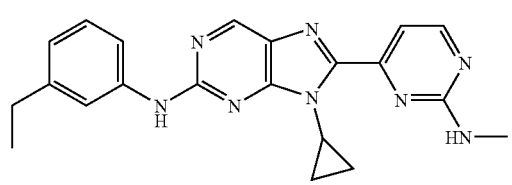

(δ_H, 300 MHz, CD_3OD) 1.39 (m, 7H), 2.83 (q, 2H), 3.22 (s, 3H), 3.99 (m, 1H), 7.06 (m, 1H), 7.40 (m, 1H), 7.64 (m, 1H), 7.71 (m, 1H), 7.93 (s, 1H), 8.54 (m, 1H), 8.97 (s, 1H); m/z (ESI) 387.3 [M+H]+.

121

8-(6-Aminopyridin-3-yl)-9-ethyl-N-(4-fluorophenyl)-9H-purin-2-amine

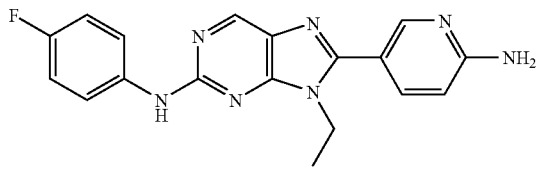

($\delta_H$, 300 MHz, CD$_3$OD) 1.48 (t, 3H), 4.35 (q, 2H), 7.09 (m, 2H), 7.19 (d, 1H), 7.72 (m, 2H), 8.31 (m, 2H), 8.76 (s, 1H); m/z (ESI) 350.2 [M+H]$^+$.

N$^1$-(8-(2-Aminopyrimidin-4-yl)-9-cyclopropyl-9H-purin-2-yl)-N$^3$,N$^3$-dimethylbenzene-1,3-diamine

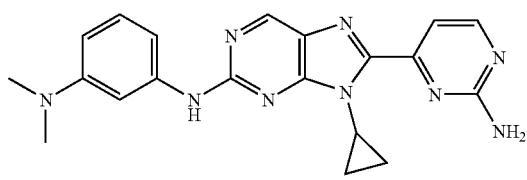

($\delta_H$, 300 MHz, d$_6$DMSO) 1.10 (m, 4H), 3.00 (s, 6H), 3.70 (m, 1H), 6.58 (d, 1H), 7.0-7.4 (m, 4H), 7.36 (d, 1H), 7.60 (s, 1H), 7.41 (d, 1H), 8.90 (s, 1H), 9.74 (s, 1H); m/z (ESI) 388.3 [M+H]$^+$.

N-(3-((Cyclopropylamino)methyl)phenyl)-9-ethyl-8-(pyridin-4-yl)-9H-purin-2-amine

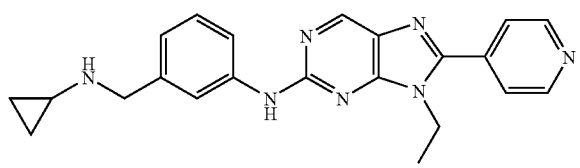

($\delta_H$, 300 MHz, CD$_3$OD) 0.91 (m, 4H), 1.55 (t, 3H), 2.81 (m, 1H), 4.32 (s, 2H), 4.55 (q, 2H), 7.19 (d, 1H), 7.42 (m, 1H), 7.93 (m, 2H), 8.27 (d, 2H), 8.91 (m, 3H); m/z (ESI) 386.2 [M+H]$^+$.

8-(2-Aminopyrimidin-4-yl)-N-(2,4-difluorophenyl)-9-ethyl-9H-purin-2-amine

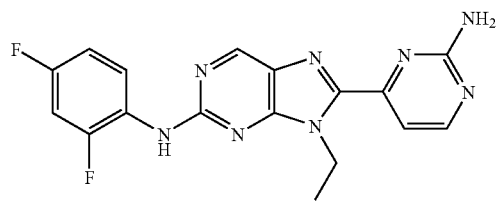

122

($\delta_H$, 400 MHz, d$_6$DMSO) 1.33 (t, 3H), 4.71 (q, 2H), 6.91 (bs, 2H), 7.08 (m, 1H), 7.32 (m, 2H), 7.76 (m, 1H), 8.39 (d, 1H), 8.85 (s, 1H), 9.25 (s, 1H); m/z (ESI) 369.2 [M+H]$^+$.

N-(4-(9-Cyclopropyl-8-(pyridin-4-yl)-9H-purin-2-ylamino)phenethyl)acetamide

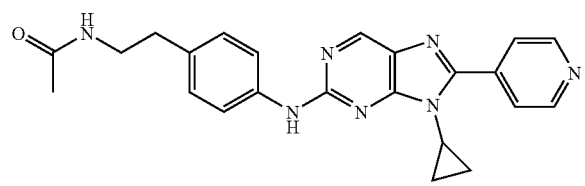

($\delta_H$, 300 MHz, CD$_3$OD) 1.03 (m, 2H), 1.29 (m, 2H), 1.92 (s, 3H), 2.79 (t, 2H), 3.38 (t, 2H), 3.74 (m, 1H), 7.23 (m, 2H), 7.79 (m, 2H), 8.45 (m, 2H), 8.84 (s, 1H), 8.89 (d, 2H); m/z (ESI) 414.2 [M+H]$^+$.

N-(4-(9-Ethyl-8-(pyridin-4-yl)-9H-purin-2-ylamino)phenethyl)-N-methylacetamide

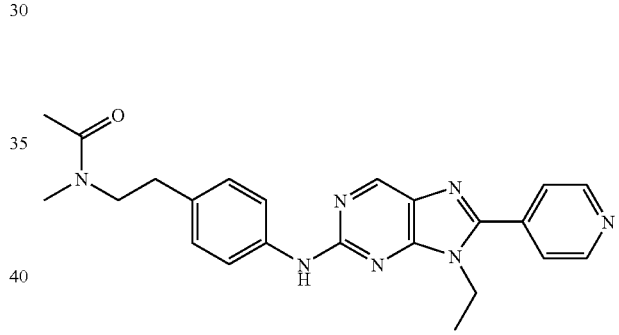

($\delta_H$, 300 MHz, CD$_3$OD, Rotational Isomers) 1.53 (m, 3H), [1.79 (s) & 2.07 (s), 3H, rotational isomers], 2.87 (m, 2H), [3.00 (s) & 3.06 (s), 3H, rotational isomers], 3.62 (m, 2H), 4.51 (q, 2H), 7.23 (m, 2H), 7.74 (m, 2H), 8.29 (m, 2H), [8.87 (s) & 8.88 (s), 1H, rotational isomers], 8.93 (d, 2H); m/z (ESI) 416.3 [M+H]$^+$.

N-(4-(9-Methyl-8-(pyridin-4-yl)-9H-purin-2-ylamino)benzyl)acetamide

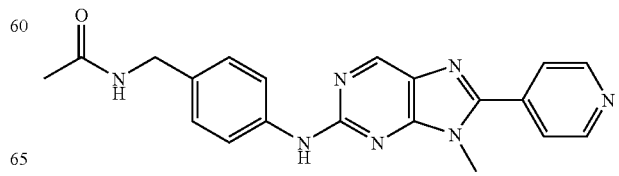

($\delta_H$, 300 MHz, CD$_3$OD) 2.02 (s, 3H), 4.07 (s, 3H), 4.38 (s, 2H), 7.37 (d, 2H), 7.70 (d, 2H), 8.64 (d, 2H), 8.99 (s, 1H), 9.06 (d, 2H); m/z (ESI) 374.2 [M+H]$^+$.

9-Ethyl-N-(4-(2-(piperidin-1-yl)ethoxy)phenyl)-8-(pyridin-4-yl)-9H-purin-2-amine

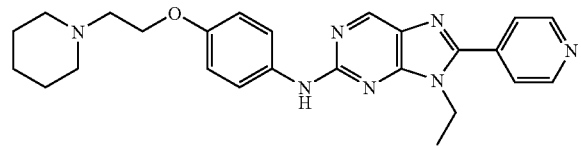

($\delta_H$, 300 MHz, CD$_3$OD) 1.50 (t, 3H), 1.85 (m, 6H), 3.10 (m, 2H), 3.57 (t, 2H), 3.63 (m, 2H), 4.37 (t, 2H), 4.45 (q, 2H), 7.04 (d, 2H), 7.74 (d, 2H), 8.08 (d, 2H), 8.82 (s, 1H), 8.87 (d, 2H); m/z (ESI) 444.2 [M+H]$^+$.

N-(4-(2-Methoxyethoxy)phenyl)-9-methyl-8-(pyridin-4-yl)-9H-purin-2-amine

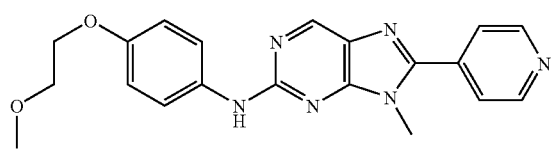

($\delta_H$, 300 MHz, CD$_3$OD) 3.45 (s, 3H), 3.77 (m, 2H), 4.00 (s, 3H), 4.14 (m, 2H), 6.97 (d, 2H), 7.63 (d, 2H), 8.27 (d, 2H), 8.80 (s, 1H), 8.91 (d, 2H); m/z (ESI) 377.3 [M+H]$^+$.

8-(2-Chloropyridin-4-yl)-9-isopropyl-N-(3-methoxyphenyl)-9H-purin-2-amine

($\delta_H$, 300 MHz, CDCl$_3$) 1.77 (d, 6H), 3.82 (s, 3H), 4.68 (m, 1H), 6.73 (m, 1H), 7.26 (m, 2H), 7.38 (m, 1H), 7.48 (m, 1H), 7.63 (s, 1H), 8.65 (m, 2H), 11.3 (s, 1H); m/z (ESI) 395.1 [M+H]$^+$.

8-(2-Aminopyridin-4-yl)-9-isopropyl-N-(3-methoxyphenyl)-9H-purin-2-amine

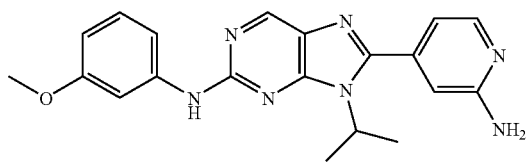

($\delta_H$, 300 MHz, CD$_3$OD) 1.95 (d, 6H), 4.00 (s, 3H), 4.95 (m, 1H), 6.78 (m, 1H), 7.26 (d, 1H), 7.40 (m, 3H), 7.72 (m, 1H), 8.18 (d, 1H), 8.99 (s, 1H); m/z (ESI) 376.5 [M+H]$^+$.

9-Ethyl-N-(4-(2-(methylamino)ethyl)phenyl)-8-(pyridin-3-yl)-9H-purin-2-amine

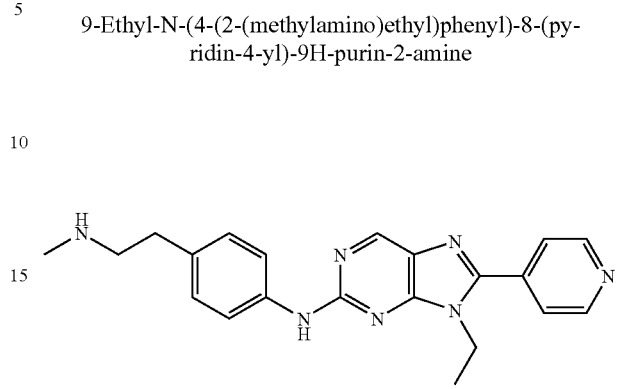

($\delta_H$, 300 MHz, CD$_3$OD) 1.53 (t, 3H), 2.74 (s, 3H), 2.99 (t, 2H), 3.30 (t, 2H), 4.50 (q, 2H), 7.29 (d, 2H), 7.81 (d, 2H), 8.27 (d, 2H), 8.89 (s, 1H), 8.94 (d, 2H); m/z (ESI) 374.2 [M+H]$^+$.

9-Ethyl-N-(4-(2-morpholinoethoxy)phenyl)-8-(pyridin-4-yl)-9H-purin-2-amine

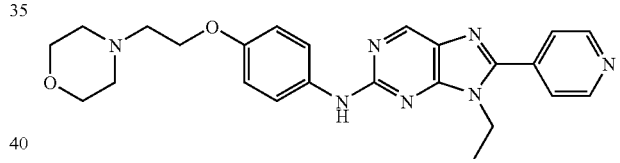

($\delta_H$, 300 MHz, CD$_3$OD) 1.51 (t, 3H), 3.20 (m, 2H), 3.60 (m, 2H), 3.66 (t, 2H), 3.90 (m, 4H), 4.40 (t, 2H), 4.45 (q, 2H), 7.04 (d, 2H), 7.71 (d, 2H), 8.27 (d, 2H), 8.86 (s, 1H), 8.95 (d, 2H); m/z (ESI) 446.2 [M+H]$^+$.

8-(2-Aminopyridin-4-yl)-N-(3,4-difluorophenyl)-9-ethyl-9H-purin-2-amine

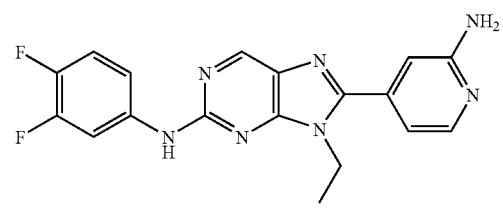

($\delta_H$, 300 MHz, CD$_3$OD) 1.57 (t, 3H), 4.47 (q, 2H), 7.31 (m, 1H), 7.39 (d, 1H), 7.43 (m, 2H), 8.02 (m, 2H), 8.87 (s, 1H); m/z (ESI) 368.3 [M+H]$^+$.

8-(2-Aminopyrimidin-4-yl)-N-(2-chlorophenyl)-9-ethyl-9H-purin-2-amine

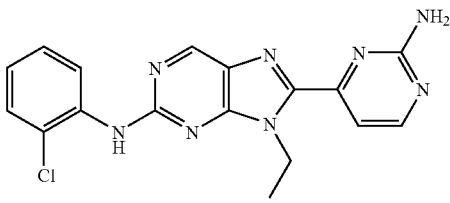

(δ$_H$, 400 MHz, d$_6$DMSO) 1.37 (t, 3H), 4.72 (q, 2H), 6.94 (bs, 2H), 7.15 (m, 1H), 7.35 (m, 2H), 7.50 (d, 1H), 7.99 (d, 1H), 8.40 (d, 1H), 8.90 (s, 2H); m/z (ESI) 367.3 [M+H]$^+$.

9-Methyl-N-(3-(piperidin-1-ylmethyl)phenyl)-8-(pyridin-4-yl)-9H-purin-2-amine

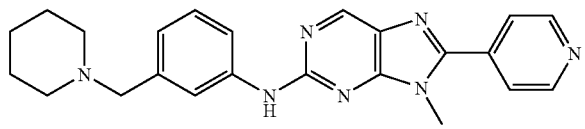

(δ$_H$, 300 MHz, CD$_3$OD) 1.53 (m, 2H), 1.78 (m, 2H), 1.94 (m, 2H), 3.02 (m, 2H), 3.52 (m, 2H), 4.05 (s, 3H), 4.31 (s, 2H), 7.17 (d, 1H), 7.48 (m, 1H), 7.96 (m, 2H), 8.32 (d, 2H), 8.91 (s, 1H), 8.94 (b, 2H); m/z (ESI) 400.2 [M+H]$^+$.

8-(6-Aminopyridin-3-yl)-9-ethyl-N-(3-ethylphenyl)-9H-purin-2-amine

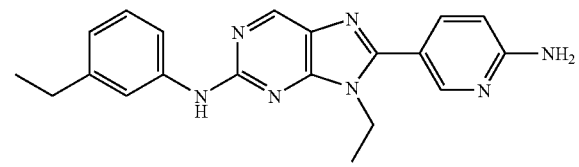

(δ$_H$, 300 MHz, CD$_3$OD) 1.28 (t, 3H), 1.52 (t, 3H), 2.67 (q, 2H), 4.38 (q, 2H), 6.92 (d, 1H), 7.19 (m, 2H), 7.55 (d, 1H), 7.66 (m, 1H), 8.29 (m, 2H), 8.75 (s, 1H); m/z (ESI) 360.3 [M+H]$^+$.

N-(4-(9-Cyclopropyl-8-(pyridin-4-yl)-9H-purin-2-ylamino)benzyl)-N-methylacetamide

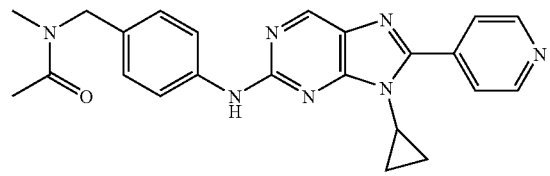

(δ$_H$, 300 MHz, CD$_3$OD, Rotational Isomers) 1.05 (m, 2H), 1.33 (m, 2H), [2.18 (s) & 2.21 (s), 3H, rotational isomers], [2.94 (s) & 3.02 (s), 3H, rotational isomers], 3.76 (m, 1H), [4.58 (s) & 4.61 (s), 2H, rotational isomers], 7.25 (m, 2H), [7.85 (d) & 7.91 (d), 2H, rotational isomers], 8.59 (m, 2H), [8.87 (s) & 8.88 (s), 1H, rotational isomers], 8.93 (d, 2H); m/z (ESI) 414.2 [M+H]$^+$.

9-Cyclopropyl-8-(pyridin-4-yl)-N-(2-(thiophen-2-yl)ethyl)-9H-purin-2-amine

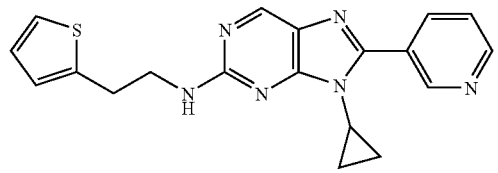

(δ$_H$, 300 MHz, CDCl$_3$) 0.92 (m, 2H), 1.18 (m, 2H) 3.20 (t, 2H), 3.42 (m, 1H), 3.79 (q, 2H), 5.48 (bt, 1H), 6.87 (m, 1H), 6.94 (m, 1H), 7.15 (dd, 1H), 7.86 (d, 2H), 8.69 (s, 1H), 8.77 (d, 2H); m/z (ESI) 363.2 [M+H]$^+$.

N-(4-(9-Cyclopropyl-8-(pyridin-4-yl)-9H-purin-2-ylamino)phenethyl)-N-methylacetamide

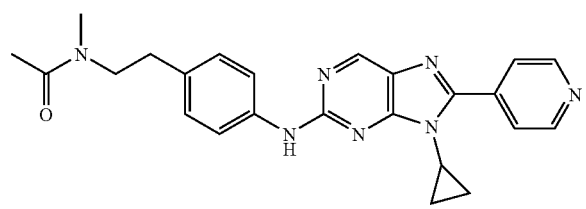

(δ$_H$, 300 MHz, CD$_3$OD, Rotational Isomers) 1.04 (m, 2H), 1.32 (m, 2H), [1.80 (s) & 2.07 (s), 3H, rotational isomers], 2.90 (m, 2H), [2.95 (s) & 3.00 (s), 3H, rotational isomers], 3.62 (m, 2H), 3.74 (m, 1H), 7.22 (m, 2H), 7.80 (m, 2H), 8.55 (m, 2H), [8.85 (s) & 8.86 (s), 1H, rotational isomers], 8.92 (d, 2H); m/z (ESI) 428.3 [M+H]$^+$.

8-(2-Aminopyrimidin-4-yl)-N-(2,6-difluorophenyl)-9-ethyl-9H-purin-2-amine

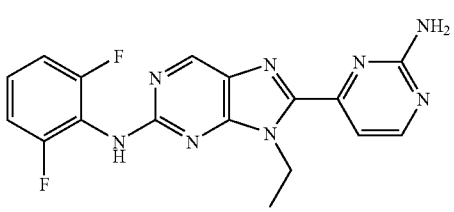

(δ_H, 400 MHz, d_6DMSO) 1.32 (t, 3H), 4.70 (q, 2H), 6.94 (bs, 2H), 7.13 (m, 2H), 7.33 (m, 2H), 8.40 (d, 1H), 8.84 (s, 1H), 9.22 (s, 1H); m/z (ESI) 369.1 [M+H]$^+$.

8-(2-Aminopyrimidin-4-yl)-N-(4-chlorophenyl)-9-ethyl-9H-purin-2-amine

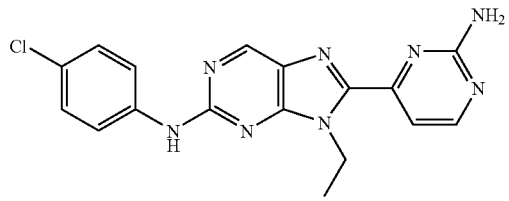

(δ_H, 400 MHz, d_6DMSO) 1.39 (t, 3H), 4.80 (q, 2H), 6.94 (bs, 2H), 7.35 (m, 3H), 7.89 (d, 2H), 8.41 (d, 1H), 8.95 (s, 1H), 9.70 (s, 1H); m/z (ESI) 367.3 [M+H]$^+$.

8-(2-Aminopyrimidin-4-yl)-N-(3-chloro-4-fluorophenyl)-9-cyclopropyl-9H-purin-2-amine

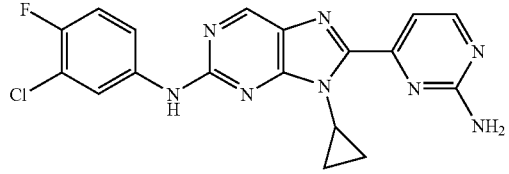

(δ_H, 300 MHz, CD_3OD) 1.18 (m, 2H), 1.35 (m, 2H), 3.84 (m, 1H), 7.21 (m, 1H), 7.59 (m, 2H), 8.48 (m, 2H), 8.89 (s, 1H); m/z (ESI) 397.2 [M+H]$^+$.

9-Methyl-N-(3-(2-(4-methylpiperazin-1-yl)ethyl)phenyl)-8-(pyridin-4-yl)-9H-purin-2-amine

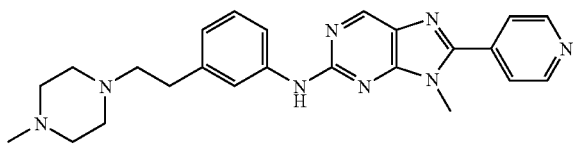

(δ_H, 300 MHz, CD_3OD) 3.02 (s, 3H), 3.14 (m, 2H), 3.41 (m, 2H), 3.60 (m, 8H), 4.11 (s, 3H), 7.08 (d, 1H), 7.40 (m, 1H), 7.77 (m, 1H), 7.86 (dd, 1H), 8.40 (d, 2H), 8.96 (s, 1H), 8.99 (d, 2H); m/z (ESI) 429.2 [M+H]$^+$.

9-Ethyl-N-(3-((isopropylamino)methyl)phenyl)-8-(pyridin-4-yl)-9H-purin-2-amine

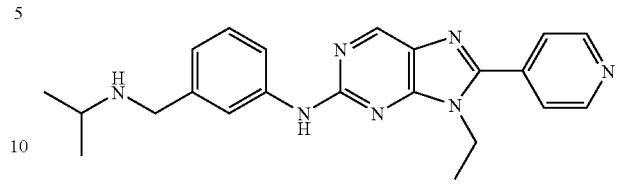

(δ_H, 300 MHz, CD_3OD) 1.40 (d, 6H), 1.51 (t, 3H), 3.48 (m, 1H), 4.20 (s, 2H), 4.47 (q, 2H), 7.12 (d, 1H), 7.44 (m, 1H), 7.90 (m, 2H), 8.04 (m, 2H), 8.86 (m, 3H); m/z (ESI) 388.2 [M+H]$^+$.

N-(2-(4-(9-Methyl-8-(pyridin-4-yl)-9H-purin-2-ylamino)phenoxy)ethyl)acetamide

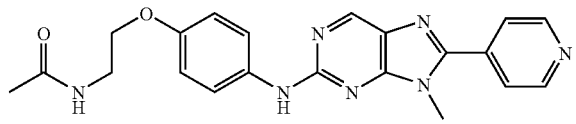

(δ_H, 300 MHz, CD_3OD) 1.98 (s, 3H), 3.57 (t, 2H), 3.99 (s, 3H), 4.06 (m, 2H), 6.97 (d, 2H), 7.66 (d, 2H), 8.22 (d, 2H), 8.81 (s, 1H), 8.87 (d, 2H); m/z (ESI) 404.3 [M+H]$^+$.

8-(2-Aminopyrimidin-4-yl)-N-(2,5-dimethylphenyl)-9-ethyl-9H-purin-2-amine

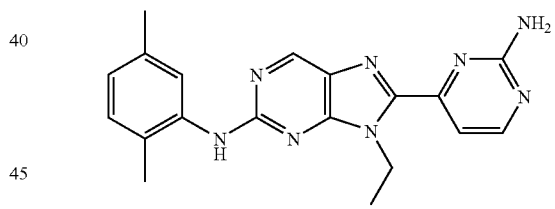

(δ_H, 400 MHz, d_6DMSO) 1.35 (t, 3H), 2.18 (s, 3H), 2.24 (s, 3H), 4.70 (q, 2H), 6.88 (m, 3H), 7.08 (d, 1H), 7.31 (d, 1H), 7.42 (s, 1H), 8.38 (d, 1H), 8.82 (s, 1H), 8.86 (s, 1H); m/z (ESI) 361.3 [M+H]$^+$.

8-(2-Aminopyrimidin-4-yl)-9-ethyl-N-(4-fluoro-2-methylphenyl)-9H-purin-2-amine

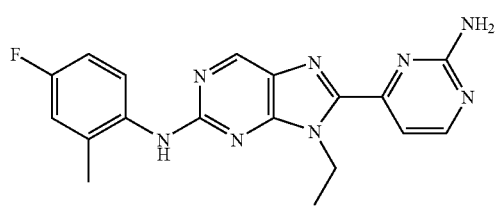

(δ$_H$, 400 MHz, d$_6$DMSO) 1.31 (t, 3H), 2.23 (s, 3H). 4.68 (q, 2H), 6.90 (bs, 2H), 7.00 (m, 1H), 7.08 (m, 1H), 7.41 (d, 1H), 7.50 (m, 1H), 8.38 (d, 1H), 8.80 (s, 1H), 8.94 (s, 1H); m/z (ESI) 365.3 [M+H]$^+$.

N-(4-((Cyclopropylamino)methyl)phenyl)-9-ethyl-8-(pyridin-4-yl)-9H-purin-2-amine

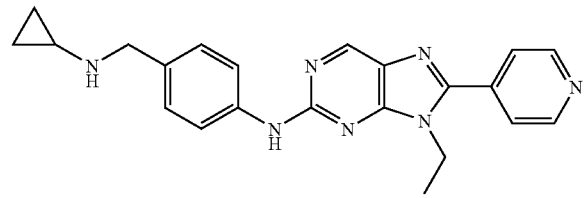

(δ$_H$, 300 MHz, CD$_3$OD) 0.92 (m, 4H), 1.54 (t, 3H), 2.79 (m, 1H), 4.29 (s, 2H), 4.51 (q, 2H), 7.47 (d, 2H), 7.95 (d, 2H), 8.17 (d, 2H), 8.90 (m, 3H); m/z (ESI) 386.2 [M+H]$^+$.

9-Cyclopropyl-8-(pyrimidin-4-yl)-N-(2-(thiophen-2-yl)ethyl)-9H-purin-2-amine

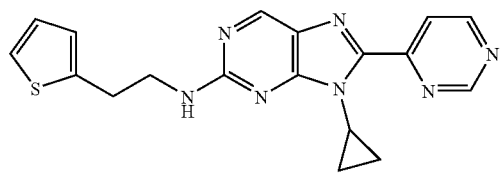

(δ$_H$, 300 MHz, CDCl$_3$) 1.05 (m, 2H), 1.28 (m, 2H), 3.27 (m, 2H), 3.86 (m, 3H), 6.96 (m, 2H), 7.17 (m, 1H), 8.27 (m, 1H), 8.65 (s, 1H), 9.05 (m, 1H), 9.12 (m, 1H), 9.46 (s, 1H); m/z (ESI) 364.1 [M+H]$^+$.

N-(4-(2-(Dimethylamino)ethoxy)phenyl)-9-ethyl-8-(pyridin-4-yl)-9H-purin-2-amine

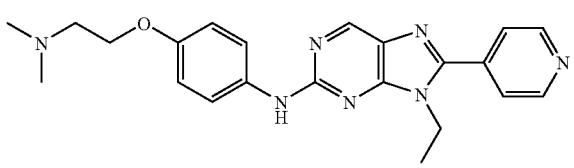

(δ$_H$, 300 MHz, CD$_3$OD) 1.51 (t, 3H), 3.01 (s, 6H), 3.61 (t, 2H), 4.36 (t, 2H), 4.46 (q, 2H), 7.06 (d, 2H), 7.75 (d, 2H), 8.11 (d, 2H), 8.83 (s, 1H), 8.89 (d, 2H); m/z (ESI) 404.2 [M+H]$^+$.

N-(Benzo[d]thiazol-6-yl)-9-cyclopropyl-8-(pyridin-4-yl)-9H-purin-2-amine

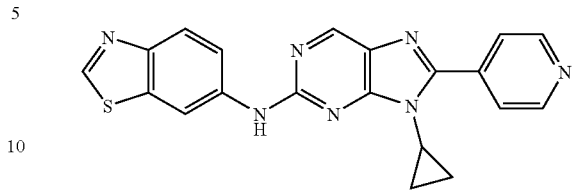

(δ$_H$, 300 MHz, CD$_3$OD) 1.07 (m, 2H), 1.34 (m, 2H), 3.79 (m, 1H), 7.81 (dd, 1H), 7.99 (d, 1H), 8.49 (d, 2H), 8.92 (m, 3H), 8.97 (s, 1H), 9.10 (s, 1H); m/z (ESI) 386.2 [M+H]$^+$.

9-Ethyl-N-(4-fluoro-3-methoxyphenyl)-8-(pyridin-4-yl)-9H-purin-2-amine

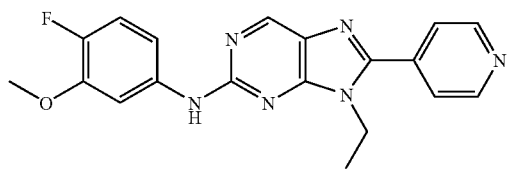

(δ$_H$, 300 MHz, CD$_3$OD) 1.55 (t, 3H), 3.94 (s, 3H), 4.51 (q, 2H), 7.06 (m, 1H), 7.21 (m, 1H), 7.80 (dd, 1H), 8.25 (d, 2H), 8.88 (s, 1H), 8.93 (b, 2H); m/z (ESI) 365.3 [M+H]$^+$.

8-(2-Aminopyrimidin-4-yl)-N-(2,3-dihydro-1H-inden-4-yl)-9-ethyl-9H-purin-2-amine

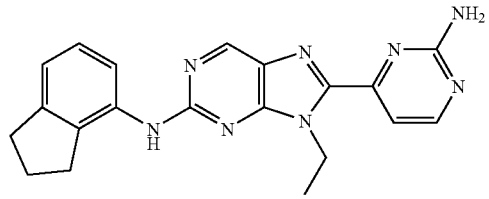

(δ$_H$, 300 MHz, d$_6$DMSO) 1.36 (t, 3H), 1.98 (m, 2H), 2.86 (m, 4H), 4.72 (q, 2H), 6.92 (m, 3H), 7.11 (m, 1H), 7.33 (d, 1H), 7.60 (d 1H), 8.40 (d, 1H), 8.87 (s, 1H), 9.00 (s, 1H); m/z (ESI) 373.3 [M+H]$^+$.

9-Ethyl-N-(4-(2-(isopropylamino)ethyl)phenyl)-8-(pyridin-4-yl)-9H-purin-2-amine

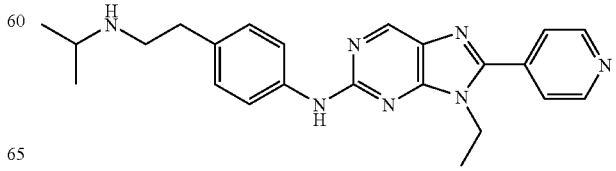

(δ$_H$, 300 MHz, CD$_3$OD) 1.34 (d, 6H), 1.53 (t, 3H), 3.01 (m, 2H), 3.25 (m, 2H), 3.42 (m, 1H), 4.48 (q, 2H), 7.29 (d, 2H), 7.80 (d, 2H), 8.15 (d, 2H), 8.87 (s, 1H), 8.89 (d, 2H); m/z (ESI) 402.2 [M+H]$^+$.

8-(2-Aminopyrimidin-4-yl)-N-(3-chloro-2-fluorophenyl)-9-cyclopropyl-9H-purin-2-amine

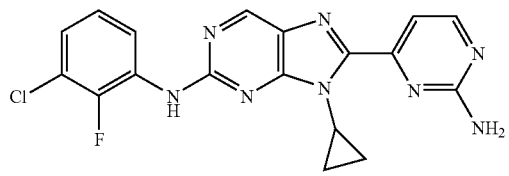

(δ$_H$, 300 MHz, d$_6$DMSO) 1.05 (m, 4H), 3.70 (m, 1H), 7.20 (m, 4H), 7.84 (m, 1H), 8.40 (d, 1H), 8.90 (s, 1H), 9.50 (s, 1H); m/z (ESI) 397.2 [M+H]$^+$.

N-(4-Fluorophenyl)-8-(pyridin-4-yl)-9H-purin-2-amine

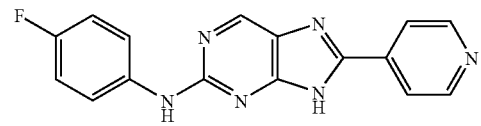

(δ$_H$, 300 MHz, CD$_3$OD) 7.06 (m, 2H), 7.77 (m, 2H), 8.41 (d, 2H), 8.87 (m, 3H); m/z (ESI) 307.2 [M+H]$^+$.

3-(8-(2-Aminopyrimidin-4-yl)-2-(3-methoxyphenylamino)-9H-purin-9-yl)propanenitrile

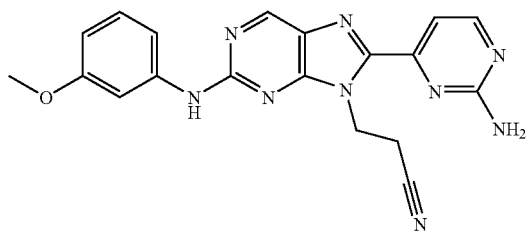

(δ$_H$, 300 MHz, CD$_3$OD) 3.37 (m, 2H), 4.00 (s, 3H), 5.30 (m, 2H), 6.79 (m, 1H), 7.41 (m, 2H), 7.79 (m, 1H), 7.88 (d, 1H), 8.54 (d, 1H), 9.08 (s, 1H); m/z (ESI) 388.2 [M+H]$^+$.

8-(2-Aminopyridin-4-yl)-N-(4-fluorophenyl)-9-methyl-9H-purin-2-amine

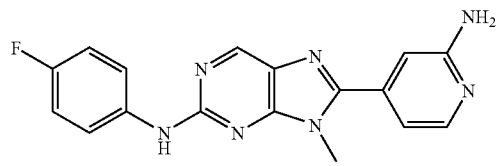

(δ$_H$, 300 MHz, CD$_3$OD) 3.99 (s, 3H), 7.08 (m, 2H), 7.42 (dd, 1H), 7.51 (s, 1H), 7.80 (m, 2H), 8.01 (s, 1H), 8.84 (s, 1H); m/z (ESI) 336.3 [M+H]$^+$.

8-(2-Aminopyrimidin-4-yl)-9-cyclopropyl-N-(3-ethylphenyl)-9H-purin-2-amine

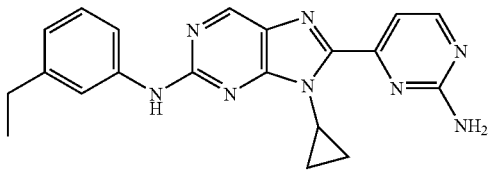

(δ$_H$, 300 MHz, CD$_3$OD) 1.33 (m, 2H), 1.42 (m, 5H), 2.82 (q, 2H), 3.95 (m, 1H), 7.04 (d, 1H), 7.38 (t, 1H), 7.72 (m, 2H), 7.91 (s, 1H), 8.51 (m, 1H), 8.97 (s, 1H); m/z (ESI) 373.3 [M+H]$^+$.

N-(4-Fluorophenyl)-8-(pyridin-4-yl)-9-(2,2,2-trifluoroethyl)-9H-purin-2-amine

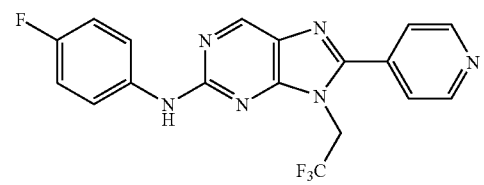

(δ$_H$, 300 MHz, CD$_3$OD) 5.28 (q, 2H), 7.09 (m, 2H), 7.77 (m, 2H), 8.21 (d, 2H), 8.90 (m, 3H); m/z (ESI) 389.2 [M+H]$^+$.

9-Ethyl-N-(4-((methylamino)methyl)phenyl)-8-(pyridin-4-yl)-9H-purin-2-amine

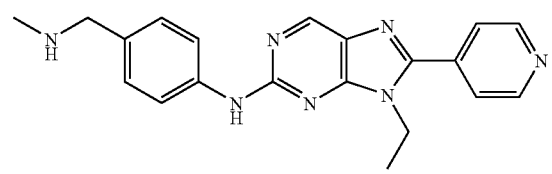

(δ$_H$, 300 MHz, CD$_3$OD) 1.52 (t, 3H), 2.75 (s, 3H), 4.16 (s, 2H), 4.49 (q, 2H), 7.45 (d, 2H), 7.96 (d, 2H), 8.06 (d, 2H), 8.88 (m, 3H); m/z (ESI) 360.2 [M+H]$^+$.

N-(3-(9-Ethyl-8-(pyridin-4-yl)-9H-purin-2-ylamino)benzyl)acetamide

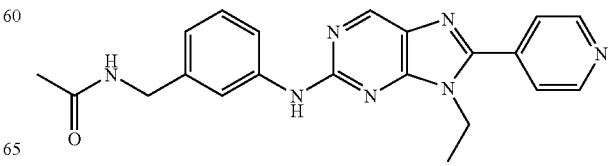

(δ$_H$, 300 MHz, CD$_3$OD) 1.54 (t, 3H), 2.01 (s, 3H), 4.39 (s, 2H), 4.52 (q, 2H), 6.99 (d, 1H), 7.31 (m, 1H), 7.67 (m, 1H), 7.81 (s, 1H), 8.29 (d, 2H), 8.88 (s, 1H), 8.93 (d, 2H); m/z (ESI) 388.3 [M+H]$^+$.

9-Methyl-8-(pyridin-4-yl)-N-(3-(pyrrolidin-1-ylmethyl)phenyl)-9H-purin-2-amine

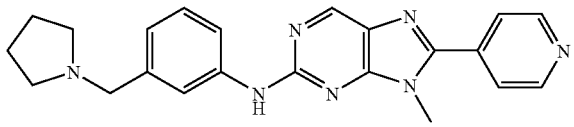

(δ$_H$, 300 MHz, CD$_3$OD) 2.04 (m, 2H), 2.17 (m, 2H), 3.24 (m, 2H), 3.48 (m, 2H), 4.07 (s, 3H), 4.41 (s, 2H), 7.18 (d, 1H), 7.47 (m, 1H), 7.97 (m, 2H), 8.43 (d, 2H), 8.94 (s, 1H), 8.96 (d, 2H); m/z (ESI) 386.2 [M+H]$^+$.

8-(2-Aminopyrimidin-4-yl)-9-ethyl-N-(5-fluoro-2-methylphenyl)-9H-purin-2-amine

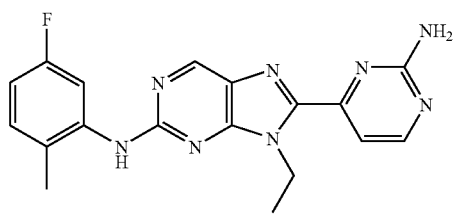

(δ$_H$, 400 MHz, d$_6$DMSO) 1.36 (t, 3H), 2.25 (s, 3H), 4.74 (q, 2H), 6.82 (m, 1H), 7.08 (bs, 2H), 7.22 (m, 1H), 7.36 (d, 1H), 7.69 (dd, 1H), 8.41 (d, 1H), 8.91 (s, 1H), 8.97 (s, 1H); m/z (ESI) 365.3 [M+H]$^+$.

8-(2-Chloropyridin-4-yl)-9-cyclopropyl-N-(2-(thiophen-2-yl)ethyl)-9H-purin-2-amine

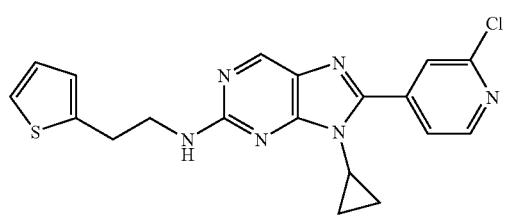

(δ$_H$, 300 MHz, CDCl$_3$) 0.98 (m, 2H), 1.30 (m, 2H), 3.26 (m, 2H), 3.46 (m, 1H), 3.86 (m, 2H), 6.95 (m, 2H), 7.16 (m, 1H), 7.84 (m, 1H), 8.51 (m, 1H), 8.63 (m, 1H), 8.66 (m, 1H), 9.65 (s, 1H); m/z (ESI) 397.1 [M+H]$^+$.

9-Methyl-N-(3-(2-morpholinoethyl)phenyl)-8-(pyridin-4-yl)-9H-purin-2-amine

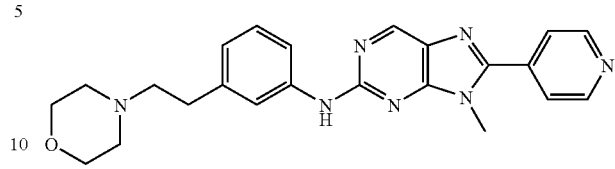

(δ$_H$, 300 MHz, CD$_3$OD) 3.12 (m, 2H), 3.25 (m, 2H), 3.45 (m, 2H), 3.58 (m, 2H), 3.81 (m, 2H), 4.01 (s, 3H), 4.08 (m, 2H), 6.99 (d, 1H), 7.34 (m, 1H), 7.69 (m, 1H), 7.79 (dd, 1H), 8.23 (d, 2H), 8.85 (s, 1H), 8.89 (d, 2H); m/z (ESI) 416.2 [M+H]$^+$.

8-(2-Chloropyridin-4-yl)-9-ethyl-N-(3-ethylphenyl)-9H-purin-2-amine

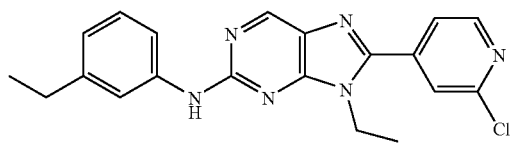

(δ$_H$, 300 MHz, CDCl$_3$) 1.27 (t, 3H), 1.52 (t, 3H), 2.68 (q, 2H), 4.36 (q, 2H), 6.95 (d, 1H), 7.30 (m, 2H), 7.38 (m, 2H), 7.75 (s, 1H), 8.60 (d, 2H), 8.76 (s, 1H); m/z (ESI) 379.2 [M+H]$^+$.

8-(2-Aminopyrimidin-4-yl)-N-(2-chloro-4-fluorophenyl)-9-cyclopropyl-9H-purin-2-amine

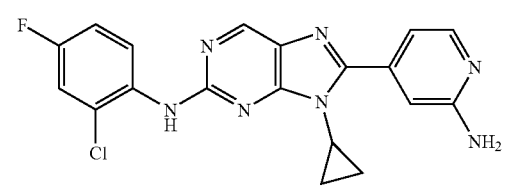

(δ$_H$, 300 MHz, CD$_3$OD) 1.02 (m, 2H), 1.18 (m, 2H), 3.78 (m, 1H), 7.18 (m, 1H), 7.31 (m, 2H), 8.43 (m, 2H), 8.79 (s, 1H); m/z (ESI) 397.2 [M+H]$^+$.

N-(4-(2-Aminoethyl)phenyl)-9-cyclopropyl-8-(pyridin-4-yl)-9H-purin-2-amine

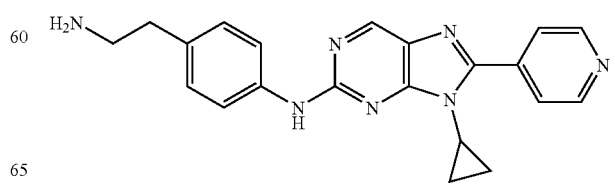

($δ_H$, 300 MHz, CD$_3$OD) 1.06 (m, 2H), 1.31 (m, 2H), 2.96 (t, 2H), 3.19 (t, 2H), 3.76 (m, 1H), 7.29 (m, 2H), 7.87 (m, 2H), 8.62 (m, 2H), 8.89 (s, 1H), 8.97 (d, 2H); m/z (ESI) 372.1 [M+H]$^+$.

N-Cyclopentyl-9-cyclopropyl-8-(pyridin-4-yl)-9H-purin-2-amine

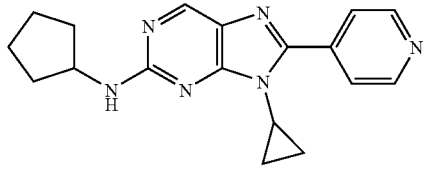

($δ_H$, 300 MHz, CD$_3$OD) 1.11 (m, 2H), 1.14 (m, 2H), 1.62 (m, 4H), 1.74 (m, 2H), 2.07 (m, 2H), 3.59 (m, 1H), 4.29 (m, 1H), 8.25 (d, 2H), 8.68 (s, 1H), 8.80 (d, 2H); m/z (ESI) 321.2 [M+H]$^+$.

8-(2-Aminopyrimidin-4-yl)-9-cyclopropyl-N-(3-fluorophenyl)-9H-purin-2-amine

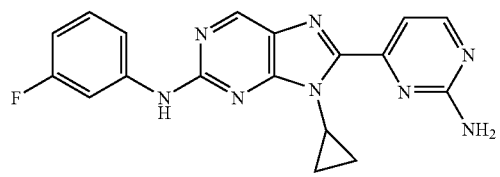

($δ_H$, 300 MHz, CD$_3$OD) 1.10 (m, 2H), 1.23 (m, 2H), 3.73 (m, 1H), 6.65 (m, 1H), 7.20 (m, 1H), 7.33 (m, 1H), 7.57 (d, 1H), 7.94 (m, 1H), 8.29 (d, 1H), 8.79 (s, 1H); m/z (ESI) 363.3 [M+H]$^+$.

9-Cyclopropyl-8-(pyridin-4-yl)-N-(2-(thiophen-2-yl)ethyl)-9H-purin-2-amine

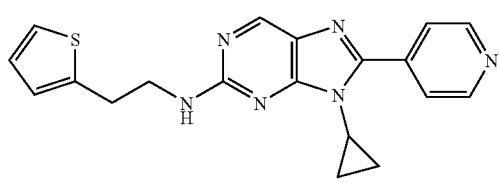

($δ_H$, 300 MHz, CDCl$_3$) 0.92 (m, 2H), 1.18 (m, 2H), 3.20 (t, 2H), 3.42 (m, 1H), 3.77 (q, 2H), 5.48 (bt, 1H), 6.87 (m, 1H), 6.94 (m, 1H), 7.15 (dd, 1H), 8.86 (m, 2H), 8.69 (s, 1H), 8.77 (d, 2H); m/z (ESI) 363.2 [M+H]$^+$.

8-(2-Aminopyrimidin-4-yl)-N-(3-chlorophenyl)-9-cyclopropyl-9H-purin-2-amine

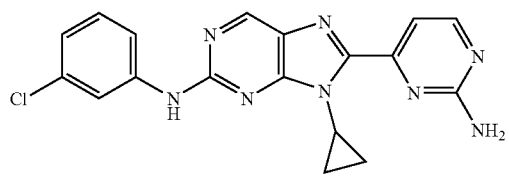

($δ_H$, 300 MHz, CD$_3$OD) 1.33 (m, 2H), 1.48 (m, 2H), 3.95 (m, 1H), 7.14 (m, 1H), 7.42 (m, 1H), 7.64 (m, 1H), 7.77 (m, 1H), 8.52 (m, 2H), 9.01 (m, 1H); m/z (ESI) 379.2 [M+H]$^+$.

N-(4-(Aminomethyl)phenyl)-9-ethyl-8-(pyridin-4-yl)-9H-purin-2-amine

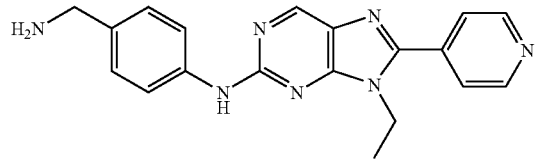

($δ_H$, 300 MHz, CD$_3$OD) 1.54 (t, 3H), 4.10 (s, 2H), 4.51 (q, 2H), 7.44 (d, 2H), 7.90 (d, 2H), 8.32 (d, 2H), 8.90 (s, 1H), 8.95 (d, 2H); m/z (ESI) 346.2 [M+H]$^+$.

N-(4-(9-Methyl-8-(pyridin-4-yl)-9H-purin-2-ylamino)benzyl)-2,2,2-trifluoroacetamide

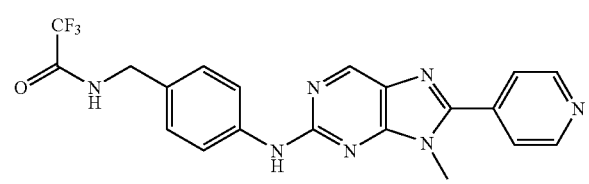

($δ_H$, 300 MHz, CD$_3$OD) 4.00 (s, 3H), 4.44 (s, 2H), 7.30 (d, 2H), 7.81 (d, 2H), 8.17 (d, 2H), 8.84 (s, 1H), 8.86 (d, 2H); m/z (ESI) 428.2 [M+H]$^+$.

9-Ethyl-N-(3-(2-(isopropylamino)ethyl)phenyl)-8-(pyridin-4-yl)-9H-purin-2-amine

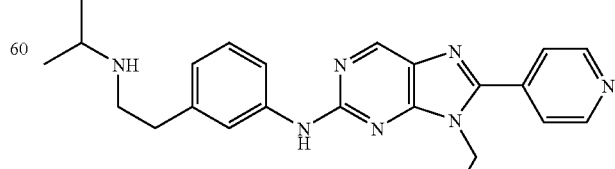

($\delta_H$, 300 MHz, CD$_3$OD) 1.36 (d, 6H), 1.53 (t, 3H), 3.01 (m, 2H), 3.27 (m, 2H), 3.31 (m, 1H), 4.49 (q, 2H), 7.00 (d, 1H), 7.34 (m, 1H), 7.69 (s, 1H), 7.78 (dd, 1H), 8.14 (d, 2H), 8.87 (s, 1H), 8.89 (d, 2H); m/z (ESI) 402.3 [M+H]$^+$.

9-Methyl-N-(3-(piperazin-1-ylmethyl)phenyl)-8-(pyridin-4-yl)-9H-purin-2-amine

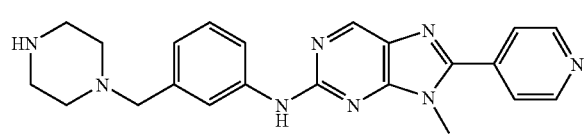

($\delta_H$, 300 MHz, CD$_3$OD) 3.54 (m, 8H), 4.07 (s, 3H), 4.39 (s, 2H), 7.19 (d, 1H), 7.45 (m, 1H), 7.89 (d, 1H), 8.05 (s, 1H), 8.44 (d, 2H), 8.92 (s, 1H), 8.96 (bs, 2H); m/z (ESI) 401.2 [M+H]$^+$.

8-(2-Aminopyrimidin-4-yl)-9-cyclopropyl-N-phenyl-9H-purin-2-amine

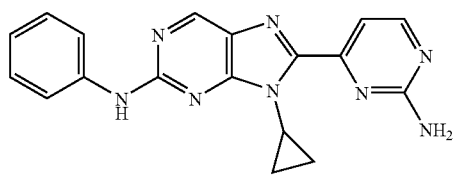

($\delta_H$, 300 MHz, CD$_3$OD) 1.11 (m, 2H), 1.19 (m, 2H), 3.71 (m, 1H), 6.95 (m, 1H), 7.24 (m, 2H), 7.50 (m 1H), 7.74 (m, 2H), 8.28 (m, 1H), 8.75 (s, 1H); m/z (ESI) 345.2 [M+H]$^+$.

8-(2-Aminopyrimidin-4-yl)-9-ethyl-N-(4-fluorophenyl)-9H-purin-2-amine

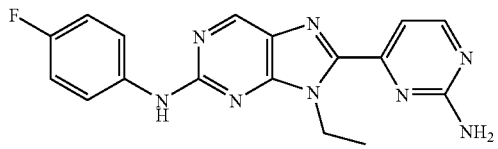

($\delta_H$, 300 MHz, CD$_3$OD) 1.63 (t, 3H), 5.04 (q, 2H), 7.22 (m, 2H), 7.86 (d, 1H), 7.93 (m, 2H), 8.49 (d, 1H), 9.02 (s, 1H); m/z (ESI) 351.2 [M+H]$^+$.

9-Methyl-N-(4-(2-(piperazin-1-yl)ethyl)phenyl)-8-(pyridin-4-yl)-9H-purin-2-amine

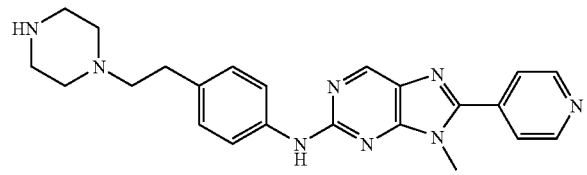

($\delta_H$, 300 MHz, CD$_3$OD) 3.07 (m, 2H), 3.48 (m, 2H), 3.64 (m, 8H), 4.04 (s, 3H), 7.30 (d, 2H), 7.80 (d, 2H), 8.42 (d, 2H), 8.89 (s, 1H), 8.94 (bs, 2H); m/z (ESI) 415.2 [M+H]$^+$.

8-(Pyridin-4-yl)-N-(2-(thiophen-2-yl)ethyl)-9H-purin-2-amine

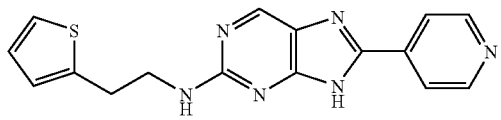

($\delta_H$, 300 MHz, CD$_3$OD) 3.14 (t, 2H), 3.69 (t, 2H) 6.84 (m, 2H), 7.12 (m, 1H), 8.20 (d, 2H), 8.70 (s, 1H), 8.76 (d, 2H); m/z (ESI) 323.2 [M+H]$^+$.

N-(4-((Dimethylamino)methyl)phenyl)-9-ethyl-8-(pyridin-4-yl)-9H-purin-2-amine

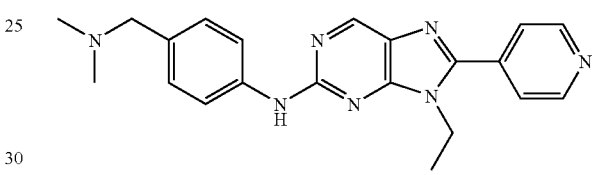

($\delta_H$, 300 MHz, CD$_3$OD) 1.52 (t, 3H), 2.87 (s, 6H), 4.28 (s, 2H), 4.51 (q, 2H), 7.48 (d, 2H), 7.95 (d, 2H), 8.33 (d, 2H), 8.87 (s, 1H), 8.95 (d, 2H); m/z (ESI) 374.2 [M+H]$^+$.

8-(2-Aminopyrimidin-4-yl)-9-ethyl-N-(5,6,7,8-tetrahydronaphthalen-1-yl)-9H-purin-2-amine

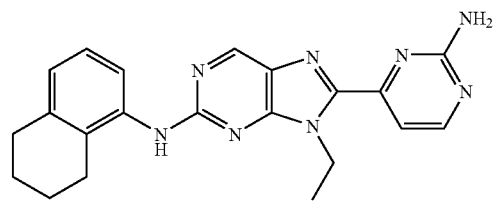

($\delta_H$, 400 MHz, d$_6$DMSO) 1.32 (t, 3H), 1.70 (m, 4H), 2.65 (m, 2H), 2.75 (m, 2H), 4.70 (q, 2H), 6.88 (d, 1H), 7.08 (m, 1H), 7.35 (m, 4H), 8.38 (d, 1H), 8.85 (s, 1H), 8.90 (s, 1H); m/z (ESI) 387.3 [M+H]$^+$.

We claim:
1. A compound of formula I:

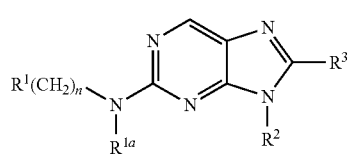

wherein
R¹ is chosen from aryl, heteroaryl, $C_1$-$C_{10}$ alkyl, substituted aryl, substituted heteroaryl, and substituted $C_1$-$C_{10}$ alkyl;
n is chosen from 0,1, and 2;
$R^{1a}$ is hydrogen or methyl;
R² is chosen from;
    hydrogen;
    $C_1$-$C_6$ alkyl; and
    $C_1$-$C_6$ alkyl substituted with CN or fluorine; and
R³ is chosen from aryl substituted with one or two alkoxy, and heteroaryl optionally substituted with one to three substituents chosen from the group consisting of:
lower alkyl, hydroxyl, hydroxyloweralkyl, lower alkoxy, amino, alkylamino, dialkylamino, acylamino, alkoxycarbonyl, and halogen.

2. A compound according to claim 1:
wherein
R³ is chosen from heteroaryl optionally substituted with one to three substituents chosen from the group consisting of:
lower alkyl, hydroxy, lower alkoxy, amino, alkylamino, dialkylamino, and acylamino.

3. A compound according to claim 2 wherein:
R¹ is chosen from aryl, heteroaryl, and $C_1$-$C_{10}$ alkyl, each optionally substituted with one to three substituent(s) chosen from the group consisting of:
alkyl, halo, lower alkoxy, haloalkyl, hydroxy, cyano, nitro, amino, alkylamino, dialkylamino, aminoalkyl, alkylaminoalkyl, dialkylaminoalkyl, mercapto, alkylthio, alkylsulfinyl, alkylsulfonyl, acylamino, acylaminoalkyl, oxaalkyl, heterocyclylalkyl, dialkylaminoalkoxy, (alkyl)(acyl)aminoalkyl, trifluoromethoxy, acylaminoalkoxy, and heterocyclylalkoxy.

4. A compound according to claim 2, wherein R¹ is phenyl substituted with one substitutent chosen from the group consisting of methylenedioxy, halogen, alkyl, aminomethyl, alkylaminomethyl, dialkylaminomethyl, oxaalkyl, dialkylaminoalkoxy, (alkyl)(acyl)aminoalkyl, trifluoromethoxy, acylaminoalkoxy, heterocyclylalkoxy, and

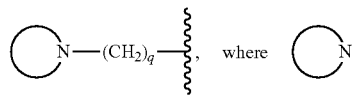

is a nitrogen heterocycle; and
q is 1-3.

5. A compound according to claim 2, wherein R¹ is phenyl or phenyl substituted with methylenedioxy, lower alkyl, halogen, alkyl, aminomethyl, alkylaminomethyl, dialkylaminomethyl, acylamino, and acylaminoalkyl.

6. A compound according to claim 2, wherein R¹ is thienyl and n is 2.

7. A compound according to claim 2, wherein R¹ is lower alkyl and n is 0.

8. A compound according to claim 2, wherein $R^{1a}$ is H.

9. A compound according to claim 2, wherein n is 0.

10. A compound according to claim 2, wherein R² is chosen from $C_1$-$C_3$ alkyl, fluorinated $C_1$-$C_3$ alkyl, and cyano $C_1$-$C_3$ alkyl.

11. A compound according to claim 2, wherein R² is chosen from cyclopropyl, isopropyl, 2-cyanoethyl, ethyl, trifluoroethyl, hydrogen, and methyl.

12. A compound according to claim 2, wherein R³ is chosen from nitrogen heteroaryl and substituted nitrogen heteroaryl.

13. A compound according to claim 12, wherein R³ is formula II

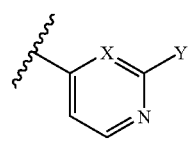

wherein
X is chosen from CH, C-halogen, and nitrogen;
Y is chosen from H, halogen, $NH_2$, NHMe, NHEt, $NMe_2$, NHAc, OH, OMe, OEt, Me, and Et.

14. A compound according to claim 13, wherein Y is chosen from H, $NH_2$, and NHMe.

15. A compound according to claim 1, wherein R³ is substituted phenyl.

16. A compound according to claim 13, wherein R³ is chosen from 4-pyridinyl, 2-aminopyrimidin-4-yl and 2-(methylamino)pyrimidin-4-yl.

17. A compound according to claim 13, wherein R³ is chosen from 4-pyridyl, 4-pyrimidinyl, 4-(2-aminopyrimidyl), and 4-(2-aminopyridinyl).

18. A compound according to claim 2 wherein:
R¹ is chosen from phenyl and phenyl substituted with alkoxy, halogen, aminoalkyl, or acylaminoalkyl;
n is chosen from 0,1, and 2;
$R^{1a}$ is hydrogen;
R² is chosen from cyclopropyl, isopropyl, ethyl, 2-cyanoethyl, hydrogen, and methyl; and
R³ is chosen from 4-pyridyl, 4-pyrimidinyl, 4-(2-aminopyrimidyl), and 4-(2-aminopyridinyl).

19. A pharmaceutical formulation comprising a compound according to claim 1 and a pharmaceutically acceptable carrier.

20. A compound according to claim 1 chosen from:
9-Cyclopropyl-8-(2-(methylamino)pyrimidin-4-yl)-N-m-tolyl-9H-purin-2-amine;
N-(4-(9-Methyl-8-(pyridin-4-yl)-9H-purin-2-ylamino) benzyl)-N-methylacetamide;
8-(2-Aminopyridin-4-yl)-9-cyclopropyl-N-(3-methoxyphenyl)-9H-purin-2-amine;
8-(2-Aminopyrimidin-4-yl)-9-ethyl-N-(4-fluoro-3-methylphenyl)-9H-purin-2-amine;
tert-Butyl 4-(9-cyclopropyl-8-(pyridin-4-yl)-9H-purin-2-ylamino) phenethylcarbamate;
9-Ethyl-N-(4-fluoro-3-methoxyphenyl)-8-(2-(methylamino)pyrimidin-4-yl)-9H-purin-2-amine;
9-Cyclopropyl-N-(3-fluorophenyl)-8-(2-(methylamino) pyrimidin-4-yl)-9H-purin-2-amine;
N-(4-(9-Ethyl-8-(pyridin-4-yl)-9H-purin-2-lamino)benzyl) -N-methylacetamide;
8-(2-Aminopyrimidin-4-yl)-9-ethyl-N-(4-ethylphenyl)-9H-purin-2-amine;
9-Methyl-N-(3-((4-methylpiperazin-1-yl)methyl)phenyl)-8-(pyridin-4-yl)-9H-purin-2-amine;
9-Cyclopropyl-8-(pyridin-4-yl)-N-(3-(trifluoromethoxy) phenyl)-9H-purin-2-amine;
9-Ethyl-N-(3-(2-morpholinoethoxy)phenyl)-8-(pyridin-4-yl)-9H-purin-2-amine;
9-Methyl-N-(4-(piperazin-1-ylmethyl)phenyl)-8-(pyridin-4-yl)-9H-purin-2-amine;

N-(3-(2-(Cyclopentylamino)ethyl)phenyl)-9-ethyl-8-(pyridin-4-yl)-9H-purin-2-amine;
N-(3-(Aminomethyl)phenyl)-9-cyclopropyl-8-(pyridin-4-yl)-9H-purin-2-amine;
9-Isopropyl-N-(3-methoxyphenyl)-8-(2-(methylamino)pyrimidin-4-yl)-9H-purin-2-amine;
N-(8-(2-Aminopyrimidin-4-yl)-9-cyclopropyl-9H-purin-2-yl)quinolin-6-amine;
N-(3-Chlorophenyl)-9-cyclopropyl-8-(2-(methylamino)pyrimidin-4-yl)-9H-purin-2-amine;
9-Cyclopropyl-N-(4-((methylamino)methyl)phenyl)-8-(pyridin-4-yl)-9H-purin-2-amine;
9-Cyclopropyl-N-phenethyl-8-(pyridin-4-yl)-9H-purin-2-amine;
8-(2-Aminopyrimidin-4-yl)-9-ethyl-N-(3-fluorophenyl)-9H-purin-2-amine;
8-(2-Aminopyrimidin-4-yl)-9-isopropyl-N-(3-methoxyphenyl)-9H-purin-2-amine ;
9-Cyclopropyl-N-(3-methoxyphenyl)-8-(2-(methylamino)pyrimidin-4-yl)-9H-purin -2-amine;
9-Ethyl-N-(3-(2-methoxyethoxy)phenyl)-8-(pyridin-4-yl)-9H-purin-2-amine;
N-(3,4-Difluorophenyl)-9-ethyl-8-(pyridin-4-yl)-9H-purin-2-amine;
8-(2-Aminopyrimidin-4-yl)-N-(2,4-dimethylphenyl)-9-ethyl-9H-purin-2-amine;
9-Ethyl-N-(3-(2-(ethylamino)ethyl)phenyl)-8-(pyridin-4-yl)-9H-purin-2-amine;
9-Methyl-N-(3-(morpholinomethyl)phenyl)-8-(pyridin-4-yl)-9H-purin-2-amine;
9-Methyl-N-(4-(2-(piperidin-1-yl)ethyl)phenyl)-8-(pyridin-4-yl)-9H-purin-2-amine;
N-(4-(Aminomethyl)phenyl)-9-cyclopropyl-8-(pyridin-4-yl)-9H-purin-2-amine;
8-(2-Aminopyrimidin-4-yl)-9-cyclopropyl-N-(4-fluorophenyl)-9H-purin-2-amine;
8-(2-Aminopyrimidin-4-yl)-9-ethyl-N-o-tolyl-9H-purin-2-amine;
8-(2-Aminopyrimidin-4-yl)-9-ethyl-N-(3-ethylphenyl)-9H-purin-2-amine;
N-(8-(2-Aminopyrimidin-4-yl)-9-cyclopropyl-9H-purin-2-yl)quinolin-8-amine;
8-(2-Aminopyrimidin-4-yl)-N-(4-fluorophenyl)-9-(2,2,2-trifluoroethyl)-9H-purin-2-amine;
N-(4-(2-Aminoethyl)phenyl)-9-methyl-8-(pyridin-4-yl)-9H-purin-2-amine;
9-Ethyl-N-(3-ethylphenyl)-8-(pyridin-4-yl)-9H-purin-2-amine;
9-Isopropyl-N-(3-methoxyphenyl)-8-(pyrimidin-4-yl)-9H-purin-2-amine;
N-(4-(2-(Cyclopropylamino)ethyl)phenyl)-9-ethyl-8-(pyridin-4-yl)-9H-purin-2-amine;
N-(8-(2-Aminopyrimidin-4-yl)-9-cyclopropyl-9H-purin-2-yl)isoquinolin-5-amine;
N-(3-(2-(Dimethylamino)ethyl)phenyl)-9-ethyl-8-(pyridin-4-yl)-9H-purin-2-amine;
8-(2-Aminopyrimidin-4-yl)-9-cyclopropyl-N-(3-methoxyphenyl)-9H-purin-2-amine;
9-Ethyl-N-(3-(2-(piperidin-1-yl)ethoxy)phenyl)-8-(pyridin-4-yl)-9H-purin-2-amine;
9-Methyl-N-(4-((methylamino)methyl)phenyl)-8-(pyridin-4-yl)-9H-purin-2-amine;
8-(2-Aminopyridin-4-yl)-9-ethyl-N-(3-ethylphenyl)-9H-purin-2-amine;
8-(2-Aminopyrimidin-4-yl)-9-ethyl-N-p-tolyl-9H-purin-2-amine;
9-Cyclopropyl-N-(3,4-dimethoxyphenyl)-8-(pyridin-4-yl)-9H-purin-2-amine;
9-Methyl-8-(pyridin-4-yl)-N-(4-(2-(pyrrolidin-1-yl)ethyl)phenyl)-9H-purin-2-amine;
9-Ethyl-N-(4-fluorophenyl)-8-(pyridin-4-yl)-9H-purin-2-amine;
8-(2-Aminopyrimidin-4-yl)-9-ethyl-N-(3-fluoro-2-methylphenyl)-9H-purin-2-amine;
9-Methyl-8-(pyridin-4-yl)-N-(3-(2-(pyrrolidin-1-yl)ethy)phenyl)-9H-purin-2-amine;
N-(3-(Aminomethyl)phenyl)-9-methyl-8-(pyridin-4-yl)-9H-purin-2-amine;
9-Cyclopropyl-N-(4-fluorophenyl)-8-(pyridin-4-yl)-9H-purin-2-amine;
N-(4-Methylbenzyl)-9-cyclopropyl-8-(pyridin-4-yl)-9H-purin-2-amine;
N-(4-(9-Ethyl-8-(pyridin-4-yl)-9H-purin-2-ylamino)benzy)acetamide;
N-(3-(9-Methyl-8-(pyridin-4-yl)-9H-purin-2-ylamino)benzyl)acetamide;
N-(4-(Aminomethyl)phenyl)-9-methyl-8-(pyridin-4-yl)-9H-purin-2-amine;
8-(2-Aminopyrimidin-4-yl)-9-cyclopropyl-N-(2-(thiophen-2-yl)ethyl)-9H-purin-2amine;
8-(2-Aminopyridin-4-yl)-9-ethyl-N-(4-fluorophenyl)-9H-purin-2-amine, N-(3-(2-(Dimethylamino)ethoxy)phenyl)-9-ethyl-8-(pyridin-4-yl)-9H-purin-2-amine;
9-Methyl-N-(4-(piperidin-1-ylmethyl)phenyl)-8-(pyridin-4-yl)-9H-purin-2-amine;
8-(2-Aminopyrimidin-4-yl)-N-(3,5-difluorophenyl)-9-ethyl-9H-purin-2-amine;
N-(4-(2-(Dimethylamino)ethyl)phenyl)-9-ethyl-8-(pyridin-4-yl)-9H-purin-2amine;
9-Cyclopropyl-8-(2-(methylamino)pyrimidin-4-yl)-N-phenyl-9H-purin-2-amine;
8-(2-Aminopyrimidin-4-yl)-N-(2,5-difluorophenyl)-9-ethyl-9H-purin-2-amine;
9-Cyclopropyl-N-(3-(2-morpholinoethoxy)phenyl)-8-(pyridin-4-yl)-9H-purin-2amine;
8-(2-Aminopyrimidin-4-yl)-N-(3,4-difluorophenyl)-9-ethyl-9H-purin-2-amine;
8-(2-Aminopyrimidin-4-yl)-N-(2,3-difluorophenyl)-9-ethyl-9H-purin-2-amine;
8-(2-Aminopyrimidin-4-yl)-N-(4-fluorophenyl)-9-methyl-9H-purin-2-amine;
tert-Butyl 4-(9-cyclopropyl-8-(pyridin-4-yl)-9H-purin-2-ylamino) benzylcarbamate;
9-Cyclopropyl-N-(2,4-dimethoxyphenyl)-8-(pyridin-4-yl)-9H-purin-2-amine;
9-Methyl-N-(3-(2-(piperidin-1-yl)ethyl)phenyl)-8-(pyridin-4-yl)-9H-purin-2-amine;
N-(4-(2-Aminoethyl)phenyl)-9-ethyl-8-(pyridin-4-yl)-9H-purin-2-amine;
9-Ethyl-N-(3-((ethylamino)methyl)phenyl)-8-(pyridin-4-yl)-9H-purin-2-amine;
8-(2-Aminopyrimidin-4-yl)-9-cyclopropyl-N-m-tolyl-9H-purin-2-amine;
N-(4-(9-Methyl-8-(pyridin-4-yl)-9H-purin-2-ylamino)phenethyl)acetamide;
8-(2-Aminopyrimidin-4-yl)-N-(3,4-dimethylphenyl)-9-ethyl-9H-purin-2-amine;
N-(4-Fluorophenyl)-8-(2-(methylamino)pyrimidin-4-yl)-9-(2,2,2-trifluoroethyl)-9H-purin-2-amine;
N-(3-(9-Cyclopropyl-8-(pyridin-4-yl)-9H-purin-2-ylamino)benzyl)acetamide;
(4-(2-(4-Fluorophenylamino)-9-methyl-9H-purin-8-yl)pyridin-2-yl)methanol;

N-(4-(((Cyclopentylamino)methyl)phenyl)-9-ethyl-8-(pyridin-4-yl)-9H-purin-2-amine;
8-(2-Aminopyrimidin-4-yl)-N-(2-chloro-5-fluorophenyl)-9-cyclopropyl-9H-purin-2-amine;
N-(4-Fluorophenyl)-9-methyl-8-(2-(methylamino)pyrimidin-4-yl)-9H-purin-2-amine;
9-Cyclopropyl-N-(3-methoxyphenyl)-8-(pyrimidin-4-yl)-9H-purin-2-amine;
$N^1$-(8-(2-Aminopyrimidin-4-yl)-9-cyclopropyl-9H-purin-2-yl)-$N^4$,$N^4$-dimethylbenzene-1,4-diamine;
9-Methyl-8-(pyridin-4-yl)-N-(2-(thiophen-2-y)ethyl)-9H-purin-2-amine;
8-(2-Aminopyrimidin-4-yl)-N-(2,3-dimethylphenyl)-9-ethyl-9H-purin-2-amine;
N-(2,3-Dihydrobenzo[b][1,4]dioxin-6-yl)-9-ethyl-8-(pyridin-4-yl)-9H-purin-2-amine;
3-(2-(3-Methoxyphenylamino)-8-(pyrimidin-4-yl)-9H-purin-9-yl)propanenitrile;
9-Ethyl-N-(3-ethylphenyl)-8-(2-(methylamino)pyrimidin-4-yl)-9H-purin-2-amine;
9-Ethyl-N-(4-((ethylamino)methyl)phenyl)-8-(pyridin-4-yl)-9H-purin-2-amine;
9-Methyl-N-(4-(2-morpholinoethyl)phenyl)-8-(pyridin-4-yl)-9H-purin-2-amine;
8-(2-Chloropyridin-4-yl)-9-cyclopropyl-N-phenyl-9H-purin-2-amine;
9-Cyclopropyl-8-(1-methyl-1H-pynol-2-yl)-N-(2-(thiophen-2-yl)ethyl)-9H-purin-2-amine;
8-(2-Aminopyrimidin-4-yl)-9-ethyl-N-(3-fluoro-4-methylphenyl)-9H-purin-2amine;
9-Methyl-N-(4-((4-methylpiperazin-1-yl)methyl)phenyl)-8-(pyridin-4-yl)-9H-purin-2-amine;
8-(2-Aminopyrimidin-4-yl)-N-(3,5-dimethylphenyl)-9-ethyl-9H-purin-2-amine;
9-Methyl-N-(4-(morpholinomethyl)phenyl)-8-(pyridin-4-yl)-9H-purin-2-amine;
N-(3-((Dimethylamino)methyl)phenyl)-9-ethyl-8-(pyridin-4-yl)-9H-purin-2-amine;
8-(2-Aminopyridin-4-yl)-9-ethyl-N-(4-fluoro-3-methoxyphenyl)-9H-purin-2-amine;
8-(2-Aminopyrimidin-4-yl)-N-(3-chlorophenyl)-9-ethyl-9H-purin-2-amine;
N-(4-(9-Methyl-8-(pyridin-4-yl)-9H-purin-2-ylamino)phenethyl)-N-methylacetamide;
8-(2-Aminopyrimidin-4-yl)-N-(4-chloro-2-fluorophenyl)-9-cyclopropyl-9H-purin-2-amine;
9-Cyclopropyl-N-(4-(2-(methylamino)ethyl)phenyl)-8-(pyridin-4-yl)-9H-purin-2-amine;
9-Cyclopropyl-N-(2-fluorophenyl)-8-(pyridin-4-yl)-9H-purin-2-amine;
9-Ethyl-N-(4-(2-(ethylamino)ethyl)phenyl)-8-(pyridin-4-yl)-9H-purin-2-amine;
9-Ethyl-N-(4-((isopropylamino)methyl)phenyl)-8-(pyridin-4-yl)-9H-purin-2-amine;
9-Methyl-N-(4-(2-(4-methylpiperazin-1-yl)ethyl)phenyl)-8-(pyridin-4-yl)-9H-purin-2-amine;
9-Ethyl-N-(3-fluorophenyl)-8-(2-(methylamino)pyrimidin-4-yl)-9H-purin-2amine;
N-(4-Fluorophenyl)-9-methyl-8-(pyridin-4-yl)-9H-purin-2-amine;
9-Cyclopropyl-N-phenyl-8-(pyridin-4-yl)-9H-purin-2-amine;
8-(2-Aminopyrimidin-4-yl)-N-(2,3-dihydro-1H-inden-5-yl)-9-ethyl-9H-purin-2amine;
9-Ethyl-N-(4-(2-methoxyethoxy)phenyl)-8-(pyridin-4-yl)-9H-purin-2-amine;
N-(3-(Aminomethyl)phenyl)-9-ethyl-8-(pyridin-4-yl)-9H-purin-2-amine;
N-(3-(((Cyclopentylamino)methyl)phenyl)-9-ethyl-8-(pyridin-4-yl)-9H-purin-2amine;
9-Methyl-N-(4-(2-(methylamino)ethyl)phenyl)-8-(pyridin-4-yl)-9H-purin-2amine;
N-(4-(2-(Cyclopentylamino)ethyl)phenyl)-9-ethyl-8-(pyridin-4-yl)-9H-purin-2-amine;
9-Methyl-N-(3-(2-(piperazin-1-yl)ethyl)phenyl)-8-(pyridin-4-yl)-9H-purin-2amine;
N-(2-Fluorophenethyl)-9-cyclopropyl-8-(pyridin-4-yl)-9H-purin-2-amine;
9-Cyclopropyl-N-(4-fluorophenyl)-8-(2-(methylamino)pyrimidin-4-yl)-9H-purin-2-amine;
9-Cyclopropyl-8-(pyridin-4-yl)-N-(3,4,5-trimethoxyphenyl)-9H-purin-2-amine;
9-Methyl-8-(pyridin-4-yl)-N-(4-(pyrrolidin-1-ylmethyl)phenyl)-9H-purin-2-amine;
9-Cyclopropyl-N-(3-ethylphenyl)-8-(2-(methylamino)pyrimidin-4-yl)-9H-purin-2-amine;
8-(6-Aminopyridin-3-yl)-9-ethyl-N-(4-fluorophenyl)-9H-purin-2-amine;
$N^1$-(8-(2-Aminopyrimidin-4-yl)-9-cyclopropyl-9H-purin-2-yl)-$N^3$,$N^3$-dimethylbenzene-1,3-diamine;
N-(3-(((Cyclopropylamino)methyl)phenyl)-9-ethyl-8-(pyridin-4-yl)-9H-purin-2-amine;
8-(2-Aminopyrimidin-4-yl)-N-(2,4-difluorophenyl)-9-ethyl-9H-purin-2-amine;
9-Cyclopropyl-N-(3,5-dimethoxyphenyl)-8-(pyridin-4-yl)-9H-purin-2-amine;
N-(4-(9-Cyclopropyl-8-(pyridin-4-yl)-9H-purin-2-ylamino)phenethyl)acetamide;
N-(4-(9-Ethyl-8-(pyridin-4-yl)-9H-purin-2-ylamino)phenethyl)-N-methylacetamide;
N-(4-(9-Methyl-8-(pyridin-4-yl)-9H-purin-2-ylamino)benzyl)acetamide;
9-Ethyl-N-(4-(2-(piperidin-1-yl)ethoxy)phenyl)-8-(pyridin-4-yl)-9H-purin-2-amine;
N-(4-(2-Methoxyethoxy)phenyl)-9-methyl-8-(pyridin-4-yl)-9H-purin-2-amine;
8-(2-Chloropyridin-4-yl)-9-isopropyl-N-(3-methoxyphenyl)-9H-purin-2-amine;
8-(2-Aminopyrimidin-4-yl)-9-isopropyl-N-(3-methoxyphenyl)-9H-purin-2-amine;
9-Ethyl-N-(4-(2-(methylamino)ethyl)phenyl)-8-(pyridin-4-yl)-9H-purin-2-amine;
9-Ethyl-N-(4-(2-morpholinoethoxy)phenyl)-8-(pyridin-4-yl)-9H-purin-2-amine;
8-(2-Aminopyridin-4-yl)-N-(3,4-difluorophenyl)-9-ethyl-9H-purin-2-amine;
8-(2-Aminopyrimidin-4-yl)-N-(2-chlorophenyl)-9-ethyl-9H-purin-2-amine;
9-Methyl-N-(3-(piperidin-1-ylmethyl)phenyl)-8-(pyridin-4-yl)-9H-purin-2-amine;
8-(6-Aminopyridin-3-yl)-9-ethyl-N-(3-ethylphenyl)-9H-purin-2-amine;
N-(4-(9-Cyclopropyl-8-(pyridin-4-yl)-9H-purin-2-ylamino)benzyl)-N-methylacetamide;
9-Cyclopropyl-8-(pyridin-3-yl)-N-(2-(thiophen-2-yl)ethyl)-9H-purin-2-amine;
N-(2,2-Dimethylbenzo[d][1,3]dioxol-5-yl)-9-ethyl-8-(pyridin-4-yl)-9H-purin-2-amine;
N-(4-(9-Cyclopropyl-8-(pyridin-4-yl)-9H-purin-2-ylamino)phenethyl)-N-methylacetarnide;
9-Cyclopropyl-8-(thiazol-2-yl)-N-(2-(thiophen-2-yl)ethyl)-9H-purin-2-amine;

8-(2-Aminopyrimidin-4-yl)-N-(2,6-difluorophenyl)-9-ethyl-9H-purin-2-amine;
8-(2-Aminopyrimidin-4-yl)-9-ethyl-N-(2-fluoro-4-methylphenyl)-9H-purin-2-amine;
8-(2-Aminopyrimidin-4-yl)-N-(4-chlorophenyl)-9-ethyl-9H-purin-2-amine;
8-(2-Aminopyrimidin-4-yl)-N-(3-chloro-4-fluorophenyl)-9-cyclopropyl-9H-purin-2-amine;
9-Methyl-N-(3-(2-(4-methylpiperazin-1-yl)ethyl)phenyl)-8-(pyridin-4-yl)-9H-purin-2-amine;
9-Ethyl-N-(3-((isopropylamino)methyl)phenyl)-8-(pyridin-4-yl)-9H-purin-2-amine;
N-(8-(2-Aminopyrimidin-4-yl)-9-cyclopropyl-9H-purin-2-yl)quinolin-5-amine;
N-(2-(4-(9-Methyl-8-(pyridin-4-yl)-9H-purin-2-ylamino)phenoxy) ethyl)acetamide;
8-(2-Chloropyridin-4-yl)-9-cyclopropyl-N-(3-methoxyphenyl)-9H-purin-2-amine;
8-(2-Aminopyrimidin-4-yl)-N-(2,5-dimethylphenyl)-9-ethyl-9H-purin-2-amine;
8-(2-Aminopyrimidin-4-yl)-9-ethyl-N-(4-fluoro-2-methylphenyl)-9H-purin-2amine ;
N-(4-((Cyclopropylamino)methyl)phenyl)-9-ethyl-8-(pyridin-4-yl)-9H-purin-2amine;
8-(2-Aminopyrimidin-4-yl)-9-ethyl-N-(2-ethylphenyl)-9H-purin-2-amine;
N-(4-Methoxyphenyl)-9-methyl-8-(pyridin-4-yl)-9H-purin-2-amine;
9-Cyclopropyl-8-(pyrimidin-4-yl)-N-(2-(thiophen-2-yl)ethyl)-9H-purin-2-amine;
8-(2-Aminopyrimidin-4-yl)-9-ethyl-N-(4-fluoro-3-methoxyphenyl)-9H-purin-2-amine;
9-Cyclopropyl-8-(1-methyl-1H-imidazol-5-yl)-N-(2-(thiophen-2-yl)ethyl)-9H-purin-2-amine;
N-(Benzo[d][1,3]dioxol-5-yl)-9-cyclopropyl-8-(pyridin-4-yl)-9H-purin-2-amine;
N-(4-(2-(Dimethylamino)ethoxy)phenyl)-9-ethyl-8-(pyridin-4-yl)-9H-purin-2amine;
N-(Benzo[d]thiazol-6-yl)-9-cyclopropyl-8-(pyridin-4-yl)-9H-purin-2-amine;
9-Ethyl-N-(4-fluoro-3-methoxyphenyl)-8-(pyridin-4-yl)-9H-purin-2-amine;
8-(2-Aminopyrimidin-4-yl)-N-(2,3-dihydro-1H-inden-4-yl)-9-ethyl-9H-purin-2amine;
N-(3-(2-(Cyclopropylamino)ethyl)phenyl)-9-ethyl-8-(pyridin-4-yl)-9H-purin-2-amine;
9-Ethyl-N-(4-fluorophenyl)-8-(2-(methylamino)pyrimidin-4-yl)-9H-purin-2amine;
9-Ethyl-N-(4-(2-(isopropylamino)ethyl)phenyl)-8-(pyridin-4-yl)-9H-purin-2-amine;
8-(2-Aminopyrimidin-4-yl)-N-(3-chloro-2-fluorophenyl)-9-cyclopropyl-9H-purin-2-amine;
3-(8-(2-Aminopyrimidin-4-yl)-2-(3-methoxyphenylamino)-9H-purin-9yl)propanenitrile;
8-(2-Aminopyridin-4-yl)-N-(4-fluorophenyl)-9-methyl-9H-purin-2-amine;
N-(4-Fluorophenyl)-8-(pyridin-4-yl)-9H-purin-2-amine;
N-(4-Chlorophenyl)-9-cyclopropyl-8-(pyridin-4-yl)-9H-purin-2-amine;
8-(2-Aminopyrimidin-4-yl)-9-cyclopropyl-N-(3-ethylphenyl)-9H-purin-2-amine;
9-Ethyl-N-(4-((methylamino)methyl)phenyl)-8-(pyridin-4-yl)-9H-purin-2-amine;
N-(4-Fluorophenyl)-8-(pyridin-4-yl)-9-(2,2,2-trifluoroethyl)-9H-purin-2-amine, N-(3-(9-Ethyl-8-(pyridin-4-yl)-9H-purin-2-ylamino)benzyl)acetamide;
9-Methyl-8-(pyridin-4-yl)-N-(3-(pyrrolidin-1-ylmethyl)phenyl)-9H-purin-2-amine;

8-(2-Aminopyrimidin-4-yl)-9-ethyl-N-(5-fluoro-2-methylphenyl)-9H-purin-2-amine;
8-(2-Chloropyridin-4-yl)-9-cyclopropyl-N-(2-(thiophen-2-yl)ethyl)-9H-purin-2-amine;
8-(2-Aminopyrimidin-4-yl)-N-(5-chloro-2-fluorophenyl)-9-cyclopropyl-9H-purin-2-amine;
9-Methyl-N-(3-(2-morpholinoethyl)phenyl)-8-(pyridin-4-yl)-9H-purin-2-amine;
9-Cyclopropyl-N-(2-methoxyphenyl)-8-(pyridin-4-yl)-9H-purin-2-amine;
8-(2-Chloropyridin-4-yl)-9-ethyl-N-(3-ethylphenyl)-9H-purin-2-amine;
9-Cyclopropyl-N-(3-methoxyphenyl)-8-(pyridin-4-yl)-9H-purin-2-amine;
N-(2-Methoxyphenethyl)-9-cyclopropyl-8-(pyridin-4-yl)-9H-purin-2-amine;
Ethyl-4-(2-(4-fluorophenylamino)-9-methyl-9H-purin-8-yl)picolinate;
8-(2-Aminopyrimidin-4-yl)-N-(2-chloro-4-fluorophenyl)-9-cyclopropyl-9H-purin-2-amine;
N-(4-(2-Aminoethyl)phenyl)-9-cyclopropyl-8-(pyridin-4-yl)-9H-purin-2-amine;
N-Cyclopentyl-9-cyclopropyl-8-(pyridin-4-yl)-9H-purin-2-amine;
8-(2-Aminopyrimidin-4-yl)-9-cyclopropyl-N-(3-fluorophenyl)-9H-purin-2-amine;
9-Cyclopropyl-8-(pyridin-4-yl)-N-(2-(thiophen-2-yl)ethyl)-9H-purin-2-amine;
8-(2-Aminopyrimidin-4-yl)-9-cyclopropyl-N-phenyl-9H-purin-2-amine;
8-(2-Aminopyrimidin-4-yl)-N-(3-chlorophenyl)-9-cyclopropyl-9H-purin-2-amine;
N-(4-(Aminomethyl)phenyl)-9-ethyl-8-(pyridin-4-yl)-9H-purin-2-amine;
N-(4-(9-Methyl-8-(pyridin-4-yl)-9H-purin-2-ylamino)benzyl)-2,2,2trifluoroacetamide;
9-Ethyl-N-(3-(2-(isopropylamino)ethyl)phenyl)-8-(pyridin-4-yl)-9H-purin-2amine;
N-(3,4-Difluorophenyl)-9-ethyl-8-(2-(methylamino)pyrimidin-4-yl)-9H-purin-2amine;
9-Methyl-N-(3-(piperazin-1-ylmethyl)phenyl)-8-(pyridin-4-yl)-9H-purin-2-amine;
9-Cyclopropyl-N-isobutyl-8-(pyridin-4-yl)-9H-purin-2-amine;
9-Ethyl-8-(2-(methylamino)pyrimidin-4-yl)-N-m-tolyl-9H-purin-2-amine;
8-(2-Aminopyrimidin-4-yl)-9-cyclopropyl-N-phenyl-9H-purin-2-amine;
9-Cyclopropyl-8-(1H-pyrrol-2-yl)-N-(2-(thiophen-2-yl)ethyl)-9H-purin-2-amine;
8-(2-Aminopyrimidin-4-yl)-9-ethyl-N-(4-fluorophenyl)-9H-purin-2-amine;
8-(2-Aminopyrimidin-4-yl)-9-ethyl-N-m-tolyl-9H-purin-2-amine;
9-Methyl-N-(4-(2-(piperazin-1-yl)ethyl)phenyl)-8-(pyridin-4-yl)-9H-purin-2amine ;
8-(Pyridin-4-yl)-N-(2-(thiophen-2-yl)ethyl)-9H-purin-2-amine;
N-(44(Dimethylamino)methyl)phenyl)-9-ethyl-8-(pyridin-4-yl)-9H-purin-2amine;
9-Cyclopropyl-N-(4-methoxyphenyl)-8-(pyridin-4-yl)-9H-purin-2-amine;
8-(2-Aminopyrimidin-4-yl)-9-ethyl-N-(5,6,7,8-tetrahydronaphthalen-1-yl)-9H-purin-2-amine.

* * * * *

UNITED STATES PATENT AND TRADEMARK OFFICE
CERTIFICATE OF CORRECTION

PATENT NO.       : 7,951,803 B2
APPLICATION NO.  : 11/684262
DATED            : May 31, 2011
INVENTOR(S)      : Andrew G. Cole et al.

It is certified that error appears in the above-identified patent and that said Letters Patent is hereby corrected as shown below:

At Column 1, Line 26, Change "Biochim." to --Biochem.--.

At Column 3, Line 41, Change "defense," to --defence,--.

At Column 10, Line 34, Change "defense," to --defence,--.

At Column 11, Line 23 (Approx.), Change "NHME," to --NHMe,--.

At Column 18, Line 52, Change "5" to --S--.

At Column 18, Lines 66-67, Change "Albumine" to --Albumin--.

At Column 19, Line 13, Change "Victor" to --Victor$^2$--.

At Column 20, Line 14 (Approx.), Change "Mass." to --Mass.)--.

At Column 20, Line 61 (Approx.), Change "R$^2$—NH$_2$" to --R$^1$—NH$_2$--.

At Column 27, Line 42 (Approx.), After "purification" insert --.--.

At Column 29, Line 20 (Approx.), Change "1 atm.)" to --(1 atm.)--.

At Column 32, Lines 28-33 (Approx.),

Change " 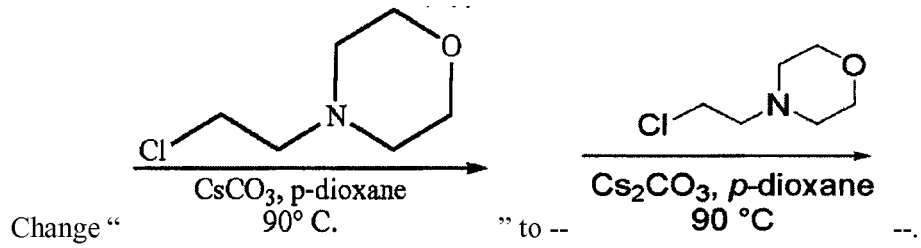 " to -- --.

At Column 32, Line 64, Change "(4" to --4--.

Signed and Sealed this
Tenth Day of January, 2012

David J. Kappos
*Director of the United States Patent and Trademark Office*

At Column 36, Lines 42-45 (approx.),
Change " 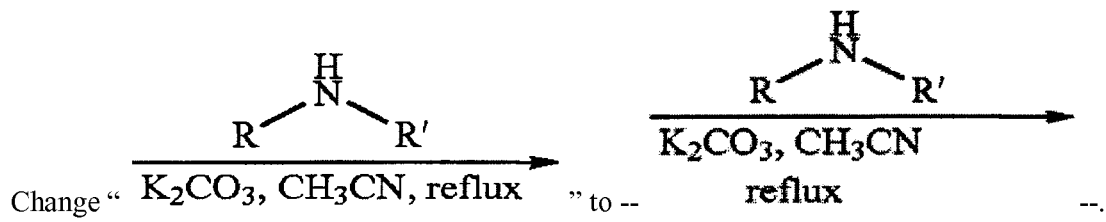 " to -- --.
At Column 40, Line 8 (Approx.), Change "Phenomonex" to --Phenomenex--.
At Column 40, Line 30, Change "Phenomonex" to --Phenomenex--.
At Columns 39-40 (Table 1), Line 3 (Approx.),
Change " 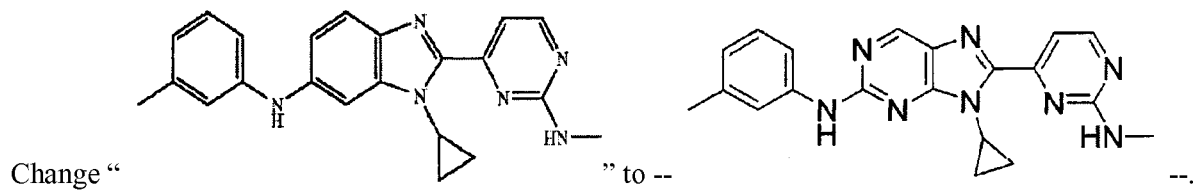 " to -- --.
At Columns 55-56 Table 1- Continued, Line 8 (Approx.),
Change " 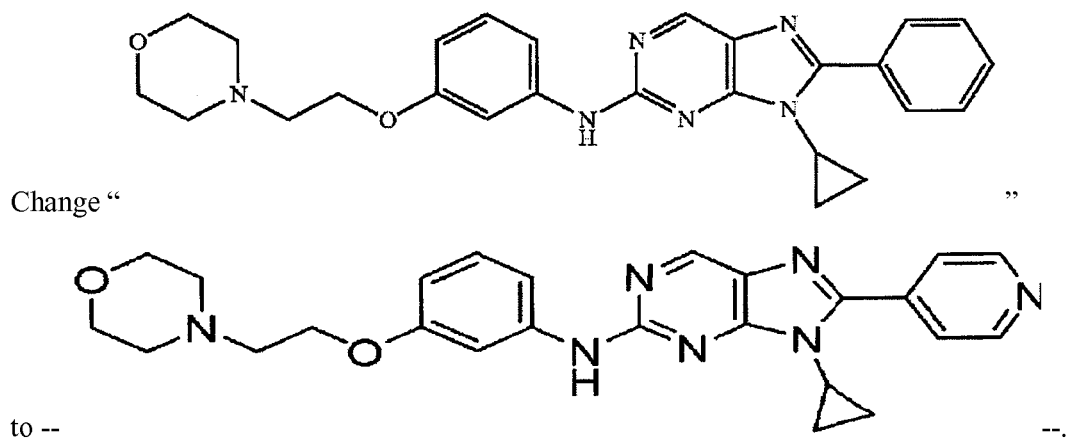 "
to -- --.

CERTIFICATE OF CORRECTION (continued)
U.S. Pat. No. 7,951,803 B2

At Columns 57-58 Table 1- Continued, Line 5 (Approx.),

Change "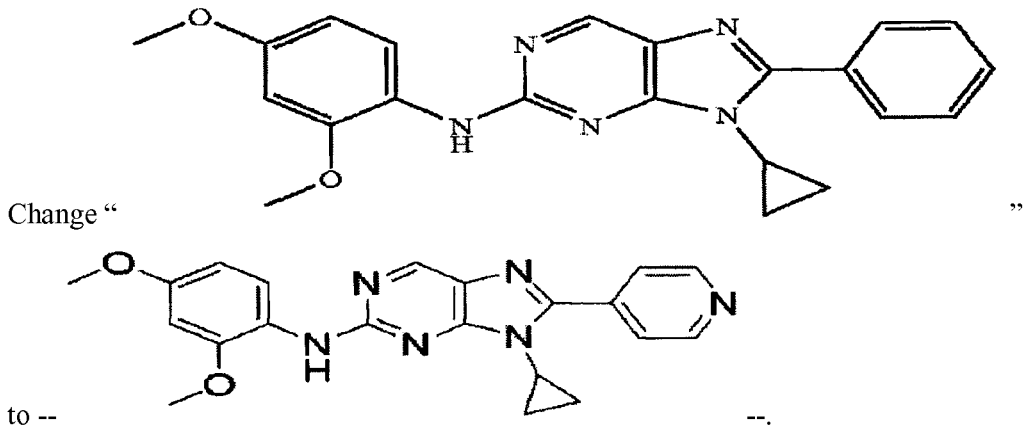"

to --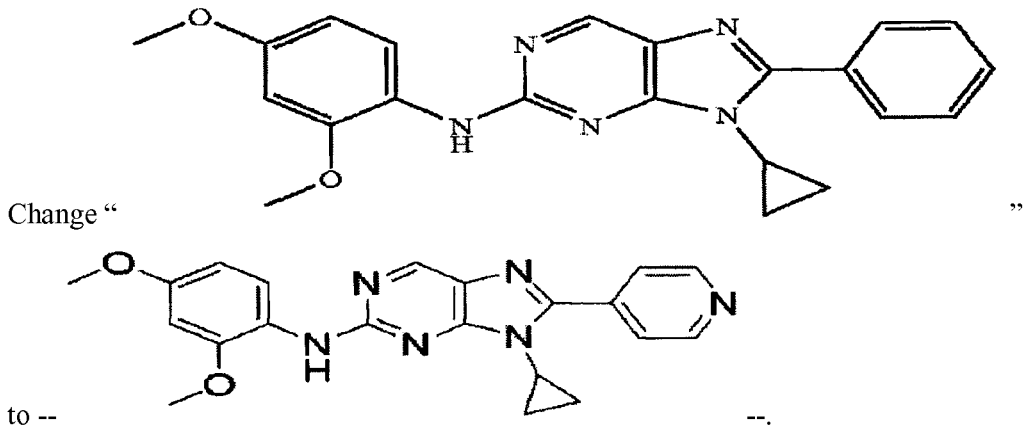--.

At Column 95, Line 1, Change ".09" to --3.09--.
At Column 98, Line 53 (Approx.), After "(s, 1H)" insert --;--.
At Column 101, Line 48 (Approx.), Change "(s, 3H)." to --(s, 3H),--.
At Column 103, Line 50, Change "(s, 3H)." to --(s, 3H),--.
At Column 110, Line 25, Change "(m 1H)," to --(m, 1H),--.
At Column 112, Lines 52-53 (Approx.), Change "(s, 1H)." to --(s, 1H),--.
At Column 112, Line 53 (Approx.), After "[M+H]$^{+}$" insert --.--.
At Column 113, Line 64, Change "(s, 3H)." to --(s, 3H),--.
At Column 114, Line 32 (Approx.), Change "(s, 6H)." to --(s, 6H),--.
At Column 118, Line 34, Change "(d 1H)," to --(d, 1H),--.
At Column 129, Line 1, Change "(s, 3H)." to --(s, 3H),--.
At Column 130, Line 52 (Approx.), Change "(d 1H)," to --(d, 1H),--.
At Column 134, Lines 41-47 (Approx.), Change "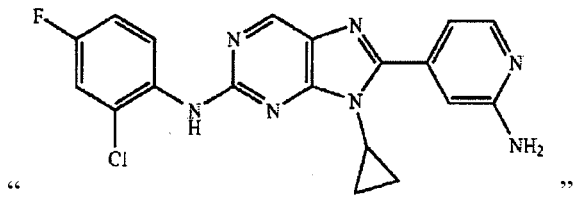"

to --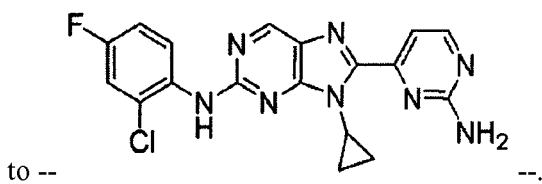--.

CERTIFICATE OF CORRECTION (continued)
U.S. Pat. No. 7,951,803 B2

At Column 138, Line 16 (Approx.), Change "(t, 2H) 6.84" to --(t, 2H), 6.84--.

At Column 139, Line 5 (Approx.), In Claim 1, change "0,1," to --0, 1,--.

At Column 139, Line 39, In Claim 4, after "of" insert --:--.

At Column 140, Line 32 (Approx.), In Claim 19, change "0,1," to --0, 1,--.

At Column 140, Lines 56-57, In Claim 20, change "lamino)benzyl) -N-methylacetamide;" to --ylamino)benzyl)-N-methylacetamide;--.

At Column 142, Lines 9-10, In Claim 20, change "1-yl)ethy)phenyl)"to --1-yl)ethyl)phenyl)--.

At Column 142, Line 24, In Claim 20, change "9H-purin-2amine;" to --9H-purin-2-amine;--.

At Column 142, Lines 26-27, In Claim 20, change "amine, N-(3-(2-(Dimethylamino)ethoxy)phenyl)-9-ethyl-8-(pyridin-4-yl)-9H-purin-2-amine;" to --amine; N-(3-(2-(Dimethylamino)ethoxy)phenyl)-9-ethyl-8-(pyridin-4-yl)-9H-purin-2-amine;--.

At Column 142, Line 33, In Claim 20, change "9H-purin-2amine;" to --9H-purin-2-amine;--.

At Column 143, Line 12 (Approx.), In Claim 20, change "2-y)ethyl)" to --2-yl)ethyl)--.

At Column 143, Line 28, In Claim 20, change "pynol" to --pyrrol--.

At Column 143, Line 59, In Claim 20, change "9H-purin-2amine;" to --9H-purin-2-amine;--.

At Column 143, Line 65, In Claim 20, change "9H-purin-2amine;" to --9H-purin-2-amine;--.

At Column 144, Line 4, In Claim 20, change "9H-purin-2amine;" to --9H-purin-2-amine;--.

At Column 144, Line 6, In Claim 20, change "9H-purin-2amine;" to --9H-purin-2-amine;--.

At Column 144, Line 10 (Approx.), In Claim 20, change "9H-purin-2amine;" to --9H-purin-2-amine;--.

At Column 144, Line 65, In Claim 20, change "methylacetarnide;" to --methylacetamide;--.

At Column 145, Line 4, In Claim 20, change "9H-purin-2amine;" to --9H-purin-2-amine;--.

At Column 145, Line 22, In Claim 20, change "9H-purin-2amine;" to --9H-purin-2-amine;--.

At Column 145, Line 24 (Approx.), In Claim 20, change "9H-purin-2amine;" to --9H-purin-2-amine;--.

At Column 145, Line 37 (Approx.), In Claim 20, change "9H-purin-2amine;" to --9H-purin-2-amine;--.

At Column 145, Line 43 (Approx.), In Claim 20, change "9H-purin-2amine;" to --9H-purin-2-amine;--.

At Column 145, Line 45 (Approx.), In Claim 20, change "9H-purin-2amine;" to --9H-purin-2-amine;--.

At Column 145, Line 47 (Approx.), In Claim 20, change "9H-purin-2amine;" to --9H-purin-2-amine;--.

At Column 145, Line 49 (Approx.), In Claim 20, change "9H-purin-2amine;" to --9H-purin-2-amine;--.

At Column 145, Lines 63-64 (Approx.), In Claim 20, change "amine, N-(3-(9-Ethyl-8-(pyridin-4-yl)-9H-purin-2-ylamino)benzyl)acetamide;" to --amine; N-(3-(9-Ethyl-8-(pyridin-4-yl)-9H-purin-2-ylamino)benzyl)acetamide;--.

At Column 146, Line 2, In Claim 20, change "9H-purin-2amine;" to --9H-purin-2-amine;--.

At Column 146, Line 4, In Claim 20, change "9H-purin-2amine;" to --9H-purin-2-amine;--.

At Column 146, Line 36, In Claim 20, change "2,2,2trifluoroacetamide;" to --2,2,2-trifluoroacetamide;--.

At Column 146, Line 38, In Claim 20, change "9H-purin-2amine;" to --9H-purin-2-amine;--.

At Column 146, Line 40, In Claim 20, change "9H-purin-2amine;" to --9H-purin-2-amine;--.

At Column 146, Line 56, In Claim 20, change "9H-purin-2amine;" to --9H-purin-2-amine;--.

At Column 146, Line 59, In Claim 20, change "(44(Dimethylamino)methyl)phenyl)" to --(4((Dimethylamino)methyl)phenyl)--.

At Column 146, Line 60, In Claim 20, change "9H-purin-2amine;" to --9H-purin-2-amine--.